(12) United States Patent
Zhu et al.

(10) Patent No.: US 12,091,686 B2
(45) Date of Patent: Sep. 17, 2024

(54) PROCESS OF PROBE QPCR USING TAQ DNA POLYMERASE MUTANTS

(71) Applicant: AbClonal Science, Inc., Woburn, MA (US)

(72) Inventors: Zhenyu Zhu, Lynnfield, MA (US); Dapeng Sun, Lexington, MA (US); Aine Quimby, Newburyport, MA (US)

(73) Assignee: ABclonal Science Inc., Woburn, MA (US)

( * ) Notice: Subject to any disclaimer, the term of this patent is extended or adjusted under 35 U.S.C. 154(b) by 0 days.

(21) Appl. No.: 18/130,012

(22) Filed: Apr. 3, 2023

(65) Prior Publication Data

US 2024/0052326 A1  Feb. 15, 2024

Related U.S. Application Data

(62) Division of application No. 17/470,557, filed on Sep. 9, 2021, now Pat. No. 11,649,441.

(60) Provisional application No. 63/088,546, filed on Oct. 7, 2020.

(51) Int. Cl.
*C12N 9/12* (2006.01)
*C12Q 1/6853* (2018.01)
*C12Q 1/686* (2018.01)

(52) U.S. Cl.
CPC .......... *C12N 9/1252* (2013.01); *C12Q 1/6853* (2013.01); *C12Q 1/686* (2013.01); *C12Y 207/07007* (2013.01)

(58) Field of Classification Search
None
See application file for complete search history.

(56) References Cited

U.S. PATENT DOCUMENTS

| 5,538,848 | A | 7/1996 | Livak et al. |
| 5,925,517 | A | 7/1999 | Tyagi et al. |
| 6,103,476 | A | 8/2000 | Tyagi et al. |
| 6,150,097 | A | 11/2000 | Tyagi et al. |
| 6,355,421 | B1 | 3/2002 | Coull et al. |
| 6,383,752 | B1 | 5/2002 | Agrawal et al. |
| 6,485,901 | B1 | 11/2002 | Gildea et al. |
| 6,548,250 | B1 | 4/2003 | Sorge |
| 6,589,250 | B2 | 7/2003 | Schendel |
| 6,589,743 | B2 | 7/2003 | Sorge |
| 6,590,091 | B2 | 7/2003 | Albagli et al. |
| 6,593,091 | B2 | 7/2003 | Keys et al. |
| 6,596,490 | B2 | 7/2003 | Dattagupta |
| 2017/0058330 | A1* | 3/2017 | Chiou ................. C12Q 1/6851 |
| 2018/0305673 | A1 | 10/2018 | Vander Horn et al. |
| 2019/0225951 | A1* | 7/2019 | Meng ..................... C12N 15/52 |

FOREIGN PATENT DOCUMENTS

| CN | 111684064 A | 9/2020 |
| WO | 99/21881 A1 | 5/1999 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Ngo et al., "Chapter—Computational Complexity, Protein Structure Prediction, and the Levinthal Paradox" included in "The Protein Folding Problem and Tertiary Structure Prediction" published on 1994 in Birkhauser, Boston, MA, United States of America, pp. 433 and 492 to 495.
Boggy et al., "A Mechanistic Model of PCR for Accurate Quantification of Quantitative PCR Data", published on Aug. 30, 2010 in PLoS ONE, vol. 5, Issue 8, 7 pages.

* cited by examiner

*Primary Examiner* — Richard G Hutson
(74) *Attorney, Agent, or Firm* — Eric P. Mirabel

(57) ABSTRACT

Disclosed are Taq DNA polymerase mutants which exhibit enhanced efficiency in qPCR compared to the wild type Taq DNA polymerase. Such mutants include: V62S, V64S, A70F, F73A, A77F, P253G, E255K, D257R, A259F, A271F, L288S, E289K, S357I, L361S, L376S, P382G, T385I, G418P, R419D, E421K, L461S, A472F, E497K, L498S, E524K, D551R, R556D, S679l, L789S, E189K/E507K/E742K (See Sequence Listing Guide for the mutants' amino acid and protein sequences).

6 Claims, 35 Drawing Sheets

Figure 1A:
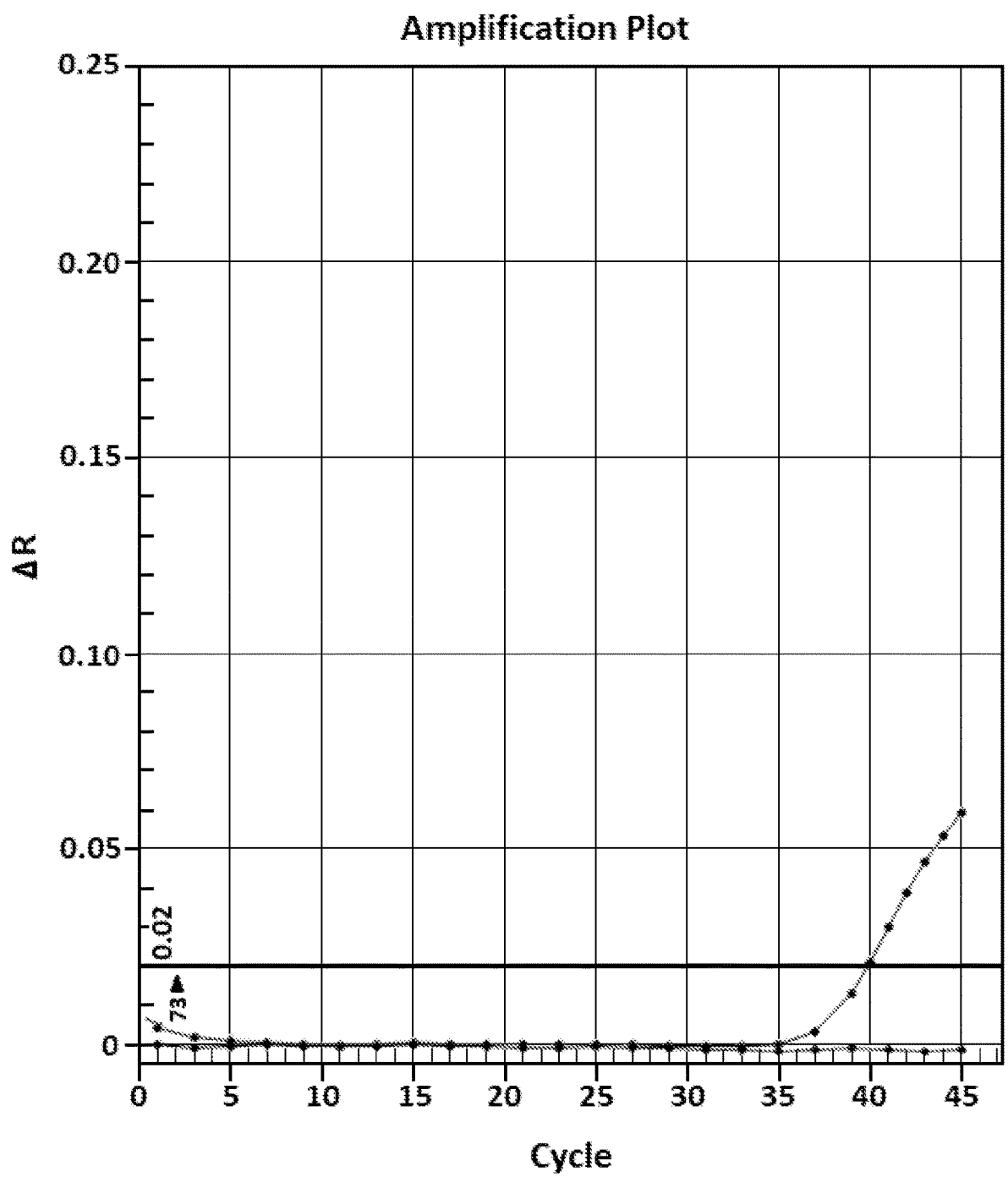

Specification includes a Sequence Listing.

F73A

A77F

WT

A70F

L288S

S357I

L361S

WT

A259F

A271F

G418P

R419D

E421K

L461S

WT

T385I

E524K

D551R

R556D

S679I

WT

E497K

L498S

WT

E189K/E507K/E742K

SEQUENCE LISTING

```
Sequence total quantity: 65
SEQ ID NO: 1            moltype = DNA  length = 2535
FEATURE                 Location/Qualifiers
misc_feature            1..2535
                        note = Description of Artificial Sequence: Synthetic
                        polynucleotide
source                  1..2535
                        mol_type = other DNA
```

```
                        organism = synthetic construct
SEQUENCE: 1
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga agatggcgat   180
gcagtgattg ttgtgtttga tgccaaagcc ccgagctttc gtcatgaagc ctatggcggc   240
tacaaagcag gtcgcgcccc gaccccggaa gattttccgc gtcagctggc cttaattaaa   300
gaattagttg acttgctggg cttagcacgt ctggaagttc cgggctatga agcagatgat   360
gttttagcct cactggccaa aaaagccgaa aagaaggct atgaagttcg cattctgacc   420
gcagataagg atctgtatca gctgctgagc gatcgtattc atgtgttaca tccggaaggc   480
tatctgatta ccccggcatg gttatgggaa aaatatggtt tacgtccgga tcagtgggca   540
gattatcgtg cactgaccgg tgacgaatca gataatctgc cgggcgttaa aggtattggt   600
gaaaaaaccg cccggaaatt attagaagaa tggggtagtc tggaagcatt actgaaaaat   660
ctggatcgcc tgaaaccggc aattcgcgaa aaaattttag cccacatgga tgacttaaaa   720
ctgtcttggg atctggccaa agtgcgtacc gatctgccgt tagaagttga ttttgccaaa   780
cgtcgcgaac cggatcgtga acgcctacga gcctttctgg aacgcttaga atttggctca   840
ctgttacatg aatttggctt actggaatct ccgaaagcat tagaagaagc cccgtggccg   900
ccgccggagta gcgcctttgt gggctttgtg ctgagtagga aagaaccgat gtgggcagac   960
ttgctggccc tggccgcagc acgcggcggt cgcgttcatc gtgccccgga accgtacaaa  1020
gccctgcgtg acctgaaaga agcacgcggc ttattagcca aagacctgag tgttctggca  1080
ttaagggaag gcttaggcct gccgccgggc gatgatccga tgctgctggc ctatctgctt  1140
gacccgagta ataccacccc ggaaggcgtt gcacgtccgt atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtgg aacgtccgct gagcgcagtg  1320
ctggcacaca tggaagccac cggtgtgcgc ttagatgttg catatctgcg tgccctgtct  1380
ctggaagttg cagaagaaat tgcacgctta gaagccgaaa tttttcgctt agcaggtcat  1440
ccgtttaact aaatagtcg cgatcagctg gaaaggggttc tgtttgatga attaggcctg  1500
ccggcaattg gcaagaccga aaaaaccggt aaacgctcta cctcagccgc agttctggaa  1560
gccctgcgcg aagcccatcc gattgttgaa aaaattttac agtatcgtga actgaccaaa  1620
ctgaaatcta cctatattga tccgttaccg gatctaattc atccgcgtac cggtcgctta  1680
catacccgtt ttaatcagac cgccaccgcc accggtcgct tatcaagtag cgatccgaac  1740
ttgcagaata ttccggtgcg taccccgtta ggtcagcgca ttcgtcgtgc ctttattgca  1800
gaagaaggtt ggttattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcacatcg cctgtcacag  2040
gaactggcaa ttccgtatga agaagcacag gcctttattg aacgctattt tcagtctttt  2100
ccgaaagttc gcgcatggat tgaaaaaacc ttagaagaag gtcgtcgtcg cggctatgtg  2160
gaaaccctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
atgaaactgg caatggttaa actgtttccg cgcctggaag aaatgggtgc acgaatgctg  2340
ttacaggttc atgatgaatt agttctgaa gccccgaaag aacgcgccga agcagttgca  2400
cgtctggcca aagaagtgat ggaaggtgtg tatccgttag cagttccgtt agaagtggaa  2460
gtgggtattg gtgaagattg gctgagcgcc aaagaaggtt ctggcagttc aggtcatcac  2520
caccatcatc actaa                                                    2535

SEQ ID NO: 2          moltype = AA  length = 844
FEATURE               Location/Qualifiers
REGION                1..844
                      note = Description of Artificial Sequence: Synthetic
                      polypeptide
source                1..844
                      mol_type = protein
                      organism = synthetic construct
SEQUENCE: 2
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 3          moltype = DNA  length = 2535
FEATURE               Location/Qualifiers
misc_feature          1..2535
                      note = Description of Artificial Sequence: Synthetic
                      polynucleotide
source                1..2535
                      mol_type = other DNA
                      organism = synthetic construct
```

```
SEQUENCE: 3
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga agatggcgat   180
gcatctattg ttgtgtttga tgccaaagcc ccgagctttc gtcatgaagc ctatggcggc   240
tacaaagcag gtcgcgcccc gaccccggaa gattttccgc gtcagctggc cttaattaaa   300
gaattagttg acttgctggg cttagcacgt ctggaagttc cgggctatga agcagatgat   360
gttttagcct cactggccaa aaaagccgaa aagaaggct atgaagttcg cattctgacc    420
gcagataagg atctgtatca gctgctgagc gatcgtattc atgtgttaca tccggaaggc   480
tatctgatta ccccggcatg gttatgggaa aaatatggtt tacgtccgga tcagtgggca   540
gattatcgtg cactgaccgg tgacgaatca gataatctgc cgggcgttaa aggtattggt   600
gaaaaaaccg cccggaaatt attagaagaa tggggtagtc tggaagcatt actgaaaaat   660
ctggatcgcc tgaaaccggc aattcgcgaa aaaattttag cccacatgga tgacttaaaa   720
ctgtcttggg atctggccaa agtgcgtacc gatctgccgt tagaagttga ttttgccaaa   780
cgtcgcgaac cggatcgtga acgcctacga gcctttctgg aacgcttaga atttggctca   840
ctgttacatg aatttggctt actggaatct ccgaaagcat tagaagaagc cccgtggccg   900
ccgccggaag gcgcctttgt gggctttgtg ctgagtagga agaaccgat gtgggcagac     960
ttgctggccc tggccgcagc acgcggcggt cgcgttcatc gtgccccgga accgtacaaa  1020
gccctgcgtg acctgaaaga agcacgcggc ttattagcca aagacctgag tgttctggca  1080
ttaagggaag gcttaggcct gccgccgggc gatgatccga tgctgctggc ctatctgctt  1140
gacccgagta ataccacccc ggaaggcgtt gcacgtcgct atggcggcga gtggaccgaa  1200
gaagcagtgg aacgtgcagc cctgtcagaa cgtctgtttg ccaatctgtg gggtcgctta  1260
gaaggcgaag aacgcttact gtggttatat cgtgaagtgg aacgtccgct gagcgcagtg  1320
ctggcacaca tggaagccac cggtgtgcgc ttagatgttg catatctgcg tgccctgtct  1380
ctggaagttg cagaagaaat tgcacgctta gaagccgaag ttttcgctt agcaggtcat   1440
ccgtttaact taaatagtcg cgatcagctg gaaagggttc tgtttgatga attaggcctg  1500
ccggcaattg caagaccga aaaaaccggt aaacgctcta cctcagccgc agttctggaa   1560
gccctgcgcg aagcccatcc cgattgttgaa aaaattttac agtatcgtga actgaccaaa  1620
ctgaaatcta cctatattga tccgttaccg gatctaattc atccgcgtac cggtcgctta  1680
catacccgtt ttaatcagac cgccaccgcc accggtcgct tatcaagtag cgatccgaat  1740
ttgcagaata ttccggtgcg taccccgtta ggtcagcgaa ttcgtcgtgc ctttattgca  1800
gaagaaggtt ggttattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatgatgtga gcgcacatcg cctgtcacag  2040
gaactggcaa ttccgtatga agaagcacag gcctttattg aacgctattt tcagtctttt  2100
ccgaaagttc gcgcatggat tgaaaaaacc ttagaagaag tcgtcgtcg cggctatgtg  2160
gaaacctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
atgaaactgg caatggttaa actgtttccg cgcctggaag aaatgggtgc acgaatgctg  2340
ttacaggttc atgatgaatt agtcctggaa gccccgaaag aacgcgccga agcagttgca  2400
cgtctggcca agaagtgat ggaagtgtg tatccgttag cagttccgtt agaagtggaa    2460
gtgggtattg gtgaagattg gctgagcgcc aaagaaggtt ctggcagttc aggtcatcac  2520
caccatcatc actaa                                                   2535
SEQ ID NO: 4          moltype = AA  length = 844
FEATURE               Location/Qualifiers
REGION                1..844
                      note = Description of Artificial Sequence: Synthetic
                      polypeptide
source                1..844
                      mol_type = protein
                      organism = synthetic construct
SEQUENCE: 4
MRGMLPLFEP KGRVLLVDGH HLAYRTFHAL KGLTTSRGEP VQAVYGFAKS LLKALKEDGD    60
ASIVVFDAKA PSFRHEAYGG YKAGRAPTPE DFPRQLALIK ELVDLLGLAR LEVPGYEADD   120
VLASLAKKAE KEGYEVRILT ADKDYQLLS DRIHVLHPEG YLITPAWLWE KYGLRPDQWA    180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 5          moltype = DNA  length = 2535
FEATURE               Location/Qualifiers
misc_feature          1..2535
                      note = Description of Artificial Sequence: Synthetic
                      polynucleotide
source                1..2535
                      mol_type = other DNA
                      organism = synthetic construct
SEQUENCE: 5
```

```
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga agatggcgat   180
gcagtgattt ctgtgtttga tgccaaagcc ccgagctttc gtcatgaagc ctatggcggc   240
tacaaagcag gtcgcgcccc gaccccggaa gattttccgc gtcagctgat cttaattaaa   300
gaattagttg acttgctggg cttagcacgt ctggaagttc cgggctatga agcagatgat   360
gttttagcct cactgccaaa aaagccgaaa aagaaggct atgaagttcg cattctgacc    420
gcagataagg atctgtatca gctgctgagc gatcgtattc atgtgttaca tccggaaggc   480
tatctgatta ccccggcatg gttatgggaa aaatatggtt tacgtccgga tcagtgggca   540
gattatcgtg cactgaccgg tgacgaatca gataatctgc cgggcgttaa aggtattggt   600
gaaaaaaccg cccggaaatt attagaagaa tggggtagtc tggaagcatt actgaaaaat   660
ctggatcgcc tgaaaccggc aattcgcgaa aaaattttag cccacatgga tgacttaaaa   720
ctgtcttggg atctggccaa agtgcgtacc gatctgccgt tagaagttga ttttgccaaa   780
cgtcgcgaac cggatcgtga acgcctacga gcctttcgtg aacgcttaga atttggctca   840
ctgttacatg aatttggctt actggaatct ccgaaagcat tagaagaagc cccgtggccg   900
ccgccggaag cgcctttgt gggctttgtg ctgagtagga agaaccgat gtgggcagac     960
ttgctggccc tggccgcagc acgcggcggt cgcgttcatc gtgccccgga accgtacaaa  1020
gccctgcgtg acctgaaaga agcacgcggc ttattagcca aagacctgag tgttctggca  1080
ttaagggaag gcttaggcct gccgccgggc gatgatccga tgctgctggc ctatctgctt  1140
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtgg aacgtccgct acgcgcagtg  1320
ctggcacaca tggaagccac cggtgtgcgc ttagatgttg catatctgcg tgccctgtct  1380
ctggaagttg cagaagaaat tgcacgctta gaagccgaag ttttttcgct tagcaggtcat  1440
ccgtttaact aaatagtcg cgatcagctg gaaagggttc tgtttgatga attaggcctg   1500
ccggcaattg gcaagaccga aaaaaccggt aaacgctcta cctcagccgc agttctggaa  1560
gccctgcgcg aagcccatcc gattgttgaa aaaattttac agtatcgtga actgaccaaa  1620
ctgaaatcta cctatattga tccgttaccg gatctaattc atccgcgtac cggtcgctta  1680
catacccgtt ttaatcagac cgccaccgcc accggtcgct tatcaagtag cgatccgaac  1740
ttgcagaata ttccggtgcg tacccgtta ggtcagcgca ttcgtcgtgc ctttattgca   1800
gaagaaggtt ggttattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcgcacatcg cctgtcacag  2040
gaactggcaa ttccgtatga agaagcacag gcctttattg aacgctattt tcagtcttt   2100
ccgaaagttc gcgcatggat tgaaaaaacc ttagaagaag tcgtcgtcg cggctatgtg   2160
gaaacctgt ttggtcgtcg tcgctatgtt ccggatctgg aagcgagagt taatcagtg    2220
cgtgaagccg ccgaacgcat ggcctttaat atgccggttc agggaacggc agctgaccttt 2280
atgaaactgg caatggttaa actgtttccg cgcctggaaa tgggtgc acgaatgctg     2340
ttacaggttc atgatgaatt agttctgaa gccccgaaag aacgcgccga agcagttgca   2400
cgtctggcca agaagtgat ggaagtgtg tatccgttag cagttccgtt agaagtggaa    2460
gtgggtattg tgaagattg gctgagcgcc aaagaaggtt ctggcagttc aggtcatcac   2520
caccatcatc actaa                                                   2535

SEQ ID NO: 6         moltype = AA  length = 844
FEATURE              Location/Qualifiers
REGION               1..844
                     note = Description of Artificial Sequence: Synthetic
                     polypeptide
source               1..844
                     mol_type = protein
                     organism = synthetic construct
SEQUENCE: 6
MRGMLPLFEP KGRVLLVDGH HLAYRTFHAL KGLTTSRGEP VQAVYGFAKS LLKALKEDGD    60
AVISVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 7         moltype = DNA  length = 2535
FEATURE              Location/Qualifiers
misc_feature         1..2535
                     note = Description of Artificial Sequence: Synthetic
                     polynucleotide
source               1..2535
                     mol_type = other DNA
                     organism = synthetic construct
SEQUENCE: 7
atgcgcggta tgctgccgtt atttgaaccg aaaggtcgtg tgctgctggt tgatggtcat    60
```

```
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaattc ccgagctttc gtcatgaagc ctatggcggc    240
tacaaagcag gtcgcgcccc gacccggaa gattttccgc gtcagctggc cttaattaaa    300
gaattagttg acttgctggg cttagcacgt ctggaagttc cgggctatga agcagatgat    360
gttttagcct cactggccaa aaaagccgaa aaagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt tacgtccgga tcagtgggca    540
gattatcgtg cactgaccgg tgacgaatca gataatctgc cgggcgttaa aggtattggt    600
gaaaaaaccg cccggaaatt attagaagaa tggggtagtc tggaagcatt actgaaaaat    660
ctggatcgcc tgaaaccggc aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actgaatct ccgaaagcat taagaagc cccgtggccg    900
ccgccggaag cgcctttgt gggctttgtg ctgagtagga agaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag gcttaggcct gccgccgggc gatgatccga tgctgctggc ctatctgctt   1140
gaccccgagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggtatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttttcgct agcaggtcat   1440
ccgtttaact aaatagtcg cgatcagctg gaaagggttc tgtttgatga attaggcctg   1500
ccggcaattg gcaagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catacccgtt ttaatcagac cgccaccgcc accggtcgct tatcaagtag cgatccgaac   1740
ttgcagaata ttccggtgcg taccccgtta ggtcagcgca ttcgtcgtgc ctttattgca   1800
gaagaaggtt ggttattagt tcattagat tatagtcaga ttgaactgcg tgttagcc    1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaaa aacgcgccga agcagttgca   2400
cgtctggcca agaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                   2535
```

SEQ ID NO: 8          moltype = AA   length = 844
FEATURE               Location/Qualifiers
REGION                1..844
                      note = Description of Artificial Sequence: Synthetic
                       polypeptide
source                1..844
                      mol_type = protein
                      organism = synthetic construct
SEQUENCE: 8
```
MRGMLPLFEP KGRVLLVDGH HLAYRTFHAL KGLTTSRGEP VQAVYGFAKS LLKALKEDGD    60
AVIVVFDAKF PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                               844
```

SEQ ID NO: 9          moltype = DNA   length = 2535
FEATURE               Location/Qualifiers
misc_feature          1..2535
                      note = Description of Artificial Sequence: Synthetic
                       polynucleotide
source                1..2535
                      mol_type = other DNA
                      organism = synthetic construct
SEQUENCE: 9
```
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
```

```
gttcaggcag tgtatggttt tgccaaatca ctgctgaaag cattaaaaga agatggcgat    180
gcagtgattg ttgtgtttga tgccaaagcc ccgagcgctc gtcatgaagc ctatggcggc    240
tacaaagcag gtcgcgcccc gaccccggaa gattttccgc gtcagctggc cttaattaaa    300
gaattagttg acttgctggg cttagcacgt ctggaagttc cgggctatga agcagatgat    360
gttttagcct cactggccaa aaaagccgaa aagaaggct atgaagttcg cattctgacc    420
gcagataagg atctgtatca gctgctgagc gatcgtattc atgtgttaca tccggaaggc    480
tatctgatta ccccggcatg gttatggaa aaatatggtt tacgtccgga tcagtgggca    540
gattatcgtg cactgaccgg tgacgaatca gataatctgc cgggcgttaa aggtattggt    600
gaaaaaaccg cccggaaatt attagaagaa tggggtagtc tggaagcatt actgaaaaat    660
ctggatcgcc tgaaaccggc aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtagga aagaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagaccgag tgttctggca   1080
ttaagggaag cttaggcct gccgccgggc gatgatccga tgctgctggc ctatctgctt   1140
gacccgagta ataccacccc ggaaggcgtt gcacgtccgt atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgtaa tttttcgctt agcaggtcat   1440
ccgtttaact aaatagtcg cgatcagctg gaaaggggtc tgttttgatga attaggcctg   1500
ccggcaattg gcaagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac ggtcgctta   1680
catacccgtt ttaatcagac cgccaccgcc accggtcgct tatcaagtag cgatccgaac   1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcgatg   2220
cgtgaagccg ccgaacgcat ggcctttaat atgccggttc agggaacggc agctgaccttt  2280
atgaaactgg caatggttaa actgtttccg cgcctgaag aaatgggtgc acgaatgctg   2340
ttacaggttc atgatgaatt agttctgaa gccccgaaag aacgcgccga gcagttgca   2400
cgtctggcca aagaagtgat ggaagtgtg tatccgttag cagttccgtt agaagtggaa   2460
gtgggtattg gtgaagattg gctgagcgcc aaagaaggtt ctggcagttc aggtcatcac   2520
caccatcatc actaa                                                    2535

SEQ ID NO: 10          moltype = AA   length = 844
FEATURE                Location/Qualifiers
REGION                 1..844
                       note = Description of Artificial Sequence: Synthetic
                       polypeptide
source                 1..844
                       mol_type = protein
                       organism = synthetic construct
SEQUENCE: 10
MRGMLPLFEP KGRVLLVDGH HLAYRTFHAL KGLTTSRGEP VQAVYGFAKS LLKALKEDGD    60
AVIVVFDAKA PSARHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 11          moltype = DNA   length = 2535
FEATURE                Location/Qualifiers
misc_feature           1..2535
                       note = Description of Artificial Sequence: Synthetic
                       polynucleotide
source                 1..2535
                       mol_type = other DNA
                       organism = synthetic construct
SEQUENCE: 11
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
```

```
gcagtgattg ttgtgtttga tgccaaagcc ccgagctttc gtcatgaatt ctatggcggc    240
tacaaagcag gtcgcgcccc gacccggaa gattttccgc gtcagctggc cttaattaaa     300
gaattagttg acttgctggg cttagcacgt ctggaagttc gggctatga agcagatgat     360
gttttagcct cactggccaa aaaagccgaa aaagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt tacgtccgga tcagtgggca    540
gattatcgtg cactgaccgg tgacgaatca gataatctgc cgggcgttaa aggtattggt    600
gaaaaaaccg cccggaaatt attagaagaa tggggtagtc tggaagcatt actgaaaaat    660
ctggatcgcc tgaaaccggc aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtagga agaaccgat gtgggcagac     960
ttgctggccc tggccgcagc acgcggcggt cgcgttcatc gtgccccgga accgtacaaa   1020
gccctgcgcg acctgaaaga agcacgcggc ttattagcca aagacctgag tgttctggca   1080
ttaagggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcagcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttttcgctt agcaggtcat   1440
ccgttttaact taaatagtcg cgatcagctg gaaagggttc tgtttgatga attaggcctg   1500
ccggcaattg gcaagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg atctaattc atccgcgtac cggtcgctta   1680
cataccccgtt ttaatcagac cgccaccgcc accggtcgct tatcaagtag cgatccgaac   1740
ttgcagaata ttccggtgcg tacccccgtta ggtcagcgaa ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctc tatggtatga gccacatcg cctgtcacag   2040
gaactggcaa ttccgtatga agaagcacag gcctttattg aacgctattt tcagtctttt   2100
ccgaaagttc gcgcatggat tgaaaaaacc ttagaagaag tcgtcgtcg cggctatgtg   2160
gaaaccctgt ttggtcgtcg tcgctatgtt ccggatctgg aagcgagagt taaatcagtg   2220
cgtgaagcg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctgaa gcccgaaag aacgcgccga agcagttgca   2400
cgtctggcca aagaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                    2535

SEQ ID NO: 12           moltype = AA   length = 844
FEATURE                 Location/Qualifiers
REGION                  1..844
                        note = Description of Artificial Sequence: Synthetic
                        polypeptide
source                  1..844
                        mol_type = protein
                        organism = synthetic construct
SEQUENCE: 12
MRGMLPLFEP KGRVLLVDGH HLAYRTFHAL KGLTTSRGEP VQAVYGFAKS LLKALKEDGD    60
AVIVVFDAKA PSFRHEFYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 13           moltype = DNA   length = 2535
FEATURE                 Location/Qualifiers
misc_feature            1..2535
                        note = Description of Artificial Sequence: Synthetic
                        polynucleotide
source                  1..2535
                        mol_type = other DNA
                        organism = synthetic construct
SEQUENCE: 13
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
```

```
tacaaagcag gtcgcgcccc gaccccggaa gattttccgc gtcagctggc cttaattaaa    300
gaattagttg acttgctggg cttagcacgt ctggaagttc cgggctatga agcagatgat    360
gttttagcct cactggccaa aaaagccgaa aagaaggct atgaagttcg cattctgacc     420
gcagataagg atctgtatca gctgctgagc gatcgtattc atgtgttaca tccggaaggc    480
tatctgatta ccccggcatg gttatgggaa aaatatggct tacgtccgga tcagtgggca    540
gattatcgtg cactgaccgg tgacgaatca gataatctgc cgggcgttaa aggtattggt    600
gaaaaaaccg cccggaaatt attagaagaa tggggtagtc tggaagcatt actgaaaaat    660
ctggatcgcc tgaaaccggc aattcgcgaa aaaattttag cccacatgga tgacttaaaa    720
ctgtcttggg atctggccaa aagtgcgtacc gatctggggt tagaagttga ttttgccaaa   780
cgtcgcgaac cggatcgtga acgcctacga gcctttctgg aacgcttaga atttggctca    840
ctgttacatg aatttggctt actggaatcc cgaaagcat tagaagaagc cccgtggccg     900
ccgccggaag cgcctttgt gggctttgtg ctgagtagga agaaccgat gtgggcagac      960
ttgctggccc tggccgcagc acgcggcggt cgcgttcatc gtgccccgga accgtacaaa   1020
gccctgcgtg aacctgaaaga agcacgcggc ttattagcca aagacctgag tgttctggca   1080
ttaagggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct actgcgcagtg  1320
ctggcacaca tggaagccac cggtgtgcgc ttagatgttg catatctgcg tgccctgtct   1380
ctggaagttg cagaagaaat tgcacgctta gaagccgaag ttttcgctt agcaggtcat    1440
ccgtttaact aaatagtcg cgatcagctg aaagggttc tgtttgatga attaggcctg     1500
ccggcaattg gcaagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catcccgtt ttaatcagac cgccaccgcc accggtcgct tatcaagtag cgatccgaac   1740
ttgcagaata ttccggtgcg tacccccgtta ggtcagcgca ttcgtcgtgc ctttattgca  1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgcct   2340
ttacaggttc atgatgaatt agttctggaa gccccgaaag aacgcgccga agcagttgca   2400
cgtctggcca aagaagtgat ggaaggtgtg tatccgttag cagttccgtt agaagtggaa   2460
gtgggtattg tgaagattg gctgagcgcc aagaaggtt ctggcagttc aggtcatcac    2520
caccatcatc actaa                                                   2535

SEQ ID NO: 14          moltype = AA   length = 844
FEATURE                Location/Qualifiers
REGION                 1..844
                       note = Description of Artificial Sequence: Synthetic
                       polypeptide
source                 1..844
                       mol_type = protein
                       organism = synthetic construct
SEQUENCE: 14
MRGMLPLFEP KGRVLLVDGH HLAYRTFHAL KGLTTSRGEP VQAVYGFAKS LLKALKEDGD     60
AVIVVFDAKA PSFRHEAYGG YKAGRAPTPE DFPRQLALIK ELVDLLGLAR LEVPGYEADD    120
VLASLAKKAE KEGYEVRILT ADKDLYQLLS DRIHVLHPEG YLITPAWLWE KYGLRPDQWA    180
DYRALTGDES DNLPGVKGIG EKTARKLLEE WGSLEALLKN LDRLKPAIRE KILAHMDDLK    240
LSWDLAKVRT DLGLEVDFAK RREPDRERLR AFLERLEFGS LLHEFGLLES PKALEEAPWP    300
PPEGAFVGFV LSRKEPMWAD LLALAAARGG RVHRAPEPYK ALRDLKEARG LLAKDLSVLA    360
LREGLGLPPG DDPMLLAYLL DPSNTTPEGV ARRYGGEWTE EAGERAALSE RLFANLWGRL    420
EGEERLLWLY REVERPLSAV LAHMEATGVR LDVAYLRALS LEVAEEIARL EAEVFRLAGH    480
PFNLNSRDQL ERVLFDELGL PAIGKTEKTG KRSTSAAVLE ALREAHPIVE KILQYRELTK    540
LKSTYIDPLP DLIHPRTGRL HTRFNQTATA TGRLSSSDPN LQNIPVRTPL GQRIRRAFIA    600
EEGWLLVALD YSQIELRVLA HLSGDENLIR VFQEGRDIHT ETASWMFGVP REAVDPLMRR    660
AAKTINFGVL YGMSAHRLSQ ELAIPYEEAQ AFIERYFQSF PKVRAWIEKT LEEGRRRGYV    720
ETLFGRRRYV PDLEARVKSV REAAERMAFN MPVQGTAADL MKLAMVKLFP RLEEMGARML    780
LQVHDELVLE APKERAEAVA RLAKEVMEGV YPLAVPLEVE VGIGEDWLSA KEGSGSSGHH    840
HHHH                                                                844

SEQ ID NO: 15          moltype = DNA   length = 2535
FEATURE                Location/Qualifiers
misc_feature           1..2535
                       note = Description of Artificial Sequence: Synthetic
                       polynucleotide
source                 1..2535
                       mol_type = other DNA
                       organism = synthetic construct
SEQUENCE: 15
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag gtcgcgcccc gaccccggaa gattttccgc gtcagctggc cttaattaaa    300
```

```
gaattagttg acttgctggg cttagcacgt ctggaagttc cgggctatga agcagatgat   360
gttttagcct cactgtgccaa aaaagccgaa aaagaaggct atgaagttcg cattctgacc   420
gcagataagg atctgtatca gctgctgagc gatcgtattc atgtgttaca tccgaaggc    480
tatctgatta ccccggcatg gttatgggaa aaatatggtt acgtccgga tcagtgggca    540
gattatcgtg cactgaccgg tgacgaatca gataatctgc cgggcgttaa aggtattggt   600
gaaaaaaccg cccggaaatt attagaagaa tggggtagtc tggaagcatt actgaaaaat   660
ctggatcgcc tgaaaccggc aattcgcgaa aaaattttag cccacatgga tgacttaaaa   720
ctgtcttggg atctggccaa agtgcgtacc gatctgccgt taaaagttga ttttgccaaa   780
cgtcgcgaac cggatcgtga acgcctacga gcctttctgg aacgcttaga atttggctca   840
ctgttacatg aatttggctt actgactct ccgaaagcat tagaagaagc cccgtggcca   900
ccgccggaag cgcctttgt gggctttgtg ctgagtagga agaaccgat gtgggcagac    960
ttgctggccc tggccgcagc acgcggcggt cgcgttcatc gtgccccgga accgtacaaa  1020
gccctgcgtg acctgaaaga agcacgcggc ttattagcca aagacctgag tgttctggca  1080
ttaagggaag gcttaggcct gccgccgggc gatgatccga tgctgctggc ctatctgctt  1140
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtgg aacgtccgct gagcgcagtg  1320
ctggcacaca tggaagccac cggtgtgcgc ttagatcgtg catatctgcg tgccctgtct  1380
ctggaagttg cagaagaaat tgcacgctta gaagccgaag ttttcgctt agcaggtcat  1440
ccgttaact aaatagtcg cgatcagctg gaaagggttc tgtttgatga attaggcctg  1500
ccggcaattg gcaagaccga aaaaaccggt aaacgctcta cctcagccgc agttctggaa  1560
gccctgcgcg aagcccatcc gattgttgaa aaaatttac agtatcgtga actgaccaaa  1620
ctgaaatcta cctatattga tccgttaccg gatctaattc atccgcgtac cggtcgctta  1680
cataccccgtt ttaatcagac cgccaccgcc accggtcgct tatcaagtag cgatccgaac  1740
ttgcagaata ttccggtgcg taccccgtta ggtcagcgca ttcgtcgtgc ctttattgca  1800
gaagaaggtt ggttattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcgcacatcg cctgtcacag  2040
gaactgcaa ttccgtatga agaagcacag gcctttattt aacgctattt tcagtctttt  2100
ccgaaagttc gcgcatggat tgaaaaaacc ttagaagaag gtcgtcgtcg cggctatgtg  2160
gaaaccctgt ttggtcgtcg tcgctatgtt ccggatctgg aagcgagagt taatcagtg   2220
cgtgaagccg ccgaacgcat ggcctttaat atgccggttc agggaacggc agctgacctt  2280
atgaaactgg caatggttaa actgtttccg cgcctggaaa aaatgggtgc acgaatgctg  2340
ttacaggttc atgatgaatt agttctggaa gccccgaaag aacgcgccga agcagttgca  2400
cgtctggcca aagaagtgat ggaaggtgtg tatccgttag cagttccgtt agaagtggaa  2460
gtgggtattg gtgaagattg gctgagcgcc aaagaaggtt ctggcagttc aggtcatcac  2520
caccatcatc actaa                                                   2535

SEQ ID NO: 16         moltype = AA   length = 844
FEATURE               Location/Qualifiers
REGION                1..844
                      note = Description of Artificial Sequence: Synthetic
                       polypeptide
source                1..844
                      mol_type = protein
                      organism = synthetic construct
SEQUENCE: 16
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLKVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                               844

SEQ ID NO: 17         moltype = DNA   length = 2535
FEATURE               Location/Qualifiers
misc_feature          1..2535
                      note = Description of Artificial Sequence: Synthetic
                       polynucleotide
source                1..2535
                      mol_type = other DNA
                      organism = synthetic construct
SEQUENCE: 17
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga agatggcgat   180
gcagtgattg ttgtgtttga tgccaaagcc ccgagctttc gtcatgaagc ctatggcggc   240
tacaaagcag gtcgcgcccc gacccccgaa gattttccgc gtcagctggc cttaattaaa   300
gaattagttg acttgctggg cttagcacgt ctggaagttc cgggctatga agcagatgat   360
```

-continued

```
gttttagcct cactggccaa aaaagccgaa aaagaaggct atgaagttcg cattctgacc    420
gcagataagg atctgtatca gctgctgagc gatcgtattc atgtgttaca tccggaaggc    480
tatctgatta ccccggcatg gttatgggaa aatatggtt tacgtccgga tcagtgggca    540
gattatcgtg cactgaccgg tgacgaatca gataatctgc cggcgttaa aggtattggt    600
gaaaaaaccg cccggaaatt attagaagaa tggggtactc tggaagcatt actgaaaaat    660
ctggatcgcc tgaaaccggc aattcgcgaa aaaattttag cccacatgga tgacttaaaa    720
ctgtcttggg atctggccaa agtgcgtacc gatctgccgt tagaagttcg ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag cgcctttgt gggctttgtg ctgagtagga agaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag cttaggcct gccgccgggc gatgatccga tgctgctggc ctatctgctt   1140
gacccgagta ataccacccc ggaaggcgtt gcacgtcgca atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaaa ttttcgctt agcaggtcat   1440
ccgtttaact aaatagtcg cgatcagctg gaaagggttc tgtttgatga attaggcctg   1500
ccggcaattg gcaagaccga aaaaaccggt aaacgctcta cctcagccgc agttctggaa   1560
gccctgcgcg aagcccatcc gattgttgaa aaattttac agtatcgtga actgaccaaa   1620
ctgaaatcta cctatattga tccgttaccg gatctaattc atccgcgtac cggtcgctta   1680
catcccgtt taatcagac cgccaccgcc accggtcgct tatcaagtag cgatccgaac   1740
ttgcagaata ttccggtgcg tacccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctgaaag aaatgggtgc acgaatgctg   2340
ttacaggttc atgatgaatt agttctgaa gccccgaaaa aacgcgccga agcagttgca   2400
cgtctggcca aagaagtgat ggaagtgtg tatccgttag cagttccgtt agaagtggaa   2460
gtgggtattg gtgaagattg gctgagcgcc aaagaaggtt ctggcagttc aggtcatcac   2520
caccatcatc actaa                                                   2535
```

SEQ ID NO: 18          moltype = AA   length = 844
FEATURE                Location/Qualifiers
REGION                 1..844
                       note = Description of Artificial Sequence: Synthetic
                       polypeptide
source                 1..844
                       mol_type = protein
                       organism = synthetic construct
SEQUENCE: 18
```
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVRFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844
```

SEQ ID NO: 19          moltype = DNA   length = 2535
FEATURE                Location/Qualifiers
misc_feature           1..2535
                       note = Description of Artificial Sequence: Synthetic
                       polynucleotide
source                 1..2535
                       mol_type = other DNA
                       organism = synthetic construct
SEQUENCE: 19
```
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga agatggcgat   180
gcagtgattg ttgtgtttga tgccaaagcc ccgagctttc gtcatgaagc ctatggcggc   240
tacaaagcag gtcgcgcccc gaccccggaa gattttccgc gtcagctggc cttaattaaa   300
gaattagttg acttgctggg cttagcacgt ctggaagttc cgggctatga agcagatgat   360
gttttagcct cactggccaa aaaagccgaa aaagaaggct atgaagttcg cattctgacc   420
```

```
gcagataagg atctgtatca gctgctgagc gatcgtattc atgtgttaca tccggaaggc  480
tatctgatta cccggcatg  gttatggaa  aaatatggtt tacgtccgga tcagtgggca  540
gattatcgtg cactgaccgg tgacgaatca gataatctgc cgggcgttaa aggtattggt  600
gaaaaaaccg cccggaaatt attagaagaa tggggtagtc tggaagcatt actgaaaaat  660
ctggatcgcc tgaaaccggc aattcgcgaa aaaattttag cccacatgga tgacttaaaa  720
ctgtcttggg atctgccaa  agtgcgtacc gatctgccgt tagaagttga ttttttcaaa  780
cgtcgcgaac cggatcgtga acgcctacga gcctttctgg aacgcttaga atttggctca  840
ctgttacatg aatttggctt actggaatct ccgaaagcat tagaagaagc cccgtggccg  900
ccgccggaag gcgcctttgt gggctttgtg ctgagtagga aagaaccgat gtgggcagac  960
ttgctggccc tggccgcagc acgcggcggt cgcgttcatc gtgccccgga accgtacaaa 1020
gccctgcgcg acctgaaaga agcacgcggc ttattagcca aagacctgag tgttctggca 1080
ttaagggaag gcttaggcct gccgccgggc gatgatccga tgctgctggc ctatctgctt 1140
gacccgagta ataccacccc ggaaggcgtt gcacgtcgct atggcggcga gtggaccgaa 1200
gaagcaggcg aacgtgcagc cctgtcagaa cgtctgtttg ccaatctgtg gggtcgctta 1260
gaaggcgaag aacgcttact gtggttatat cgtgaagtgg aacgtccgct gagcgcagtg 1320
ctggcacaca tggaagccac cggtgtgcgc ttagatgttg catatctgcg tgccctgtct 1380
ctggaagttg cagaagaaat tgcacgctta gaagccgaag ttttccgctt agcaggtcat 1440
ccgtttaact taaatagtcg cgatcagctg gaaagggttc tgtttgatga attaggcctg 1500
ccggcaattg gcaagaccga aaaaaccggt aaacgctcta cctcagccgc agttctggaa 1560
gccctgcgcg aagcccatcc gattgttgaa aaaattttac agtatcgtga actgaccaaa 1620
ctgaaatcta cctatattga tccgttaccg gatctaattc atccgcgtac cggtcgctta 1680
catacccgtt ttaatcagac cgccaccgcc accggtcgct tatcaagtag cgatccgaat 1740
ttgcagaata ttccggtgcg tacccccgtta ggtcagcgca ttcgtcgtgc ctttattgca 1800
gaagaaggtt ggttattagt tgcattagat tatagtcaga ttgaactgcg tgtgttagcc 1860
catctgagcg gcgacgaaaa tctgattcgt gtgtttcagg aaggtcgcga tattcatacc 1920
gaaaccgcct cttggatgtt tggtgttccg cgcgaagcag ttgatccgtt aatgcgccgt 1980
gcagccaaaa ccattaattt tggtgtgctg tatggatga  gcacatcg   cctgtcacag 2040
gaactggcaa ttccgtatga agaagcacag gcctttattg aacgctattt tcagtctttt 2100
ccgaaagttc gcgcatggat tgaaaaaacc ttagaagaag tcgtcgtcg  cggctatgtg 2160
gaaacccctgt ttggtcgtcg tcgctatgtt ccggatctgg aagcgagagt taaatcagtg 2220
cgtgaagccg ccgaacgcat ggcctttaat atgccggttc agggaacggc agctgacctt 2280
atgaaactgg caatggttaa actgtttccg cgcctggaag aaatgggtgc acgaatgctg 2340
ttacaggttc atgatgaatt agttctgaa  gccccgaaag aacgcgccga agcagttgca 2400
cgtctggcca aagaagtgat ggaaggtgtg tatccgttag cagttccgtt agaagtggaa 2460
gtgggtattg gtgaagattg gctgagcgcc aagaaggtt  ctggcagttc aggtcatcac 2520
caccatcatc actaa                                                   2535

SEQ ID NO: 20         moltype = AA   length = 844
FEATURE               Location/Qualifiers
REGION                1..844
                      note = Description of Artificial Sequence: Synthetic
                      polypeptide
source                1..844
                      mol_type = protein
                      organism = synthetic construct
SEQUENCE: 20
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHVLHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFFK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLLAYLL DPSNTTPEGV ARRYGGEWTE EAGERAALSE RLFANLWGRL  420
EGEERLLWLY REVERPLSAV LAHMEATGVR LDVAYLRALS LEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PDLEARVKSV REAAERMAFN MPVQGTAADL MKLAMVKLFP RLEEMGARML  780
LQVHDELVLE APKERAEAVA RLAKEVMEGV YPLAVPLEVE VGIGEDWLSA KEGSGSSGHH  840
HHHH                                                               844

SEQ ID NO: 21         moltype = DNA  length = 2535
FEATURE               Location/Qualifiers
misc_feature          1..2535
                      note = Description of Artificial Sequence: Synthetic
                      polynucleotide
source                1..2535
                      mol_type = other DNA
                      organism = synthetic construct
SEQUENCE: 21
atgcgcggta tgctgccgtt atttgaaccg aaaggtcgtg tgctgctggt tgatggtcat   60
cacttagcat atcgtacctt tcatgccctg aaaggcctga ccacctctcg cggcgaaccg  120
gttcaggcag tgtatggttt tgccaaatca ctgctgaaag cattaaaaga agatggcgat  180
gcagtgattg ttgtgtttga tgccaaagcc ccgagctttc gtcatgaagc ctatggcggc  240
tacaaagcag gtcgcgcccc cgaccccgaa gattttccgc gtcagctggc cttaattaaa  300
gaattagttg acttgctggg cttagcacgt ctggaagttc cgggctatga agcagatgat  360
gttttagcct cactggccaa aaaagccgaa aagaaaggct atgaagttcg cattctgacc  420
gcagataagg atctgtatca gctgctgagc gatcgtattc atgtgttaca tccggaaggc  480
```

```
tatctgatta ccccggcatg gttatgggaa aaatatggtt tacgtccgga tcagtgggca    540
gattatcgtg cactgaccgg tgacgaatca gataatctgc cgggcgttaa aggtattggt    600
gaaaaaaccg cccggaaatt attagaagaa tggggtagtc tggaagcatt actgaaaaat    660
ctggatcgcc tgaaaccggc aattcgcgaa aaaattttag cccacatgga tgacttaaaa    720
ctgtcttggg atctggccaa agtgcgtacc gatctgcccgt tagaagttga ttttgccaaa    780
cgtcgcgaac cggatcgtga acgcctacga ttctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtagga agaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgtc actgcgcagtg   1320
ctggcacaca tggaagccac cggtgtgcgc ttagatgttg catatctgcg tgccctgtct   1380
ctggaagttg cagaagaaat tgcacgctta gaagccgaag tttttcgctt agcaggtcat   1440
ccgtttaact aaatagtcg cgatcagctg aaagggttc tgtttgatga attaggcctg   1500
ccggcaattg gcaagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catacccgtt ttaatcagac cgccaccgcc accggtcgct tatcaagtag cgatccgaac   1740
ttgcagaata ttccggtgcg taccccgtta ggtcagcgca ttcgtcgtgc cttttattga   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag tcgtcgtcg cggctatgtg   2160
gaaaccctgt ttggtcgtcg tcgctatgtt ccggatctgg aagcgagagt taatcagtg   2220
cgtgaagccg ccgaacgcat ggcctttaat atgccggttc agggaacggc agctgacctt   2280
atgaaactgg caatggttaa actgtttccg cgcctggaag aaatggtgc acgaatgctg   2340
ttacaggttc atgatgaatt agttctggaa gccccgaaag aacgcgccga agcagttgca   2400
cgtctggcca agaagtgat ggaaggtgtg tatccgttag cagttccgtt agaagtggaa   2460
gtgggtattg tgaagattg gctgagcgcc aagaaggtt ctggcagttc aggtcatcac   2520
caccatcatc actaa                                                    2535

SEQ ID NO: 22           moltype = AA   length = 844
FEATURE                 Location/Qualifiers
REGION                  1..844
                        note = Description of Artificial Sequence: Synthetic
                        polypeptide
source                  1..844
                        mol_type = protein
                        organism = synthetic construct
SEQUENCE: 22
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR FFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 23           moltype = DNA   length = 2535
FEATURE                 Location/Qualifiers
misc_feature            1..2535
                        note = Description of Artificial Sequence: Synthetic
                        polynucleotide
source                  1..2535
                        mol_type = other DNA
                        organism = synthetic construct
SEQUENCE: 23
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg tggtgtttga tgccaaagcc ccgagcttc gtcatgaagc ctatggcggc    240
tacaaagcag gtcgcgcccc gaccccggaa gattttccgc gtcagctggc cttaattaaa    300
gaattagttg acttgctggg cttagcacgt ctggaagttc cgggctatga agcagatgat    360
gttttagcct cactggccaa aaaagccgaa aagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt tacgtccgga tcagtgggca    540
```

-continued

```
gattatcgtg cactgaccgg tgacgaatca gataatctgc cgggcgttaa aggtattggt    600
gaaaaaaccg cccggaaatt attagaagaa tgggggtagtc tggaagcatt actgaaaaat   660
ctggatcgcc tgaaaccggc aattcgcgaa aaaattttag cccacatgga tgacttaaaa   720
ctgtcttggg atctggccaa agtgcgtacc gatctgccgt tagaagttga ttttgccaaa   780
cgtcgcgaac cggatcgtga acgccctacga gcctttcgtg aacgcttaga atttggctca   840
ctgttacatg aatttggctt atctgaatct ccgaaagcat tagaagaagc cccgtggccg   900
ccgccggaag cgcctttgt gggctttgt ctgagtagga agaaccgat gtgggcagac      960
ttgctggccc tggccgcagc acgcggcggt cgcgttcatc gtgccccgga accgtacaaa  1020
gccctgcgtg acctgaaaga agcacgcggc ttattagcaa aagacctgag tgttctggca  1080
ttaagggaag gcttaggcct gccgccgggc gatgatccga tgctgctggc ctatctgctt  1140
gacccgagta ataccacccc ggaaggcgtt gcacgtcgct atggcggcga gtggaccgaa  1200
gaagcaggca acgtgcagc cctgtcagaa cgtctgtttg ccaatctgtg gggtcgctta  1260
gaaggcgaag aacgcttact gtggttatat cgtgaagtgg aacgtccgct gagcgcagtg  1320
ctggcacaca tggaagccac cggtgtgcgc ttagatgttg catatctgcg tgccctgtct  1380
ctggaagttg cagaagaaat tgcacgctta gaagccgaag ttttttcgctt agcaggtcat  1440
ccgtttaact aaatagtcg cgatcagctg gaaagggttc tgtttgatga attaggcctg  1500
ccggcaattg gcaagaccga aaaaaccggt aaacgctcta cctcagccgc agttctggaa  1560
gccctgcgcg aagcccatcc gattgttgaa aaaattttac agtatcgtga actgaccaaa  1620
ctgaaatcta cctatattga tccgttaccg gatctaattc atccgcgtac cggtcgctta  1680
catacccgtt ttaatcagac cgccaccgcc accggtcgct tatcaagtag cgatccgaac  1740
ttgcagaata ttccggtgcg taccccgtta ggtcagcgca ttcgtcgtgc ctttattgca  1800
gaagaaggtt ggttattagt tgcattagat tatagtcaga ttgaactgtg tgttagcc    1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcgcacatcg cctgtcacag  2040
gaactgcaa ttccgtatga agaagcacag gcctttattg aacgctattt tcagtcttt   2100
ccgaaagttc gcgcatggat tgaaaaaacc ttagaagaag gtcgtcgtcg cggctatgtg  2160
gaaaccctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
atgaaactgg caatggttaa actgtttccg cgcctggaaa aaatgggtgc acgaatgctg  2340
ttacaggttc atgatgaatt agttctggaa gccccgaaaa aacgcgccga agcagttgca  2400
cgtctggcca agaagtgat ggaaggtgtg tatccgttag cagttccgtt agaagtggaa  2460
gtgggtattg gtgaagattg gctgagcgcc aagaaaggtt ctggcagttc aggtcatcac  2520
caccatcatc actaa                                                   2535
```

```
SEQ ID NO: 24           moltype = AA  length = 844
FEATURE                 Location/Qualifiers
REGION                  1..844
                        note = Description of Artificial Sequence: Synthetic
                         polypeptide
source                  1..844
                        mol_type = protein
                        organism = synthetic construct
SEQUENCE: 24
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLSES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844
```

```
SEQ ID NO: 25           moltype = DNA  length = 2535
FEATURE                 Location/Qualifiers
misc_feature            1..2535
                        note = Description of Artificial Sequence: Synthetic
                         polynucleotide
source                  1..2535
                        mol_type = other DNA
                        organism = synthetic construct
SEQUENCE: 25
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga gatggcgat    180
gcagtgattg ttgtgtttga tgccaaagcc ccgagctttc gtcatgaagc ctatggcggc   240
tacaaagcag gtcgcgcccc gaccccggaa gatttccgc gtcagctggc cttaattaaa   300
gaattagttg acttgctggg cttagcacgt ctggaagttc cgggctatga agcagatgat   360
gttttagcct cactgccaa aaaagccgaa aaagaaggct atgaagttcg cattctgacc   420
gcagataagg atctgtatca gctgctgagc gatcgtattc atgtgttaca tccggaaggc   480
tatctgatta ccccggcatg gttatgggaa aaatatggtt acgtccgga tcagtgggca   540
gattatcgtg cactgaccgg tgacgaatca gataatctgc cgggcgttaa aggtattggt   600
```

```
gaaaaaaccg cccggaaatt attagaagaa tggggtagtc tggaagcatt actgaaaaat  660
ctggatcgcc tgaaaccggc aattcgcgaa aaaattttag cccacatgga tgacttaaaa  720
ctgtcttggg atctggccaa agtgcgtacc gatctgccgt tagaagttga ttttgccaaa  780
cgtcgcgaac cggatcgtga acgcctacga gcctttctgg aacgcttaga atttggctca  840
ctgttacatg aatttggctt actgaaatct ccgaaagcat tagaagaagc cccgtggccg  900
ccgccggaag gcgcctttgt gggctttgtg ctgagtagga agaaccgat gtgggcagac  960
ttgctggccc tggccgcagc acgcggcggt cgcgttcatc gtgccccgga accgtacaaa 1020
gccctgcgtg acctgaaaga agcacgcggc ttattagcca aagacctgag tgttctggca 1080
ttaagggaag gcttaggcct gccgccgggc gatgatccga tgctgctggc ctatctgctt 1140
gacccgagta ataccacccc ggaaggcgtt gcacgtcgct atggcggcga gtggaccgaa 1200
gaagcaggcg aacgtgcagc cctgtcagaa cgtctgtttg ccaatctgtg gggtcgctta 1260
gaaggcgaag aacgcttact gtggttatat cgtgaagtgg aacgtccgct gagcgcagtg 1320
ctggcacaca tggaagccac cggtgtgcgc ttagatgttg catatctgcg tgccctgtct 1380
ctggaagttg cagaagaaat tgcacgctta gaagccgaaa ttgccgtacc cggtcgctta 1440
ccgtttaact aaatagtcg cgatcagctg gaaagggttc tgtttgatga attaggcctg 1500
ccggcaattg caagaccga aaaaaccggt aaacgctcta cctcagccgc agttctggaa 1560
gccctgcgcg aagcccatcc gattgttgaa aaattttac agtatcgtga actgaccaaa 1620
ctgaaatcta cctatattga tccgttaccg gatcaattca atccgcgtac cggtcgctta 1680
catacccgtt ttaatcagac cgccaccgcc accggtcgct atcaagtag cgatccgaac 1740
ttgcagaata ttccggtgcg taccccgtta ggtcagcgca ttcgtcgtgc ctttattgca 1800
gaagaaggtt ggttattagt tgcattagat tatagtcaga ttgaactgcg tgtgttagcc 1860
catctgagcg gcgacgaaaa tctgattcgt gtgtttcagg aaggtcgcga tattcatacc 1920
gaaaccgcct cttggatgtt tggtgttccg cgcgaagcag ttgatccgtt aatgcgccgt 1980
gcagccaaaa ccattaattt tggtgtgctg tatggtatga gcgcacatcg cctgtcacag 2040
gaactggcaa ttccgtatga agaagcacag gcctttattg aacgctattt tcagtctttt 2100
ccgaaagttc gcgcatggat tgaaaaaacc ttagaagaag gtcgtcgtcg cggctatgtg 2160
gaaaccctgt ttggtcgtcg tcgctatgtt ccggatctgg aagcgagagt taaatcagtg 2220
cgtgaagccg ccgaacgcat ggcctttaat atgccggttc agggaacggc agctgacctt 2280
atgaaactgg caatggttaa actgtttccg cgcctgaag aaatgggtgc acgaatgctg 2340
ttacaggttc atgatgaatt agttctggaa gccccgaaag aacgcgccga agcagttgaa 2400
cgtctggcca aagaagtgat ggaaggtgtg tatccgttag cagttcctt agaagtggaa 2460
gtgggtattg gtgaagattg gctgagcgcc aaagaaggtt ctggcagttc aggtcatcac 2520
caccatcatc actaa                                                2535

SEQ ID NO: 26          moltype = AA   length = 844
FEATURE                Location/Qualifiers
REGION                 1..844
                       note = Description of Artificial Sequence: Synthetic
                        polypeptide
source                 1..844
                       mol_type = protein
                       organism = synthetic construct
SEQUENCE: 26
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLKS PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                               844

SEQ ID NO: 27          moltype = DNA   length = 2535
FEATURE                Location/Qualifiers
misc_feature           1..2535
                       note = Description of Artificial Sequence: Synthetic
                        polynucleotide
source                 1..2535
                       mol_type = other DNA
                       organism = synthetic construct
SEQUENCE: 27
atgcgcggta tgctgccgtt atttgaaccg aaaggtcgtg tgctgctggt tgatggtcat   60
cacttagcat atcgtacctt tcatgccctg aaaggcctga ccacctctcg cggcgaaccg  120
gttcaggcag tgtatggttt tgccaaatca ctgctgaaag cattaaaaga gatggcgat   180
gcagtgattg ttgtgtttga tgccaaagcc ccgagctttc gtcatgaagc ctatggcggc  240
tacaaagcag gtcgcgcccc gaccccggaa gattttcgc gtcagctggc cttaattaaa  300
gaattagttg acttgctggg cttagcacgt ctggaagttc cgggctatga agcagatgat  360
gttttagcct cactgaccaa aaaagccgaa aagaaggct atgaagttcg cattctgacc  420
gcagataagg atctgtatca gctgctgagc gatcgtattc atgtgttaca tccggaaggc  480
tatctgatta ccccggcatg gttatgggaa aaatatggtt tacgtccgga tcagtgggca  540
gattatcgtg cactgaccgg tgacgaatca gataatctgc cggcgttaa aggtattggt  600
gaaaaaaccg cccggaaatt attagaagaa tggggtagtc tggaagcatt actgaaaaat  660
```

```
ctggatcgcc tgaaaccggc aattcgcgaa aaaattttag cccacatgga tgacttaaaa    720
ctgtcttggg atctgccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtcgga aagaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgat cgttctggca   1080
ttaagggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttccgctt agcaggtcat   1440
ccgtttaact taaatagtcg cgatcagctg gaaagggttc tgttgatga attaggcctg   1500
ccggcaattg caagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catacccgtt ttaatcagac cgccaccgcc accggtcgct tatcaagtag cgatccgaac   1740
ttgcagaata ttccggtgcg taccccgtta ggtcagcgaa ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaacccgcct cttggatgtt tggtgttccg cgcgaagcag ttgatcctt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag tcgtcgtcg cggctatgtg   2160
gaaacccgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaagtgtg tatccgttag cagttccgtt agaagtggaa   2460
gtgggtattg gtgaagattg gctgagcgcc aaagaaggtt ctggcagttc aggtcatcac   2520
caccatcatc actaa                                                    2535

SEQ ID NO: 28         moltype = AA   length = 844
FEATURE               Location/Qualifiers
REGION                1..844
                      note = Description of Artificial Sequence: Synthetic
                      polypeptide
source                1..844
                      mol_type = protein
                      organism = synthetic construct
SEQUENCE: 28
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLIVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                 844

SEQ ID NO: 29         moltype = DNA   length = 2535
FEATURE               Location/Qualifiers
misc_feature          1..2535
                      note = Description of Artificial Sequence: Synthetic
                      polynucleotide
source                1..2535
                      mol_type = other DNA
                      organism = synthetic construct
SEQUENCE: 29
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga gatggcgat    180
gcagtgattg ttgtgtttga tgccaaagcc ccgagctttc gtcatgaagc ctatggcggc   240
tacaaagcag gtcgcgcccc gaccccggaa gattttccgc gtcagctggc cttaattaaa   300
gaattagttg acttgctggg cttagcacgt ctggaagttc cgggctatga agcagatgat   360
gttttgcct cactggccaa aaaagccgaa aaagaagtcg cattctggaa tgaagttcg    420
gcagataagg atctgtatca gctgctgagc gatcgtattc atgtgttaca tccggaaggc   480
tatctgatta cccggcatg ttatgggaa aatatggtt acgtcccgga tcagtgggca   540
gattatcgtg cactgaccgg tgacgaatca gataatctgc cgggcgttaa aggtattggt   600
gaaaaaaccg cccggaaatt attagaagaa tgggtagtc tggaagcatt actgaaaaat   660
ctggatcgcc tgaaaccggc aattcgcgaa aaaattttag cccacatgga tgacttaaaa   720
```

```
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actgaatctc cgaaagcat  tagaagaagc cccgtggccg    900
ccgccgaag  gcgcctttgt gggctttgtg ctgagtagga agaaccgat  gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
tctagggaag gcttaggcct gccgccgggc gatgatccga tgctgctggc ctatctgctt   1140
gacccgagta taccacccc  ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtga aacgtccgct gagcgcagtg   1320
ctggcacaca tggaagccac cggtgtgcgc ttagatgttg catatctgcg tgccctgtct   1380
ctggaagttg cagaagaaat tgcacgctta aagccgaag  ttttcgctt  agcaggtcat   1440
ccgtttaact aaatagtcg  cgatcagctg aaagggttc  tgtttgatga attaggcctg   1500
ccggcaattg gcaagaccga aaaaaccggt aaacgtccta cctcagccgc agttctggaa   1560
gccctgcgcg aagcccatcc gattgttgaa aaaatttac  agtatcgtga actgaccaaa   1620
ctgaaatcta cctatattga tccgttaccg gatctaattc atccgcgtac cggtcgctta   1680
catacccgtt ttaatcagac cgccaccgcc accggtcgct atcaagtag  cgatccgaac   1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaacctgt  ttggtcgtcg tcgctatgtt ccggatctgg aagcgagagt taaatcagtg   2220
cgtgaagccg ccgaacgcat ggcctttaat atgccggttc agggaaccgc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaagtgtg  tatccgttag cagttccgtt agaagtggaa   2460
gtgggtattg tgaagattg  gctgagcgcc aaagaaggtt ctggcagttc aggtcatcac   2520
caccatcatc actaa                                                    2535

SEQ ID NO: 30          moltype = AA  length = 844
FEATURE                Location/Qualifiers
REGION                 1..844
                       note = Description of Artificial Sequence: Synthetic
                       polypeptide
source                 1..844
                       mol_type = protein
                       organism = synthetic construct
SEQUENCE: 30
MRGMLPLFEP KGRVLLVDGH HLAYRTFHAL KGLTTSRGEP VQAVYGFAKS LLKALKEDGD     60
AVIVVFDAKA PSFRHEAYGG YKAGRAPTPE DFPRQLALIK ELVDLLGLAR LEVPGYEADD    120
VLASLAKKAE KEGYEVRILT ADKDLYQLLS DRIHVLHPEG YLITPAWLWE KYGLRPDQWA    180
DYRALTGDES DNLPGVKGIG EKTARKLLEE WGSLEALLKN LDRLKPAIRE KILAHMDDLK    240
LSWDLAKVRT DLPLEVDFAK RREPDRERLR AFLERLEFGS LLHEFGLLES PKALEEAPWP    300
PPEGAFVGFV LSRKEPMWAD LLALAAARGG RVHRAPEPYK ALRDLKEARG LLAKDLSVLA    360
LREGLGLPPG DDPMLLAYLL DPSNTTPEGV ARRYGGEWTE EAGERAALSE RLFANLWGRL    420
EGEERLLWLY REVERPLSAV LAHMEATGVR LDVAYLRALS LEVAEEIARL EAEVFRLAGH    480
PFNLNSRDQL ERVLFDELGL PAIGKTEKTG KRSTSAAVLE ALREAHPIVE KILQYRELTK    540
LKSTYIDPLP DLIHPRTGRL HTRFNQTATA TGRLSSSDPN LQNIPVRTPL GQRIRRAFIA    600
EEGWLLVALD YSQIELRVLA HLSGDENLIR VFQEGRDIHT ETASWMFGVP REAVDPLMRR    660
AAKTINFGVL YGMSAHRLSQ ELAIPYEEAQ AFIERYFQSF PKVRAWIEKT LEEGRRRGYV    720
ETLFGRRRYV PDLEARVKSV REAAERMAFN MPVQGTAADL MKLAMVKLFP RLEEMGARML    780
LQVHDELVLE APKERAEAVA RLAKEVMEGV YPLAVPLEVE VGIGEDWLSA KEGSGSSGHH    840
HHHH                                                                844

SEQ ID NO: 31          moltype = DNA  length = 2535
FEATURE                Location/Qualifiers
misc_feature           1..2535
                       note = Description of Artificial Sequence: Synthetic
                       polynucleotide
source                 1..2535
                       mol_type = other DNA
                       organism = synthetic construct
SEQUENCE: 31
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag gtcgcgcccc gaccccggaa gattttccgc gtcagctggc cttaattaaa    300
gaattagttg acttgctggg cttagcacgt ctggaagttc cgggctatga agcagatgat    360
gttttagcct cactggccaa aaaagccgaa aagaaggct  atgaagttcg cattctgacc    420
gcagataagg atctgtatca gctgctgagc gatcgtatta gtgttttaca tccggaaggc    480
tatctgatta cccccgcatg ttatgatgaa aaatatggtt tacgtccgga tcagtggca    540
gattatcgtg cactgaccgg tgacgaatca gataatctgc cggcgttaa  aggtattggt    600
gaaaaaaccg cccggaaatt attaagaa   tggggtagtc tggaagcatt actgaaaaat    660
ctggatcgct tgaaaccggc aattcgcgaa aaaatttag  cccacatgga tgacttaaaa    720
ctgtcttggg atctggccaa agtgcgtacc gatctgccgt tagaagttga ttttgccaaa    780
```

```
cgtcgcgaac cggatcgtga acgcctacga gcctttctgg aacgcttaga atttggctca   840
ctgttacatg aatttggctt actgaatct ccgaaagcat tagaagaagc ccgtgtgccg    900
ccgccggaag gcgcctttgt gggctttgtg ctgagtagga agaaccgat gtgggcagac    960
ttgctggccc tggccgcagc acgcggcggt cgcgttcatc gtgccccgga accgtacaaa  1020
gccctgcgtg acctgaaaga agcacgcggc ttattagcca aagacctgag tgttctggca  1080
ttaagggaag gcttaggcct gccgccgggc gatgatccga tgctgtctgc ctatctgctt  1140
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtga aacgtccgct gagcgcagtg  1320
ctggcacaca tggaagccac cggtgtgcgc ttagatgttg catatctgcg tgccctgtct  1380
ctggaagttg cagaagaaat tgcacgctta gaagccgaag ttttcgctt agcaggtcat   1440
ccgtttaact aaatagtcg cgatcagctg gaaagggttc tgtttgatga attaggcctg   1500
ccggcaattg gcaagaccga aaaaaccggt aaacgctcta cctcagccgc agttctggaa  1560
gccctgcgcg aagcccatcc gattgttgaa aaattttac agtatcgtga actgaccaaa   1620
ctgaaatcta cctatattga tccgttaccg gatctaattc atccgcgtac cggtcgctta  1680
catcccgtt ttaatcagac cgccaccgcc accggtcgct tatcaagtag cgatccgaac   1740
ttgcagaata ttccggtgcg taccccgtta ggtcagcgca ttcgtcgtgc ctttattgca  1800
gaagaaggtt ggttattagt tgcattagat tatagtcaga ttgaactgcg tgttagcc   1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcgcacatcg cctgtcacag  2040
gaactgcgca ttccgtatga agaagcacag gcctttattg aacgctattt tcagtctttt  2100
ccgaaagttc gcgcatggat tgaaaaaacc ttagaagaag gtcgtcgtcg cggctatgtg  2160
gaaaccctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
atgaaaactg caatggttaa actgtttccg cgcctggaa aaatgggtgc acgaatgctg  2340
ttacaggttc atgatgaatt agttctggaa gccccgaaaa aacgcgccga agcagttgca  2400
cgtctggcca aagaagtgat ggaagtgtg tatccgttag cagttccgtt agaagtggaa   2460
gtgggtattg tgaagattg gctgagcgcc aaagaaggtt ctggcagttc aggtcatcac  2520
caccatcatc actaa                                                    2535

SEQ ID NO: 32          moltype = AA  length = 844
FEATURE                Location/Qualifiers
REGION                 1..844
                       note = Description of Artificial Sequence: Synthetic
                         polypeptide
source                 1..844
                       mol_type = protein
                       organism = synthetic construct
SEQUENCE: 32
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHVLHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFAK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLSAYLL DPSNTTPEGV ARRYGGEWTE EAGERAALSE RLFANLWGRL  420
EGEERLLWLY REVERPLSAV LAHMEATGVR LDVAYLRALS LEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PDLEARVKSV REAAERMAFN MPVQGTAADL MKLAMVKLFP RLEEMGARML  780
LQVHDELVLE APKERAEAVA RLAKEVMEGV YPLAVPLEVE VGIGEDWLSA KEGSGSSGHH  840
HHHH                                                                844

SEQ ID NO: 33          moltype = DNA  length = 2535
FEATURE                Location/Qualifiers
misc_feature           1..2535
                       note = Description of Artificial Sequence: Synthetic
                         polynucleotide
source                 1..2535
                       mol_type = other DNA
                       organism = synthetic construct
SEQUENCE: 33
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga agatggcgat   180
gcagtgatta ttgtgttga tgccaaagcc ccgagcttc gtcatgaagc ctatggcgga   240
tacaaagcag gtcgcgcccc gacccccgaa gattttccgc gtcagctggc cttaattaaa   300
gaattagttg acttgctggg cttagcacgt ctggaagttc cggctatga gcagatgat   360
gttttagcct cactggccaa aaaagccgaa aagaaggct atgaagttcg cattctgacc   420
gcagataagg atctgtatca gctgctgagc gatcgtatc atgtgttaca tccggaaggc   480
tatcttgatta ccccgcatg gttatggaa aaatatggtt tacgtccgga tcagtgggca   540
gattatcgtg cactgaccgg tgacgaatca gataatctgc cgggcgttaa aggtattggt   600
gaaaaaaccg cccggaaatt attagaagaa tggggtagtc tggaagcatt actgaaaaat   660
ctggatcgcc tgaaaccggc aattcgcgaa aaaatttag cccacatgga tgacttaaaa   720
ctgtcttggg atctggccaa agtgcgtacc gatctgccgt tagaagttga ttttgccaaa   780
cgtcgcgaac cggatcgtga acgcctacga gcctttctgg aacgcttaga atttggctca   840
```

```
ctgttacatg aatttggctt actggaatct ccgaaagcat agaagaagc cccgtggccg    900
ccgccggaag cgcctttgt gggctttgtg ctgagtagga agaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaaggggaag gcttaggcct gccgccgggc gatgatccga tgctgctggc ctatctgctt   1140
gacggtagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatctga ctgcgtcgtc tgccctgtct   1380
ctggaagttg cagaagaaat tgcacgctta gaagcgaag ttttttcgctt agcaggtcat   1440
ccgtttaact aaatagtcg cgatcagctg gaaaggggttc tgtttgatga attaggcctg   1500
ccggcaattg caagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catcccgtt taatcagac cgccaccgcc accggtcgct tatcaagtag cgatccgaac   1740
ttgcagaata ttccggtgcg tacccgcgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgtga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgcgga agcagttgaa   2400
cgtctggcca aagaagtgat ggaaggtgtg tatccgttac agttccgtt agaagtggaa   2460
gtgggtattg gtgaagattg gctgagcgcc aaagaaggtt ctggcagttc aggtcatcac   2520
caccatcatc actaa                                                    2535

SEQ ID NO: 34          moltype = AA   length = 844
FEATURE                Location/Qualifiers
REGION                 1..844
                       note = Description of Artificial Sequence: Synthetic
                        polypeptide
source                 1..844
                       mol_type = protein
                       organism = synthetic construct
SEQUENCE: 34
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DGSNTTPEGV ARRYGGEWTE EAGERAALSE RLFANLWGRL   420
EGEERLLWLY REVERPLSAV LAHMEATGVR LDVAYLRALS LVEAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 35          moltype = DNA   length = 2535
FEATURE                Location/Qualifiers
misc_feature           1..2535
                       note = Description of Artificial Sequence: Synthetic
                        polynucleotide
source                 1..2535
                       mol_type = other DNA
                       organism = synthetic construct
SEQUENCE: 35
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga gatggcgat    180
gcagtgattg ttgtgtttga tgccaaaagcc ccgagctttc gtcatgaagc ctatggcggc    240
tacaaagcag gtcgcgcccc gaccccgaa gatttccgc gtcagctgc cttaattaaa    300
gaattagttg acttgctggg cttagcacgt ctggaagttc cgggctatga agcagatgat    360
gttttagcct cactggccaa aaaagccgaa aaagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt tacgtccgga tcagtgggca    540
gattatcgtg ctctgaccgg tgacgaatca gataatctgc cgggcgttaa aggtattggt    600
gaaaaaaccg cccggaaatt attagaagaa tgggggtagtc tggaagcatt actgaaaaat    660
ctggatcgcc tgaaaccggc aattcgcgaa aaaatttag cccacatgga tgactttaaa    720
ctgtcttggg atctggccaa agtgcgtacc gatctgccgt tagaagttga ttttgccaaa    780
cgtcgcgaac cggatcgtga acgctacga gcctttctgg aacgcttaga atttggctca    840
ctgttacatg aatttggctt actggaatct ccgaaagcat agaagaagc cccgtggccg    900
```

```
ccgccggaag gcgcctttgt gggctttgtg ctgagtagga aagaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag gcttaggcct gccgccgggc gatgatccga tgctgctggc ctatctgctt   1140
gacccgagta atatcacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttcgctt agcaggtcat   1440
ccgtttaact aaatagtcg cgatcagctg gaaagggttc tgtttgatga attaggcctg   1500
ccggcaattg gcaagaccga aaaaccggtt aaacgctcta cctcagccgc agttctggaa   1560
gccctgcgcg aagcccatcc gattgttgaa aaattttac agtatcgtga actgaccaaa   1620
ctgaaatcta ccctatattg tccgttaccg gatcaattct atccgcgtac cggtcgctta   1680
cataccgttt ttaatcagac cgccaccgcc accgtcgct tatcaagtga cgatccgaac   1740
ttgcagaata ttccggtgcg tacccgtta ggtcagcgaa ttcgtcgtgc ctttattgca   1800
gaagaaggtt ggtattagt tgcattagat atagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaacgctgt ttggtcgtcg tcgctatgtt ccggatctgg aagcgagagt taaatcgtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctgaa gccccgaaag aacgcgccga agcagttgca   2400
cgtctggcca aagaagtgat ggaagtgtg tatccgttag cagttccgtt agaagtgaa   2460
gtgggtattg gtgaagattg gctgagcgcc aaagaaggtt ctggcagttc aggtcatcac   2520
caccatcatc actaa                                                   2535

SEQ ID NO: 36          moltype = AA   length = 844
FEATURE                Location/Qualifiers
REGION                 1..844
                       note = Description of Artificial Sequence: Synthetic
                        polypeptide
source                 1..844
                       mol_type = protein
                       organism = synthetic construct
SEQUENCE: 36
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNITPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 37          moltype = DNA   length = 2535
FEATURE                Location/Qualifiers
misc_feature           1..2535
                       note = Description of Artificial Sequence: Synthetic
                        polynucleotide
source                 1..2535
                       mol_type = other DNA
                       organism = synthetic construct
SEQUENCE: 37
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag gtcgcgcccc gaccccggaa gattttccgc gtcagctggc cttaattaaa    300
gaattagttg acttgctggg cttagcacgt ctggaagttc cgggctatga agcagatgat    360
gttttagcct cactggccaa aaaagccgaa aaagaaggct atgaagttcg cattctgacc    420
gcagataagg atctgtatca gctgctgagc gatcgtattc atgtgttaca tccgaaggc    480
tatctgatta ccccggcatg gttatggaa aaatatggtt tacgtccgga tcagtgggca    540
gattatcgtg cactgaccgg tgacgaatca gataatctgc cgggcgttaa aggtattggt    600
gaaaaaaccg cccgtaaatt attagaagaa tggggtagcc tggaagcatt actgaaaaat    660
ctggatcgcc tgaaaccggc aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgctacga gcctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtagga aagaaccgat gtgggcagac    960
```

-continued

```
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag cttaggcct gccgccgggc gatgatccga tgctgctggc ctatctgctt    1140
gacccgagta taccacccc ggaaggcgtt gcacgtcgct atggcggcga gtggaccgaa    1200
gaagcaggcg aacgtgcagc cctgtcagaa cgtctgtttg ccaatctgtg gcctcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttcgctt agcaggtcat    1440
ccgtttaact taaatagtcg cgatcagctg gaaaggttc tgtttgatga attaggcctg    1500
ccggcaattg gcaagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catcccgtt taatcagac cgccaccgcc accggtcgct tatcaagtag cgatccgaac    1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gccttattg aacgctattt tcagtctttt    2100
ccgaaagttc gcgcatggat tgaaaaaacc ttagaagaag tcgtcgtcg cggctatgtg    2160
gaaaccctgt ttggtcgtcg tcgctatgtt ccggatctgg aagcgagagt taaatcagtg   2220
cgtgaagccg ccgaacgcat ggcctttaat atgccggtcc agggaaccgc agctgacctt   2280
atgaaactgg caatggttaa actgtttccg cgcctggaag aaatgggtgc acgaatgctg   2340
ttacaggttc atgatgaatt agtctctgaa gccccgaaag aacgcgccga agcagttgca   2400
cgtctggcca agaagtgat ggaaggtgtg tatccgttag cagttccgtt agaagtgaaa    2460
gtgggtattg tgaagattg gctgagcgcc aagaaaggtt ctggcagttc aggtcatcac   2520
caccatcatc actaa                                                    2535

SEQ ID NO: 38           moltype = AA  length = 844
FEATURE                 Location/Qualifiers
REGION                  1..844
                        note = Description of Artificial Sequence: Synthetic
                        polypeptide
source                  1..844
                        mol_type = protein
                        organism = synthetic construct
SEQUENCE: 38
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWPRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSGPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 39           moltype = DNA  length = 2535
FEATURE                 Location/Qualifiers
misc_feature            1..2535
                        note = Description of Artificial Sequence: Synthetic
                        polynucleotide
source                  1..2535
                        mol_type = other DNA
                        organism = synthetic construct
SEQUENCE: 39
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga gatgggcgat   180
gcagtgattg ttgtgtttga tgccaaagcc ccgagctttc gtcatgaagc ctatggcggc   240
tacaaagcag gtcgcgcccc gaccccggaa gattttccgc gtcagctggc cttaattaaa   300
gaattagttg acttgctggg cttagcacgt ctggaagttc cgggctatga agcagatgat   360
gttttagcct cactggccaa aaaagccgaa aaagaaggct atgaagttcg cattctgacc   420
gcagataagg atctgtatca gctgctgagc gatcgtattc atgtgttaca tccggaaggc   480
tatctgatta ccccggcatg gttatgggaa aaatatggtt tacgtccgga tcagtgggca   540
gattatcgtg cactgaccgg tgacgaatca gataatctgc cgggcgttaa aggtattggt   600
gaaaaaaccg cccggaaatt attagaagaa tggggtagtc tggaagcatt actgaaaaat   660
ctggatcgtc tgaaaccggc aattcgcgaa aaaattttag cccacatgga tgacttaaaa   720
ctgtcttggg atctggccaa agtgcgtacc gatctgccgt tagaagttga ttttgccaaa   780
cgtcgcgaac cggatcgtga acgcctacga gcctttctgg aacgcttaga atttggctca   840
ctgttacatg aatttggcctt actggaatct ccgaaagcat tagaagaagc cccgtggccg   900
ccgccggaag gcgcctttgt gggctttgtg ctgagtagga agaaccgat gtgggcagac    960
ttgctggccc tggccgcagc acgcggcggt cgcgttcatc gtgccccgga accgtacaaa   1020
```

-continued

```
gccctgcgtg acctgaaaga agcacgcggc ttattagcca aagacctgag tgttctggca  1080
ttaagggaag gcttaggcct gccgccgggc gatgatccga tgctgctggc ctatctgctt  1140
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtgactta  1260
gaaggcgaag aacgcttact gtggttatat cgtgaagtgg aacgtccgct gagcgcagtg  1320
ctggcacaca tggaagccac cggtgtgcgc ttagatgttg catatctgcg tgccctgtct  1380
ctggaagttg cagaagaaat tgcacgctta gaagccgaag tttttcgctt agcaggtcat  1440
ccgtttaact taaatagtcg cgatcagctg gaaagggttc tgtttgatga attaggcctg  1500
ccggcaattg gcaagaccga aaaaaccggt aaacgtccta cctcagccgc agttctggca  1560
gccctgcgcg aagcccatcc gattgttgaa aaattttac agtatcgtga actgaccaaa  1620
ctgaaatcta cctatattga tccgttaccg gatctaattc atccgcgtac cggtcgctta  1680
catcccgtt ttaatcagac cgccaccgcc accggtcgct tatcaagtag cgatccgaac  1740
ttgcagaata ttccggtgcg taccccgtta ggtcagcgca ttcgtcgtgc ctttattgca  1800
gaagaaggtt ggtattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcgcacatcg cctgtcacag  2040
gaactggcaa ttccgtatga agaagcacag gcctttattg aacgctattt tcagtctttg  2100
ccgaaagttc gcgcatggat tgaaaaaacc ttagaagaag gtcgtcgtcg cggctatgtg  2160
gaaaccctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
atgaaactgg caatggttaa actgtttccg cgcctggaaa tgggtgccag aatgctg     2340
ttacaggttc atgatgaatt agttctgaa gccccgaaag aacgcgccga agcagttgca  2400
cgtctggcca aagaagtgat ggaagtgtg tatccgttag cagttccgtt agaagtggaa  2460
gtgggtattg tgaagattg gctgagcgcc aaagaaggtt ctggcagttc aggtcatcac  2520
caccatcatc actaa                                                    2535

SEQ ID NO: 40            moltype = AA   length = 844
FEATURE                  Location/Qualifiers
REGION                   1..844
                         note = Description of Artificial Sequence: Synthetic
                         polypeptide
source                   1..844
                         mol_type = protein
                         organism = synthetic construct
SEQUENCE: 40
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGDL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 41            moltype = DNA   length = 2535
FEATURE                  Location/Qualifiers
misc_feature             1..2535
                         note = Description of Artificial Sequence: Synthetic
                         polynucleotide
source                   1..2535
                         mol_type = other DNA
                         organism = synthetic construct
SEQUENCE: 41
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga agatggcgat   180
gcagtgattg ttgtgtttga tgccaaagcc ccgagctttc gtcatgaagc ctatggcggc   240
tacaaagcag gtcgcgcccc gacccggaa gattttccgc gtcagctggc cttaattaaa   300
gaattagttg acttgctggg cttagcacgt ctggaagttc cgggctatga agcagatgat   360
gttttagcct cactggccaa aaaagcggaa aaagaaggct atgaagttcg cattctgacc   420
gcagataagg atctctgatca gctgctgagc gatcgtattc atgttttaca tccggaaggc   480
tatctgatta ccccgcatg gttatggaa aaatatggtt tacgtccgga tcagtgggca   540
gattatcgtg cactgaccgg tgacgaatca gataatctgc cgggcgttaa aggtattggt   600
gaaaaaaccg cccggaaatt attagaagaa tgggtagtc tggaagcatt actgaaaaat   660
ctggatcgcc tgaaaccggc aattcgcgaa aaaattttag cccacatgga tgacttaaaa   720
ctgtcttggg atctcgcaa agtgcgtacc gatctgccgt tagaagttga tttgccaaa    780
cgtcgcgaac cggatcgtga acgcctacga gcctttctgg aacgcttaga atttggctca   840
ctgttacatg aatttggctt actggaatct ccgaaagcat tagaagaagc ccgtggccg    900
ccgccggaag cgcctttgt gggctttgtg ctgagtagga agaaccgat gtgggcagac   960
ttgctggccc tggccgcagc acgggcggt cgcgttcatc gtgccccgga accgtacaaa  1020
gccctgcgtg acctgaaaga agcacgcggc ttattagcca aagacctgag tgttctggca  1080
```

```
ttaagggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
aaaggcgaag aacgcttact gtggttatat cgtgaagtgg aacgtccgct gagcgcagtg   1320
ctggcacaca tggaagccac cggtgtgcgc ttagatgttg catatcgtga tgccctgtct   1380
ctggaagttg cagaagaaat tgcacgctta gaagccgaag ttttcgctt agcaggtcat    1440
ccgtttaact aaatagtcg cgatcagctg gaaagggttc tgtttgatga attaggcctg    1500
ccggcaattg caagaccga aaaaccggt aaacgctcta cctcagccgc agttctggaa     1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catacccgtt ttaatcagac cgccaccgcc accggtcgct tatcaagtag cgatccgaac   1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgaaga agcagttgca   2400
cgtctggcca aagaagtgat ggaagtgtg tatccgttag cagttccgtt agaagtggaa    2460
gtgggtattg gtgaagattg gctgagcgcc aaagaaggtt ctggcagttc aggtcatcac   2520
caccatcatc actaa                                                   2535

SEQ ID NO: 42        moltype = AA  length = 844
FEATURE              Location/Qualifiers
REGION               1..844
                     note = Description of Artificial Sequence: Synthetic
                     polypeptide
source               1..844
                     mol_type = protein
                     organism = synthetic construct
SEQUENCE: 42
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
KGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKEREAVA RLAKEVMEGV YPLAVPLEVE VGIGEDWLSA KEGSGSSGHH    840
HHHH                                                                844

SEQ ID NO: 43        moltype = DNA  length = 2535
FEATURE              Location/Qualifiers
misc_feature         1..2535
                     note = Description of Artificial Sequence: Synthetic
                     polynucleotide
source               1..2535
                     mol_type = other DNA
                     organism = synthetic construct
SEQUENCE: 43
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga gatggcgat    180
gcagtgattg ttgtgtttga tgccaaagcc ccgagcttc gtcatgaagc ctatggcgga   240
tacaaagcag gtcgcgcccc gaccccggaa gattttccgc gtcagctggc cttaattaaa   300
gaattagttg acttgctggg cttagcacgt ctggaagttc cgggctatga agcagatgat   360
gttttagcct cactggccaa aaaagccgaa aaagaaggct atgaagttcg cattctgacc   420
gcagataagg atctgtatca gctgctgagc gatcgtattc atgtgttaca tccggaaggc   480
tatctgatta ccccggcatg gttatgggaa aaatatggtc tacgccgga tcagtgggca   540
gattatcgtg cactgaccgg tgacgaatca gataatctgc cgggcgttaa aggtattggt   600
gaaaaaaccg cccggaaatt attagaagaa tggggtagtc tggaagcatt actgaaaaat   660
ctggatcgcc tgaaaccggc aattcgcgaa aaaatttag cccacatgga tgacttaaaa   720
ctgtcttggg atctggccaa agtgcgtacc gatctgccgt tagaagttga ttttgccaaa   780
cgtcgcgaac cggatcgtga acgcttacga gcctttctgg aacgcttaga atttggctca   840
ctgttacatg aatttggctt actggaatct ccgaaagcat tagaagaagc cccgtggccg   900
ccgccggaag cgccctttgt gggctttgtg ctgagtagga agaaccgat gtgggcgac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag gcttaggcct gccgccgggc gatgatccga tgctgctggc ctatctgctt   1140
```

```
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtgg aacgtccgct gagcgcagtg  1320
ctggcacaca tggaagccac cggtgtgcgc ttagatgttg catatctgcg tgccctgtct  1380
tctgaagttg cagaagaaat tgcacgctta gaagccgaaa tttttcgctt agcaggtcat  1440
ccgtttaact aaatagtcg cgatcagctg gaaaggggtc tgtttgatga attaggcctg  1500
ccggcaattg gcaagaccga aaaaaccggt aaacgctcta cctcagccgc agttctggaa  1560
gccctgcgcg aagcccatcc gattgttgaa aaaattttac agtatcgtga actgaccaaa  1620
ctgaaatcta cctatattga tccgttaccg gatctaattc atccgcgtac cggtcgctta  1680
catacccgtt ttaatcagac cgccaccgcc accggtcgct tatcaagtag cgatccgaac  1740
ttgcagaata ttccggtgcg taccccgtta ggtcagcgca ttcgtcgtgc ctttattgca  1800
gaagaaggtt ggttattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtcgccg cgcgaagcag ttgatccgtt aatgcgccgt  1980
gcagccaaaa ccattaattt tggtgtgctg tatggtatga gcgcacatcg cctgtcacag  2040
gaactggcaa ttccgtatga agaagcacag gcctttattg aacgctattt tcagtctttt  2100
ccgaaagttc gcgcatggat tgaaaaaacc ttagaagaag gtcgtcgtcg cggctatgtg  2160
gaaaccctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
atgaaactgg caatggttaa actgtttccg cgcctggaag aaatgggtgc acgaatgctg  2340
ttacaggttc atgatgaatt agttctgaaa gccccgaaaa aacgcgccga agcagttgca  2400
cgtctggcca aagaagtgat ggaaggtgtg tatccgttag cagttccgtt agaagtgaaa  2460
gtgggtattg gtgaagattg gctgagcgcc aaagaaggtt ctggcagttc aggtcatcac  2520
caccatcatc actaa                                                   2535

SEQ ID NO: 44          moltype = AA  length = 844
FEATURE                Location/Qualifiers
REGION                 1..844
                       note = Description of Artificial Sequence: Synthetic
                       polypeptide
source                 1..844
                       mol_type = protein
                       organism = synthetic construct
SEQUENCE: 44
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHVLHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFAK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLLAYLL DPSNTTPEGV ARRYGGEWTE EAGERAALSE RLFANLWGRL  420
EGEERLLWLY REVERPLSAV LAHMEATGVR LDVAYLRALS SEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PDLEARVKSV REAAERMAFN MPVQGTAADL MKLAMVKLFP RLEEMGARML  780
LQVHDELVLE APKERAEAVA RLAKEVMEGV YPLAVPLEVE VGIGEDWLSA KEGSGSSGHH  840
HHHH                                                               844

SEQ ID NO: 45          moltype = DNA  length = 2535
FEATURE                Location/Qualifiers
misc_feature           1..2535
                       note = Description of Artificial Sequence: Synthetic
                       polynucleotide
source                 1..2535
                       mol_type = other DNA
                       organism = synthetic construct
SEQUENCE: 45
atgcgcggta tgctgccgtt atttgaaccg aaaggtcgtg tgctgctggt tgatggtcat   60
cacttagcat atcgtacctt tcatgccctg aaaggcctga ccacctctcg cggcgaaccg  120
gttcaggcag tgtatggttt tgccaaatca ctgctgaaag cattaaaaga agatggcgat  180
gcagtgattg ttgtgtttga tgccaaagcc ccgagctttc gtcatgaagc ctatggcggc  240
tacaaagcag gtcgcgcccc gacccgggaa gattttccgc gtcagctgca cttaattaaa  300
gaattagttg acttgctggg cttagcacgc ctggaagttc cgggctatga agcagatgat  360
gttttagcct cactggccaa aaaagccgaa aagaaggct atgaagttcg cattctgacc  420
gcagataagg atctgtatca gctgctgagc gatcgtattc atgtgttaca tccggaaggc  480
tatctgatta ccccggcatg gttatgggaa aaatatggtt tacgtccgga tcagtgggca  540
gattatcgtg cactgaccgg tgacgaatca gataatctgc cgggcgttaa aggtattggt  600
gaaaaaaccg cccggaaatt attagaagaa tgggtagtc tggaagcatt actgaaaaat  660
ctggatcgcc tgaaaccggc aattcgcgaa aaaattttag cccacatgga tgacttaaaa  720
ctgtcttggg atctggccaa agtgcgtacc gatctgccgt tagaagttga ttttgccaaa  780
cgtcgcgaac cggatcgtga acgcctacga gcctttctgg aacgcttaga atttggctca  840
ctgttacatg aatttggctt actgaatct ccgaaagcat tagaagaagc cccgtggccg  900
ccgccggaag cgcctttgt gggctttgtg ctgagtagga agaaccgat gtgggcagac  960
ttgctgccc tggccgcagc acgcggcggt gcgttcatc gtgccccgga accgtacaaa 1020
gccctgcgtg acctgaaaga agcacgcggg ttattagcca aagacctgag tgttctggca 1080
ttaagggaag gcttaggcct gccgccgggc gatgatccga tgctgctggc ctatctgctt 1140
gacccgagta ataccacccc ggaaggcgtt gcacgtcgct atggcggcga gtggaccgaa 1200
```

```
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaattcgaag ttttcgctt agcaggtcat    1440
ccgtttaact taaatagtcg cgatcagctg gaaagggttc tgtttgatga attaggcctg   1500
ccggcaattg caagaccga aaaaaccggt aaacgctcta cctcagccgc agttctggaa    1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
cataccgtt ttaatcagac cgccaccgcc accggtcgct tatcaagtag cgatccgaac    1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag tcgtcgtcg cggctatgtg    2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca agaagtgat ggaaggtgtg tatccgttag cagttccgtt agaagtgaa     2460
gtgggtattg gtgaagattg gctgagcgcc aagaaggtt ctggcagttc aggtcatcac    2520
caccatcatc actaa                                                    2535

SEQ ID NO: 46          moltype = AA  length = 844
FEATURE                Location/Qualifiers
REGION                 1..844
                       note = Description of Artificial Sequence: Synthetic
                       polypeptide
source                 1..844
                       mol_type = protein
                       organism = synthetic construct
SEQUENCE: 46
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EFEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 47          moltype = DNA  length = 2535
FEATURE                Location/Qualifiers
misc_feature           1..2535
                       note = Description of Artificial Sequence: Synthetic
                       polynucleotide
source                 1..2535
                       mol_type = other DNA
                       organism = synthetic construct
SEQUENCE: 47
atgcgcggta tgctgccgtt atttgaaccg aaaggtcgtg tgctgctggt tgatggtcat     60
cacttagcat atcgtaccct tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag gtcgcgcccc gaccccggaa gattttccgc gtcagctggc cttaattaaa    300
gaattagttg acttgctggg cttagcacgt ctggaagttc cgggctatga agcagatgat    360
gttttagcct cactgaccaa aaaagccgaa aaagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt tacgtccgga tcagtgggca    540
gattatcgtg cactgaccgg tgacgaatca gataatctgc cgggcgttaa aggtattggt    600
gaaaaaaccg cccggaaatt attagaagaa tgggtagtc tggaagcatt actgaaaaat    660
ctggatcgcc tgaaaccggc aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgctacga gcctttctgg aacgcttaga atttggctca    840
ctgttacatg aatttggctt actggaatct ccgaaagcat tagaagaagc cccgtggccg    900
ccgccagaag gcgcctttgt tggcttttgt ctgagtagga agaaccgat gtgggcgac     960
ttgctggccc tggccgcagc acgcggcggt cgcgttcatc gtgccccgga accgtacaaa   1020
gccctgcgtg acctgaaaga agcacgcggc ttattagcca aagaccctgag tgttctggca   1080
ttaagggaag gcttaggcct gccgccgggg gatgatccga tgctgctggc ctatctgctt   1140
gacccgagta taccaccccc ggaaggcgtt gcacgtcgct atggcggcga gtggaccgaa   1200
gaagcaggcg aacgtgcagc cctgtcagaa cgtctgtttg ccaatctgtg gggtcgctta   1260
```

-continued

```
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttcgctt agcaggtcat    1440
ccgtttaact aaatagtcg cgatcagctg gaaagggttc tgtttgataa attaggcctg    1500
ccggcaattg gcaagaccga aaaaaccggt aaacgtcta cctcagccgc agttctggaa    1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catcccgtt ttaatcagac cgccaccgcc accggtcgct tatcaagtag cgatccgaac    1740
ttgcagaata ttccggtgcg taccccgtta ggtcagcgca ttcgtcgtgc cttttattga   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttc   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctgaa gccccgaaag aacgcgccga agcagttgca    2400
cgtctggcca agaagtgat ggaagtgtg tatccgttag cagttccgtt agaagtggaa     2460
gtgggtattg tgaagattg gctgagcgcc aaagaaggtt ctggcagttc aggtcatcac    2520
caccatcatc actaa                                                    2535

SEQ ID NO: 48            moltype = AA   length = 844
FEATURE                  Location/Qualifiers
REGION                   1..844
                         note = Description of Artificial Sequence: Synthetic
                         polypeptide
source                   1..844
                         mol_type = protein
                         organism = synthetic construct
SEQUENCE: 48
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDKLGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 49            moltype = DNA   length = 2535
FEATURE                  Location/Qualifiers
misc_feature             1..2535
                         note = Description of Artificial Sequence: Synthetic
                         polynucleotide
source                   1..2535
                         mol_type = other DNA
                         organism = synthetic construct
SEQUENCE: 49
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag gtcgcgcccc gaccccggaa gattttccgc gtcagctggc cttaattaaa    300
gaattagttg acttgctggg cttagcacgt ctggaagttc cgggctatga agcagatgat    360
gttttagcct cactgcgcaa aaaagccgaa aaagaagtcg cattctgaa gcagataagg    420
atctgtatca gctgctgagc gatcgtattc atgtgttaca tccggaaggc                480
tatctgatta cccccggcatg gttatgggaa aaatatggtt tacgtccgga tcagtgggca   540
gattatcgtg cactgaccgg tgacgaatca gataatctgc cgggcgttaa aggtattggt    600
gaaaaaaccg cccggaaatt attagaagaa tggggtagtc tggaagcatt actgaaaaat    660
ctggatcgcc tgaaaccggc aattcgcgaa aaaattttac cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtagga agaaccgat gtgggcagac    960
ttgctgcca cggccgcagc acgacgcggt gcgttcatc gtgccccga accgtacaaa      1020
gccctgcgcg acctgaaaga agcacgcggc ttattagcca aagacctgag tgttctggca   1080
ttaagggaag gcttaggcct gccgccgggc gatgatccga tgctgctggc ctatctgctt   1140
gacccgagta taccacccc ggaaggcgtt gcacgtcgct atggcggcga gtggaccgaa    1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
```

```
ctggcacaca tggaagccac cggtgtgcgc ttagatgttg catatctgcg tgccctgtct   1380
ctggaagttg cagaagaaat tgcacgctta gaagccgaag ttttcgctt agcaggtcat    1440
ccgtttaact aaatagtcg cgatcagctg gaaagggttc tgtttgatga atctggcctg    1500
ccggcaattg gcaagaccga aaaaccggt aaacgctcta cctcagccgc agttctggaa    1560
gccctgcgcg aagcccatcc gattgttgaa aaaatttac agtatcgtga actgaccaaa    1620
ctgaaatcta cctatattga tccgttaccg gatctaattc atccgcgtac cggtcgctta    1680
catacccgtt ttaatcagac cgccaccgcc accggtcgct tatcaagtag cgatccgaac    1740
ttgcagaata ttccggtgcg taccccgtta ggtcagcgca ttcgtcgtgc ctttattgca    1800
gaagaaggtt ggttattagt tgcattagat tatagtcaga ttgaactgcg tgtgttagcc    1860
catctgagcg gcgacgaaaa tctgattcgt gtgtttcagg aaggtcgcga tattcatacc    1920
gaaaccgcct cttggatgtt tggtgttccg cgcgaagcag ttgatccgtt aatgcgccgt    1980
gcagccaaaa ccattaattt tggtgtgctg tatggtatga gcgcacatcg cctgtcacag    2040
gaactggcaa ttccgtatga agaagcacag gccttttattg aacgctattt tcagtctttt    2100
ccgaaagttc gcgcatggat tgaaaaaacc ttagaagaag gtcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctggaag aaatgggtgc acgaatgctg    2340
ttacaggttc atgatgaatt agttctggaa gccccgaaag aacgcgccga agcagttgca    2400
cgtctggcca aagaagtgat ggaaggtgtg tatccgttag cagttccgtt agaagtggaa    2460
gtgggtattg gtgaagattg gctgagcgcc aaagaaggtt ctggcagttc aggtcatcac    2520
caccatcatc actaa                                                     2535

SEQ ID NO: 50          moltype = AA  length = 844
FEATURE                Location/Qualifiers
REGION                 1..844
                       note = Description of Artificial Sequence: Synthetic
                        polypeptide
source                 1..844
                       mol_type = protein
                       organism = synthetic construct
SEQUENCE: 50
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERRLWLY REVERPLSAV LAHMEATGVR LDVAYLRALS LEVAEEIARL EAEVFRLAGH   480
PFNLNSRDQL ERVLFDESGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                 844

SEQ ID NO: 51          moltype = DNA  length = 2535
FEATURE                Location/Qualifiers
misc_feature           1..2535
                       note = Description of Artificial Sequence: Synthetic
                        polynucleotide
source                 1..2535
                       mol_type = other DNA
                       organism = synthetic construct
SEQUENCE: 51
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag gtcgcgcccc gacccggaa gattttccgc gtcagctggc cttaattaaa    300
gaattagttg acttgctggg cttagcacgt ctggaagttc cgggctatga agcagatgat    360
gttttagcct cactggccaa aaaagccgaa aaagaaggct atgaagttcg cattctgacc    420
gcagataagg atctgtatca gctgctgagc gatcgtattc atgtgttaca tccggaaggc    480
tatctgatta ccccggcatg gttatggaa aaatatggtt tacgtccgga tcagtggca    540
gattatcgtg cactgaccgg tgacgaatca gataatctgc cgggcgttaa aggtattggt    600
gaaaaaaccg cccggaaatt attagaagaa tggggtagtc tggaagcatt actgaaaaat    660
ctggatcgcc tgaaacgaa aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtagga agaaccgat gtgggcagac    960
ttgctggccc tggccgcagc acgcggcggt cgcgttcatc gtgccccgga accgtacaaa    1020
gccctgcgcg acctgaaaga agcacgcggt ttattagcca aagacctgag tgttctggca    1080
ttagggaag gcttaggcct gccgccgggc gatgatccga tgctgctggc ctatctgctt    1140
gacccgagta ataccacccc ggaaggcgtt gcacgtcgct atggcggcga gtggaccgaa    1200
gaagcaggcg aacgtgcagc cctgtcagaa cgtctgtttg ccaatctgtg gggtcgctta    1260
gaaggcgaag aacgcttact gtggttatat cgtgaagtgg aacgtccgct gagcgcagtg    1320
ctggcacaca tggaagccac cggtgtgcgc ttagatgttg catatctgcg tgccctgtct    1380
```

```
ctggaagttg cagaagaaat tgcacgctta gaagccgaag ttttcgctt agcaggtcat    1440
ccgtttaact taaatagtcg cgatcagctg gaaagggttc tgtttgatga attaggcctg    1500
ccggcaattg gcaagaccga aaaaaccggt aaacgctcta cctcagccgc agttctggaa    1560
gccctgcgca aagcccatcc gattgttgaa aaaattttac agtatcgtga actgaccaaa    1620
ctgaaatcta cctatattga tccgttaccg gatctaattc atccgcgtac cggtcgctta    1680
catacccgtt ttaatcagac cgccaccgcc accggtcgct tatcaagtag cgatccgaac    1740
ttgcagaata ttccggtgcg taccccgtta ggtcagcgca ttcgtcgtgc ctttattgca    1800
gaagaaggtt ggttattagt tgcattagat tatagtcaga ttgaactgcg tgtgttagcc    1860
catctgagcg gcgacgaaaa tctgattcgt gtgtttcagg aaggtcgcga tattcatcc    1920
gaaaccgcct cttggatgtt tggtgttccg cgcgaagcag ttgatccgtt aatgcgccgt    1980
gcagccaaaa ccattaattt tggtgtgctg tatggtatga cgcacatcg cctgtcacag    2040
gaactggcaa ttccgtatga agaagcacag gcctttattg aacgctattt tcagtctttt    2100
ccgaaagttc gcgcatggat tgaaaaaacc ttagaagagg tcgtcgtcg cggctatgtg    2160
gaaaccctgt ttggtcgtcg tcgctatgtt ccggatctgg aagcgagagt taatcagtg    2220
cgtgaagccg ccgaacgcat ggcctttaat atgccggttc agggaacggc agctgacctt    2280
atgaaactgg caatggttaa actgtttccg cgcctggaag aaatgggtgc acgaatgctg    2340
ttacaggttc atgatgaatt agttctgaa gccccgaaag aacgcgccga agcagttgca    2400
cgtctggcca aagaagtgat ggaaggtgtg tatccgttag cagttccgtt agaagtgaa    2460
gtgggtattg gtgaagattg gctgagcgcc aaagaaggtt ctggcagttc aggtcatcac    2520
caccatcatc actaa                                                    2535

SEQ ID NO: 52           moltype = AA   length = 844
FEATURE                 Location/Qualifiers
REGION                  1..844
                        note = Description of Artificial Sequence: Synthetic
                        polypeptide
source                  1..844
                        mol_type = protein
                        organism = synthetic construct
SEQUENCE: 52
MRGMLPLFEP KGRVLLVDGH HLAYRTFHAL KGLTTSRGEP VQAVYGFAKS LLKALKEDGD     60
AVIVVFDAKA PSFRHEAYGG YKAGRAPTPE DFPRQLALIK ELVDLLGLAR LEVPGYEADD    120
VLASLAKKAE KEGYEVRILT ADKDLYQLLS DRIHVLHPEG YLITPAWLWE KYGLRPDQWA    180
DYRALTGDSN DNLPGVKGIG EKTARKLLEE WGSLEALLKN LDRLKPAIRE KILAHMDDLK    240
LSWDLAKVRT DLPLEVDFAK RREPDRERLR APFLERLEFGS LLHEFGLLES PKALEEAPWP    300
PPEGAFVGFV LSRKEPMWAD LLALAAARGG RVHRAPEPYK ALRDLKEARG LLAKDLSVLA    360
LREGLGLPPG DDPMLLAYLL DPSNTTPEGV ARRYGGEWTE EAGERAALSE RLFANLWGRL    420
EGEERLLWLY REVERPLSAV LAHMEATGVR LDVAYLRALS LEVAEEIARL EAEVFRLAGH    480
PFNLNSRDQL ERVLFDELGL PAIGKTEKTG KRSTSAAVLE ALRKAHPIVE KILQYRELTK    540
LKSTYIDPLP DLIHPRTGRL HTRFNQTATA TGRLSSSDPN LQNIPVRTPL GQRIRRAFIA    600
EEGWLLVALD YSQIELRVLA HLSGDENLIR VFQEGRDIHT ETASWMFGVP REAVDPLMRR    660
AAKTINFGVL YGMSAHRLSQ ELAIPYEEAQ AFIERYFQSF PKVRAWIEKT LEEGRRRGYV    720
ETLFGRRRYV PDLEARVKSV REAAERMAFN MPVQGTAADL MKLAMVKLFP RLEEMGARML    780
LQVHDELVLE APKERAEAVA RLAKEVMEGV YPLAVPLEVE VGIGEDWLSA KEGSGSSGHH    840
HHHH                                                                 844

SEQ ID NO: 53           moltype = DNA   length = 2535
FEATURE                 Location/Qualifiers
misc_feature            1..2535
                        note = Description of Artificial Sequence: Synthetic
                        polynucleotide
source                  1..2535
                        mol_type = other DNA
                        organism = synthetic construct
SEQUENCE: 53
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga gatggcgat    180
gcagtgattg ttgtgtttga tgccaaagcc ccgagctttc gtcatgaagc ctatggcggc    240
tacaaagcag gtcgcgcccc gaccccggaa gattttccgc gtcagctggc cttaattaaa    300
gaattagttg acttgctggg cttagcacgt ctggaagttc cgggctatga agcagatgat    360
gttttagcct cactggccaa aaaagccgaa aagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt tacgtccgga tcagtgggca    540
gattatcgtg cactgaccgg tgacgaatca gataatctgc cgggcgttaa aggtattgg    600
gaaaaaaccg cccggaaatt attagaagaa tggggtagtc tggaagcatt actgaaaaat    660
ctggatcgtc tgaaaccggc aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttgtga acgcttaga atttggctca    840
ctgttacatg aatttggctt actggaatct ccgaaagcat tagaagaagc cccgtggccg    900
ccgccggaag cgccctttgt gggctttgtg ctgagtagga agaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag gcttaggcct gccgccgggc gatgatccgt tgctgctggc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg ggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttcgctt agcaggtcat   1440
```

```
ccgtttaact taaatagtcg cgatcagctg gaaagggttc tgtttgatga attaggcctg   1500
ccggcaattg gcaagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg cgtctaattc atccgcgtac cggtcgctta   1680
catcccgtt ttaatcagac cgccaccgcc accggtcgct tatcaagtcg cgatccgaac    1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatgggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag tcgtcgtcg cggctatgtg    2160
gaaacccgt ttggtcgtcg tcgctatgtt ccggatctgg aagcgagagt taaatcagtg    2220
cgtgaagccg ccgaacgcat ggcctttaat atgccggtcc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaaggtgtg tatccgttag cagttccgtt agaagtggaa   2460
gtgggtattg gaaagattg gctgagcgcc aaagaaggtt ctggcagttc aggtcatcac   2520
caccatcatc actaa                                                    2535

SEQ ID NO: 54            moltype = AA  length = 844
FEATURE                  Location/Qualifiers
REGION                   1..844
                         note = Description of Artificial Sequence: Synthetic
                         polypeptide
source                   1..844
                         mol_type = protein
                         organism = synthetic construct
SEQUENCE: 54
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP RLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 55            moltype = DNA  length = 2535
FEATURE                  Location/Qualifiers
misc_feature             1..2535
                         note = Description of Artificial Sequence: Synthetic
                         polynucleotide
source                   1..2535
                         mol_type = other DNA
                         organism = synthetic construct
SEQUENCE: 55
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga gatggcgat   180
gcagtgattg ttgtgtttga tgccaaagcc ccgagctttc gtcatgaagc ctatggcggc   240
tacaaagcag gtcgcgcccc gacccccgga gattttccgc gtcagctggc cttaattaaa   300
gaattagttg acttgctggg cttagcacgt ctggaagttc cgggctatga agcagatgat   360
gttttagcct cactgccaa aaaagccgaa aaagaaggct atgaagttcg cattctgacc    420
gcagataagg atctgtatca gctgctgagc gatcgtattc atgtgttaca tccggaaggc   480
tatctgatta ccccggcatg gttatgggaa aaatatggtt tacgtccgga tcagtgggca   540
gattatcgtg cactgaccgg tgacgaatca gataatctgc cgggcgttaa aggtattggt   600
gaaaaaaccg cccggaaatt attagaagaa tggggtagtc tggaagcatt actgaaaaat   660
ctggatcgcc tgaaaccggc aattcgcgaa aaaattttag cccacatgga tgacttaaaa   720
ctgtcttggg atctggccaa agtgcgtacc gatctgccgt tagaagttga ttttgccaaa   780
cgtcgcgaac cggatcgtga acgcctacga gcctttctgg aacgcttaga atttggctca   840
ctgttacatg aatttggctt actgaatct ccgaaagcat tagaagaagc cccgtggccg   900
ccgccggaag cgccctttgt gggctttgtg ctgagtagga agaaccgat gtgggcagac    960
ttgctggccc tggccgcagc acgcggcggt cgcgttcatc gtgccccgga accgtacaaa  1020
gccctgcgtg acctgaaaga agcacgcggg ttattagcca agacctgag tgttctggca   1080
ttaagggaag gcttaggcct gccgccgggc gatgatccga tgctgctggc ctatctgctt   1140
gacccggta ataccacccc ggaaggcgtt gcacgtyacg gcggcgaatg ggaccgaa    1200
gaagcaggcg aacgtgcagc cctgtcagaa cgtctgtttg ccaatcgtgt gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagtg cagaagaaat tgcacgctta gaagccgaag tttttcgctt agcaggtcat   1440
ccgtttaact aaatagtcg cgatcagctg gaaagggttc tgtttgatga attaggcctg    1500
```

```
ccggcaattg gcaagaccga aaaaaccggt aaacgctcta cctcagccgc agttctggaa    1560
gccctgcgcg aagcccatcc gattgttgaa aaaattttac agtatcgtga actgaccaaa    1620
ctgaaatcta cctatattga tccgttaccg gatctaattc atccggatac cggtcgctta    1680
catacccgtt ttaatcagac cgccaccgcc accggtcgct tatcaagtag cgatccgaac    1740
ttgcagaata ttccggtgcg taccccgtta ggtcagcgca ttcgtcgtgc ctttattgca    1800
gaagaaggtt ggttattagt tgcattagat tatagtcaga ttgaactgcg tgtgttagcc    1860
catctgagcg gcgacgaaaa tctgattcgt gtgtttcagg aaggtcgcga tattcatacc    1920
gaaaccgcct cttggatgtt tggtgttccg cgcgaagcag ttgatccgtt aatgcgccgt    1980
gcagccaaaa ccattaattt tggtgtgctg tatggtatga gcgcacatcg cctgtcacag    2040
gaactggcaa ttccgtatga agaagcacag gcctttattg aacgctattt tcagtcttt    2100
ccgaaagttc gcgcatggat tgaaaaaacc ttagaagaag gtcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctgagtg aaatgggtgc acgaatgctg    2340
ttacaggttc atgatgaatt agttctgaa gccccgaaag aacgcgccga agcagttgca    2400
cgtctggcca agaagtgat ggaaggtgtg tatccgttag cagttccgtt agaagtggaa    2460
gtgggtattg tgaagattg gctgagcgcc aagaaaggtt ctggcagttc aggtcatcac    2520
caccatcatc actaa                                                     2535

SEQ ID NO: 56          moltype = AA  length = 844
FEATURE                Location/Qualifiers
REGION                 1..844
                       note = Description of Artificial Sequence: Synthetic
                       polypeptide
source                 1..844
                       mol_type = protein
                       organism = synthetic construct
SEQUENCE: 56
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPDTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 57          moltype = DNA  length = 2535
FEATURE                Location/Qualifiers
misc_feature           1..2535
                       note = Description of Artificial Sequence: Synthetic
                       polynucleotide
source                 1..2535
                       mol_type = other DNA
                       organism = synthetic construct
SEQUENCE: 57
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag gtcgcgcccc gacccccgaa gattttccgc gtcagctggc cttaattaaa    300
gaattagttg acttgctggg cttagcacgt ctggaagttc cgggctatga agcagatgat    360
gttttagcct cactgGccaa aaaagccgaa aagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt tacgtccgga tcagtgggca    540
gattatcgtg cactgaccgg tgacgaatca gataatctgc cgggcgttaa aggtattggt    600
gaaaaaaccg cccgcaaatt attagaagaa tgggggtagtc tggaagcatt actgaaaaat    660
ctggatcgcc tgaaaccggc aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag cgccctttgt ggggctttgtg ctgagtagga aagaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagaccgag tgttctggca   1080
ttaagggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcgggca acgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagtta cagaagaaat tgcacgctta gaagccgaag ttttcgctt agcaggtcat   1440
ccgtttaact aaatagtcg cgatcagctg gaagggttc tgtttgatga attaggcctg   1500
ccggcaattg gcaagaccga aaaaaccggt aaacgctcta cctcagccgc agttctggaa   1560
```

```
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catacccgtt ttaatcagac cgccaccgcc accggtcgct tatcaagtag cgatccgaac   1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgatacag   2040
gaactggcaa ttccgtatga agaagcacag gcctttattt aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt aaatcagtg    2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                    2535

SEQ ID NO: 58           moltype = AA  length = 844
FEATURE                 Location/Qualifiers
REGION                  1..844
                        note = Description of Artificial Sequence: Synthetic
                         polypeptide
source                  1..844
                        mol_type = protein
                        organism = synthetic construct
SEQUENCE: 58
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERRLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLIQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                                844

SEQ ID NO: 59           moltype = DNA  length = 2535
FEATURE                 Location/Qualifiers
misc_feature            1..2535
                        note = Description of Artificial Sequence: Synthetic
                         polynucleotide
source                  1..2535
                        mol_type = other DNA
                        organism = synthetic construct
SEQUENCE: 59
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga agatggcgat   180
gcagtgattg ttgtgtttga tgccaaagcc ccgagctttc gtcatgaagc ctatggcggc   240
tacaaagcag gtcgcgcccc gacccccgaa gattttccgc gtcagctggc cttaattaaa   300
gaattagttg acttgctggg cttagcacgt ctggaagttc cgggctatga agcagatgat   360
gttttagcct cactggccaa aaaagccgaa aaagaaggct atgaagttcg cattctgacc   420
gcagataagg atctgtatca gctgctgagc gatcgtattc atgtgttaca tccggaaggc   480
tatctgatta ccccggcatg gttatgggaa aaatatggtt tacgtccgga tcagtgggca   540
gattatcgtg cactgaccgg tgacgaatca gataatctgc cgggcgttaa aggtattggt   600
gaaaaaaccg cccggaaatt attagaagaa tggggtagtc tggaagcatt actgaaaaat   660
ctggatcgcc tgaaaccggc aattcgcgaa aaaattttag cccacatgga tgacttaaaa   720
ctgtcttggg atctggccaa agtgcgtacc gatctgccgt tagaagttga ttttgccaaa   780
cgtcgcgaac cggatcgtga acgcctacga gcctttctgg aacgcttaga atttggctca   840
ctgttacatg aatttggctt actggaatct ccgaaagcat tagaagaagc cccgtggccg   900
ccgccggaag cgcctttgt  gggctttgtg ctgagtagga agaaaccgat gtgggcagac   960
ttgctggccc tggccgcagc acgcggcggt cgcgttcatc gtgccccgga accgtacaaa  1020
gccctgcgtg acctgaaaga agcacgcggg ttattagcca aagacctgag tgttctggca  1080
ttaagggaag gcttaggcct gccgccgggc gatgatccga tgctgctggc ctatctgctt  1140
gacccgagta taccaccccc ggaaggcgtt gcacgtcgct atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtgg aacgcccgtt agcggaagtg  1320
ctggcacaca tggaagccac cggtgtgcgc ttagatgttg catatctgcg tgccctgtct  1380
ctggaagttg cagaagaaat tgcacgctta agccgaaag tttttcgctt agcaggtcat  1440
ccgtttaact aaaatagtcg cgatcagctg gaaagggttc tgtttgatga attaggcctg  1500
ccggcaattg gcaagaccga aaaaaccggt aacgctctca cctcagccgc agttctggaa  1560
gccctgcgcg aagcccatcc gattgttgaa aaaattttac agtatcgtga actgaccaaa  1620
```

```
ctgaaatcta cctatattga tccgttaccg gatctaattc atccgcgtac cggtcgctta  1680
catacccgtt ttaatcagac cgccaccgcc accggtcgct tatcaagtag cgatccgaac  1740
ttgcagaata ttccggtgcg tacccccgtta ggtcagcgca ttcgtcgtgc ctttattgca  1800
gaagaaggtt ggttattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcgcacatcg cctgtcacag  2040
gaactggcaa ttccgtatga agaagcacag gcctttattg aacgctattt tcagtctttt  2100
ccgaaagttc gcgcatggat tgaaaaaacc ttagaagaag gtcgtcgtcg cggctatgtg  2160
gaaaccctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
atgaaactgg caatggttaa actgtttccg cgcctggaag aaatgggtgc acgaatgctg  2340
ttacaggttc atgatgaatt agtttctgaa gccccgaaag aacgcgccga agcagttgca  2400
cgtctggcca aagaagtgat ggaagtgtg tatccgttag cagttccgtt agaagtgaa   2460
gtgggtattg gtgaagattg gctgagcgcc aaagaaggt ctggcagttc aggtcatcac   2520
caccatcatc actaa                                                   2535

SEQ ID NO: 60          moltype = AA   length = 844
FEATURE                Location/Qualifiers
REGION                 1..844
                       note = Description of Artificial Sequence: Synthetic
                       polypeptide
source                 1..844
                       mol_type = protein
                       organism = synthetic construct
SEQUENCE: 60
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD  120
VLASLAKKAE KEGYEVRILT ADKDLYQLLS DRIHVLHPEG YLITPAWLWE KYGLRPDQWA  180
DYRALTGDES DNLPGVKGIG EKTARKLLEE WGSLEALLKN LDRLKPAIRE KILAHMDDLK  240
LSWDLAKVRT DLPLEVDFAK RREPDRERLR AFLERLEFGS LLHEFGLLES PKALEEAPWP  300
PPEGAFVGFV LSRKEPMWAD LLALAAARGG RVHRAPEPYK ALRDLKEARG LLAKDLSVLA  360
LREGLGLPPG DDPMLLAYLL DPSNTTPEGV ARRYGGEWTE EAGERAALSE RLFANLWGRL  420
EGEERLLWLY REVERPLSAV LAHMEATGVR LDVAYLRALS LEVAEEIARL EAEVFRLAGH  480
PFNLNSRDQL ERVLFDELGL PAIGKTEKTG KRSTSAAVLE ALREAHPIVE KILQYRELTK  540
LKSTYIDPLP DLIHPRTGRL HTRFNQTATA TGRLSSSDPN LQNIPVRTPL GQRIRRAFIA  600
EEGWLLVALD YSQIELRVLA HLSGDENLIR VFQEGRDIHT ETASWMFGVP REAVDPLMRR  660
AAKTINFGVL YGMSAHRLSQ ELAIPYEEAQ AFIERYFQSF PKVRAWIEKT LEEGRRRGYV  720
ETLFGRRRYV PDLEARVKSV REAAERMAFN MPVQGTAADL MKLAMVKLFP RLEEMGARML  780
LQVHDELVSE APKERAEAVA RLAKEVMEGV YPLAVPLEVE VGIGEDWLSA KEGSGSSGHH  840
HHHH                                                               844

SEQ ID NO: 61          moltype = DNA   length = 2535
FEATURE                Location/Qualifiers
misc_feature           1..2535
                       note = Description of Artificial Sequence: Synthetic
                       polynucleotide
source                 1..2535
                       mol_type = other DNA
                       organism = synthetic construct
SEQUENCE: 61
atgcgcggta tgctgccgtt atttgaaccg aaaggtcgtg tgctgctggt tgatggtcat   60
cacttagcat atcgtacctt tcatgccctg aaaggcctga ccacctctcg cggcgaaccg  120
gttcaggcag tgtatggttt tgccaaatca ctgctgaaag cattaaaaga agatggcgat  180
gcagtgattg ttgtgtttga tgccaaaagc ccgagctttc gtcatgaagc ctatggcggc  240
tacaaagcag gtcgcgcccc gaccccggaa gattttccgc gtcagctggc cttaattaaa  300
gaattagttg acttgctggg cttagcacgt ctggaagttc cgggctatga agcagatgat  360
gttttagcct cactggccaa aaaagccgaa aagaaggct atgaagttcg cattctgacc   420
gcagataagg atctgtatca gctgctgagc gatcgtatte atgtgttaca tccggaaggc  480
tatctgatta ccccggcatg gttatgggaa aaatatggtt tacgtccgga tcagtgggca  540
gattatcgtg cactgaccgg tgacaaatca gataatctgc cgggcgttaa aggtattggt  600
gaaaaaaccg cccggaaatt attagaagaa tggggtagtc tggaagcatt actgaaaaat  660
ctggatcgcc tgaaaccggc aattcgcgaa aaaattttag cccacatgga tgacttaaaa  720
ctgtcttggg atctggccaa agtgcgtacc gatctgccgt tagaagttga ttttgccaaa  780
cgtcgcgaac cggatcgtga acgcctacga gcctttctgg aacgcttaga atttggctca  840
ctgttacatg aatttggctt actggaatct ccgaaagcat taagaagagc cgtggccg    900
ccgccggaag gcgcctttgt gggctttgtg ctgagtagga agaaccgat gtgggcagac  960
ttgctggccc tggccgcagc acgcggcggt cgcgttcatc gtgccccgga accgtacaaa  1020
gccctgcgtg acctgaaaga agcacgcggt ttattagcca aagacctgag tgttctggca  1080
ttaagggaag gcttaggcct gccgccgggc gatgatccga tgctgctggc ctatctgctt  1140
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtgg aacgtccgct gagcgcagtg  1320
ctggcacaca tggaagccac cggtgtgcgc ttagatgttg catatctgcg tgccctgtct  1380
ctggaagttc agaagaaat tgcacgctta gaagccgaag ttttttcgct agcaggtcat   1440
ccgtttaact aaatagtcg cgatcagctg gaaagggttc tgtttgatga attaggcctg  1500
ccggcaattg gcaagaccaa aaaaaccggt aaacgctcta cctcagccgc agttctggaa  1560
gccctgcgcg aagcccatcc gattgttgaa aaaatttac agtatcgtga actgaccaaa  1620
ctgaaatcta cctatattga tccgttaccg gatctaattc atccgcgtac cggtcgctta  1680
```

```
cataccegtt ttaatcagac egccaccgcc accggtegct tatcaagtag egateegaac   1740
ttgcagaata ttccggtgcg tacccegtta ggtcagcgca ttcgtegtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag tcgtcgtcg cggctatgtg   2160
gaaaccctgt ttggtcgtcg tcgctatgtt ccggatctgg aagcgagagt taaatcagtg   2220
cgtaaagccg ccgaacgcat ggcctttaat atgccggttc agggaacggc agctgaccct   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                   2535

SEQ ID NO: 62          moltype = AA  length = 844
FEATURE                Location/Qualifiers
REGION                 1..844
                       note = Description of Artificial Sequence: Synthetic
                       polypeptide
source                 1..844
                       mol_type = protein
                       organism = synthetic construct
SEQUENCE: 62
MRGMLPLFEP KGRVLLVDGH HLAYRTFHAL KGLTTSRGEP VQAVYGFAKS LLKALKEDGD   60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHVLHPEG YLITPAWLWE KYGLRPDQWA   180
DYRALTGDKS DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTKKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV RKAAERMAFN MPVQGTAADL MKLAMVKLFP RLEEMGARML   780
LQVHDELVLE APKERAEAVA RLAKEVMEGV YPLAVPLEVE VGIGEDWLSA KEGSGSSGHH   840
HHHH                                                               844

SEQ ID NO: 63          moltype = DNA  length = 20
FEATURE                Location/Qualifiers
misc_feature           1..20
                       note = Description of Artificial Sequence: Synthetic primer
source                 1..20
                       mol_type = other DNA
                       organism = synthetic construct
SEQUENCE: 63
ttacaaacat tggccgcaaa                                               20

SEQ ID NO: 64          moltype = DNA  length = 18
FEATURE                Location/Qualifiers
misc_feature           1..18
                       note = Description of Artificial Sequence: Synthetic primer
source                 1..18
                       mol_type = other DNA
                       organism = synthetic construct
SEQUENCE: 64
gcgcgacatt ccgaagaa                                                 18

SEQ ID NO: 65          moltype = DNA  length = 23
FEATURE                Location/Qualifiers
misc_feature           1..23
                       note = Description of Artificial Sequence: Synthetic probe
source                 1..23
                       mol_type = other DNA
                       organism = synthetic construct
SEQUENCE: 65
acaatttgcc cccagcgctt cag                                           23
```

PROCESS OF PROBE QPCR USING TAQ DNA POLYMERASE MUTANTS

RELATED APPLICATIONS

This application is a divisional application of U.S. application Ser. No. 17/470,557, filed, 9/9/2021, and issued as a US Patent, which claims priority to Provisional No. 63/088,546, filed Oct. 7, 2020.

SEQUENCE LISTING

The instant application contains a Sequence Listing which has been submitted electronically in XML file format and is hereby incorporated by reference in its entirety. Said XML copy, created on Jun. 16, 2023, is named ABCL-QPCR_SL.txt and is 189,197 bytes in size.

BACKGROUND

Taq DNA polymerase is commonly used in molecular biology for extending nucleic acid amplicons in polymerase chain reactions (PCR). In PCR, designated segments of DNA (amplicons) are amplified by the repeated cycling of three steps: denaturation, annealing, and elongation/extension of the amplicon. With qualitative, real-time PCR (qPCR), fluorescent signal generated through dyes or probes allows for data collection during PCR cycling so that target amplification can be measured and recorded. Probe-based chemistries utilize fluorescently labeled, target-specific probes which only release a reporter dye when bound to target sequence, allowing for real-time detection of target amplification as fluorescent signal intensity increases.

Two inherent enzyme activities of Taq DNA polymerase, DNA polymerization and 5' to 3' exonuclease activity, are the basis of probe-based qPCR. As qPCR probe amplicons are generally very short, wild type Taq polymerization activity is normally enough to extend those probe amplicons even at very short extension intervals of one second. However, the rate-limiting factor in probe-based qPCR is the 5' to 3' exonuclease activity responsible for releasing the reporter signal. Wild type Taq DNA polymerase is unable to cleave the probe from its attached fluorophore within one second, irrespective of polymerization during that period, thus inhibiting detection. Thus what is needed are Taq DNA polymerase mutants having increased efficiency of Taq polymerase 5' to 3' exonuclease activity and which allow for detection of rapid amplification during qPCR.

SUMMARY

Taq DNA polymerase mutants of the invention exhibit enhanced efficiency in qPCR compared to the wild type Taq DNA polymerase. Taq DNA polymerase mutants of the invention were engineered, characterized, and selected via probe-based qualitative, real-time PCR (qPCR) with a cycling protocol using a rapid extension time (one second per cycle). A number of suitable mutants were found, including: V62S, V64S, A70F, F73A, A77F, P253G, E255K, D257R, A259F, A271F, L288S, E289K, S357I, L361S, L376S, P382G, T385I, G418P, R419D, E421K, L461S, A472F, E497K, L498S, E524K, D551R, R556D, S679I, L789S, E189K/E507K/E742K (See Sequence Listing Guide below, where the DNA and protein sequence for each mutant is indicated by the associated listing number).

Compared to traditional, longer protocols for wild-type enzyme, the engineered mutants' ability to detect rapid extension significantly decreases the total run time required for a qPCR run, significantly boosting the efficiency of detecting target nucleic acids with qPCR or real time qPCR. This would be a significant economic advantage for use of the mutants.

Taq DNA polymerase mutants of the invention can be used in conventional qPCR assays, including for gene expression analysis and other DNA quantification.

BRIEF DESCRIPTION OF THE DRAWINGS 1A to 1II are each amplification plots showing a probe qPCR signal comparisons of Taq DNA wild type and a Taq DNA polymerase mutant which is indicated at the bottom for each plot. For each plot, the X axis is the cycle number and the Y axis is the change in fluorescent signal detected (DR), representing the indicated mutant's the change in fluorescence throughout the cycling protocol, with dots indicating specific measured signal value per cycle. All detection threshold lines are fixed at 0.02. The qPCR protocol for all mutants was run in duplicate, as indicated in panels where two distinct sets of dots and lines can be seen.

Sequence Listing Guide

SEQ ID NO: 1 is the DNA sequence of Wild Type Taq DNA polymerase with a C terminal Histag.
SEQ ID NO: 2 is the protein sequence of Wild Type Taq DNA polymerase with a C terminal Histag.
SEQ ID NO: 3 is the DNA sequence of mutant (V62S) Taq DNA polymerase with a C terminal Histag.
SEQ ID NO: 4 is the protein sequence of mutant (V62S) Taq DNA polymerase with a C terminal Histag.
SEQ ID NO: 5 is the DNA sequence of mutant (V64S) Taq DNA polymerase with a C terminal Histag.
SEQ ID NO: 6 is the protein sequence of mutant (V64S) Taq DNA polymerase with a C terminal Histag.
SEQ ID NO: 7 is the DNA sequence of mutant (A70F) Taq DNA polymerase with a C terminal Histag.
SEQ ID NO: 8 is the protein sequence of mutant (A70F) Taq DNA polymerase with a C terminal Histag.
SEQ ID NO: 9 is the DNA sequence of mutant (F73A) Taq DNA polymerase with a C terminal Histag.
SEQ ID NO: 10 is the protein sequence of mutant (F73A) Taq DNA polymerase with a C terminal Histag.
SEQ ID NO: 11 is the DNA sequence of mutant (A77F) Taq DNA polymerase with a C terminal Histag.
SEQ ID NO: 12 is the protein sequence of mutant (A77F) Taq DNA polymerase with a C terminal Histag.
SEQ ID NO: 13 is the DNA sequence of mutant (P253G) Taq DNA polymerase with a C terminal Histag.
SEQ ID NO: 14 is the protein sequence of mutant (P253G) Taq DNA polymerase with a C terminal Histag.
SEQ ID NO: 15 is the DNA sequence of mutant (E255K) Taq DNA polymerase with a C terminal Histag.
SEQ ID NO: 16 is the protein sequence of mutant (E255K) Taq DNA polymerase with a C terminal Histag.
SEQ ID NO: 17 is the DNA sequence of mutant (D257R) Taq DNA polymerase with a C terminal Histag.
SEQ ID NO: 18 is the protein sequence of mutant (D257R) Taq DNA polymerase with a C terminal Histag.
SEQ ID NO: 19 is the DNA sequence of mutant (A259F) Taq DNA polymerase with a C terminal Histag.
SEQ ID NO: 20 is the protein sequence of mutant (A259F) Taq DNA polymerase with a C terminal Histag.
SEQ ID NO: 21 is the DNA sequence of mutant (A271F) Taq DNA polymerase with a C terminal Histag.
SEQ ID NO: 22 is the protein sequence of mutant (A271F) Taq DNA polymerase with a C terminal Histag.

SEQ ID NO: 23 is the DNA sequence of mutant (L288S) Taq DNA polymerase with a C terminal Histag.

SEQ ID NO: 24 is the protein sequence of mutant (L288S) Taq DNA polymerase with a C terminal Histag.

SEQ ID NO: 25 is the DNA sequence of mutant (E289K) Taq DNA polymerase with a C terminal Histag.

SEQ ID NO: 26 is the protein sequence of mutant (E289K) Taq DNA polymerase with a C terminal Histag.

SEQ ID NO: 27 is the DNA sequence of mutant (S357I) Taq DNA polymerase with a C terminal Histag.

SEQ ID NO: 28 is the protein sequence of mutant (S357I) Taq DNA polymerase with a C terminal Histag.

SEQ ID NO: 29 is the DNA sequence of mutant (L361S) Taq DNA polymerase with a C terminal Histag.

SEQ ID NO: 30 is the protein sequence of mutant (L361S) Taq DNA polymerase with a C terminal Histag.

SEQ ID NO: 31 is the DNA sequence of mutant (L376S) Taq DNA polymerase with a C terminal Histag.

SEQ ID NO: 32 is the protein sequence of mutant (L376S) Taq DNA polymerase with a C terminal Histag.

SEQ ID NO: 33 is the DNA sequence of mutant (P382G) Taq DNA polymerase with a C terminal Histag.

SEQ ID NO: 34 is the protein sequence of mutant (P382G) Taq DNA polymerase with a C terminal Histag.

SEQ ID NO: 35 is the DNA sequence of mutant (T385I) Taq DNA polymerase with a C terminal Histag.

SEQ ID NO: 36 is the protein sequence of mutant (T385I) Taq DNA polymerase with a C terminal Histag.

SEQ ID NO: 37 is the DNA sequence of mutant (G418P) Taq DNA polymerase with a C terminal Histag.

SEQ ID NO: 38 is the protein sequence of mutant (G418P) Taq DNA polymerase with a C terminal Histag.

SEQ ID NO: 39 is the DNA sequence of mutant (R419D) Taq DNA polymerase with a C terminal Histag.

SEQ ID NO: 40 is the protein sequence of mutant (R419D) Taq DNA polymerase with a C terminal Histag.

SEQ ID NO: 41 is the DNA sequence of mutant (E421K) Taq DNA polymerase with a C terminal Histag.

SEQ ID NO: 42 is the protein sequence of mutant (E421K) Taq DNA polymerase with a C terminal Histag.

SEQ ID NO: 43 is the DNA sequence of mutant (L461S) Taq DNA polymerase with a C terminal Histag.

SEQ ID NO: 44 is the protein sequence of mutant (L461S) Taq DNA polymerase with a C terminal Histag.

SEQ ID NO: 45 is the DNA sequence of mutant (A472F) Taq DNA polymerase with a C terminal Histag.

SEQ ID NO: 46 is the protein sequence of mutant (A472F) Taq DNA polymerase with a C terminal Histag.

SEQ ID NO: 47 is the DNA sequence of mutant (E497K) Taq DNA polymerase with a C terminal Histag.

SEQ ID NO: 48 is the protein sequence of mutant (E497K) Taq DNA polymerase with a C terminal Histag.

SEQ ID NO: 49 is the DNA sequence of mutant (L498S) Taq DNA polymerase with a C terminal Histag.

SEQ ID NO: 50 is the protein sequence of mutant (L498S) Taq DNA polymerase with a C terminal Histag.

SEQ ID NO: 51 is the DNA sequence of mutant (E524K) Taq DNA polymerase with a C terminal Histag.

SEQ ID NO: 52 is the protein sequence of mutant (E524K) Taq DNA polymerase with a C terminal Histag.

SEQ ID NO: 53 is the DNA sequence of mutant (D551R) Taq DNA polymerase with a C terminal Histag.

SEQ ID NO: 54 is the protein sequence of mutant (D551R) Taq DNA polymerase with a C terminal Histag.

SEQ ID NO: 55 is the DNA sequence of mutant (R556D) Taq DNA polymerase with a C terminal Histag.

SEQ ID NO: 56 is the protein sequence of mutant (R556D) Taq DNA polymerase with a C terminal Histag.

SEQ ID NO: 57 is the DNA sequence of mutant (S679I) Taq DNA polymerase with a C terminal Histag.

SEQ ID NO: 58 is the protein sequence of mutant (S679I) Taq DNA polymerase with a C terminal Histag.

SEQ ID NO: 59 is the DNA sequence of mutant (L789S) Taq DNA polymerase with a C terminal Histag.

SEQ ID NO: 60 is the protein sequence of mutant (L789S) Taq DNA polymerase with a C terminal Histag.

SEQ ID NO: 61 is the DNA sequence of mutant (E189K/E507K/E742K) Taq DNA polymerase with a C terminal Histag.

SEQ ID NO: 62 is the protein sequence of mutant (E189K/E507K/E742K) Taq DNA polymerase with a C terminal Histag.

SEQ ID NO: 63 is the DNA sequence of the 2019-nCoV_N2 Forward Primer.

SEQ ID NO: 64 is the DNA sequence of the 2019-nCoV_N2 Reverse Primer.

SEQ ID NO: 64 is the DNA sequence of the 2019-nCoV_N2 Probe.

The respective DNA and protein sequences of wild type Taq DNA polymerase and each mutant above, with a C terminal Histag, is shown in the sequence listing attached.

DETAILED DESCRIPTION

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

The term "labeled probe" refers to a labeling probe used in an amplification reaction, typically for quantitative or qPCR analysis, as well as end-point analysis. Such labeling probes may be used to monitor the amplification of the target polynucleotide, and are suitable for monitoring the amount of amplicon(s) produced as a function of time. Such oligonucleotide labeling probes include, but are not limited to, the 5'-exonuclease assay TaqMan labeling probes (see U.S. Pat. No. 5,538,848), various stem-loop molecular beacons (see e.g., U.S. Pat. Nos. 6,103,476 and 5,925,517, stemless or linear beacons (WO 99/21881), PNA Molecular Beacons (see, e.g., U.S. Pat. Nos. 6,355,421 and 6,593,091), linear PNA beacons, non-FRET labeling probes (see, e.g., U.S. Pat. No. 6,150,097), Sunrise/Amplifluor labeling probes (U.S. Pat. No. 6,548,250), stem-loop and duplex Scorpion labeling probes (U.S. Pat. No. 6,589,743), bulge loop labeling probes (U.S. Pat. No. 6,590,091), pseudo knot labeling probes (U.S. Pat. No. 6,589,250), cyclicons (U.S. Pat. No. 6,383,752), hairpin labeling probes (U.S. Pat. No. 6,596,490), peptide nucleic acid (PNA) light-up labeling probes, self-assembled nanoparticle labeling probes, and ferrocene-modified labeling probes described, for example, in U.S. Pat. No. 6,485,901. Labeling probes can also comprise black hole quenchers (Biosearch), Iowa Black (IDT), QSY quencher (Molecular Labeling probes), and Dabsyl and Dabcel sulfonate/carboxylate Quenchers (Epoch). Labeling probes can also comprise two labeling probes, wherein for example a fluorophore is on one probe, and a quencher on the other, wherein hybridization of the two labeling probes together on a target quenches the signal, or wherein hybridization on target alters the signal signature via a change in fluorescence. Labeling probes can also comprise sulfonate derivatives of fluorescenin dyes with a sulfonic acid group instead of the carboxylate group, phosphoramidite forms of fluorescein, phosphoramidite forms of CY 5 (available from Amersham).

The term "sample" refers to biological samples from any source which include nucleic acid or DNA.

The term "real time quantitative PCR" and "real time qPCR", is used interchangeably with the term "quantitative PCR" (abbreviated "qPCR"), and refers to a method for simultaneous amplification, detection, and quantification of a target polynucleotide using labeled probes during PCR and further includes the protocols in the examples herein and such methods as TaqMan, SYBR Green assays, and the like; whether in a system performing quantitative real-time PCR or semi-quantitative real-time PCR.

The term "target," refers to a polynucleotide sequence that is sought to be amplified and can exist in the presence of other nucleic acid molecules or within a larger nucleic acid molecule or in a sample. The target polynucleotide can be obtained from any source, and can DNA or cDNA from RNA, or can be methylated, non-methylated, or both.

The term "threshold cycle" or "C T" is defined as a fractional cycle number at which a reporter signal rises above a threshold value, including where DNA quantification by real-time PCR relies on plotting fluorescence against the number of cycles on a logarithmic scale. A threshold for detection of DNA-based fluorescence is, preferably, set 3-5 times of the standard deviation of the signal noise above background. The number of cycles at which the fluorescence exceeds the threshold is called the threshold cycle (Ct) or quantification cycle (Cq).

The term "threshold" or "threshold value" is defined as the reporter signal value that is used for calculation of threshold cycle ($C_T$).

The term "reporter signal" is defined as the signal generated by a PCR product reporter (typically a dye or a labeled probe) which is correlated with the concentration of PCR product, in an assay for measuring biological data, including but not limited to data for cycling reactions. Examples of suitable data include but are not limited to, fluorescent signal data, optical signal data, magnetic signal data, and electronic signal data. Suitable assays include DNA quantification by qPCR. The reporter signal can be generated by a DNA-binding or intercalating dye (e.g. SYBR Green or EvaGreen) that binds to all double-stranded (ds) DNA in PCR, increasing the fluorescence quantum yield of the dye, and leading to an increase in fluorescence intensity measured at each cycle. The assay should be adjusted so that the increasing signal intensity does not interfere with, or prevent, accurate quantification of the target.

The mutant Taq polymerase of the invention is suited to improved efficiency qPCR where the cycling includes using a rapid extension time of one second per cycle. It can be used with the commonly employed method of varying primers and templates for increasing the efficiency of target amplification, to find the most efficient primer-template combination together with the most efficient mutant Taq polymerase of the invention, as assessed in a titration experiment with serial dilutions of DNA template to create a standard curve of the change in ($C_T$), as determined from reporter signal, with each dilution. The slope of the linear regression is then used to determine the efficiency of amplification, which is 100% if a dilution of 1:2 results in a ($C_T$) difference of 1.

The efficiency of qPCR can also be determined by mechanism-based qPCR quantification methods, which do not require a standard curve for quantification. Methods such as MAK2 (see Boggy G, Woolf P J (2010); Ravasi T (ed.). "A Mechanistic Model of PCR for Accurate Quantification of Quantitative PCR Data" PLOS ONE 5 (8): e12355) have been shown to have equal or better quantitative performance to standard curve methods. These mechanism-based methods use knowledge about the polymerase amplification process to generate estimates of the original sample concentration and amplification.

Real-time or qPCR with the mutant Taq DNA polymerase of the invention can also be used to quantify nucleic acids, and monitor gene expression, by relative quantification and absolute quantification. Absolute quantification gives the exact number of target DNA molecules by comparison with DNA standards using a calibration curve; which necessitates that the PCR of the sample and the standard have the same amplification efficiency. The mutant Taq DNA polymerase of the invention provides a faster cycle time with a consistent and increased efficiency, making them suitable for absolute quantification. The same properties of the mutant Taq DNA polymerase of the invention also makes them well-suited relative quantification.

Diagnostic qualitative PCR is applied to rapidly detect nucleic acids that are diagnostic of, for example, infectious diseases, cancer and genetic abnormalities. The properties of the mutant Taq DNA polymerase of the invention in qPCR assays allows significantly improved diagnosis of infectious diseases, newly emerging diseases, such as new strains of flu and coronavirus, and in diagnostic tests.

Real time or qPCR with the mutant Taq DNA polymerase of the invention can also be used to assay gene expression and provide meaningful information relating to food safety, food spoilage and fermentation and microbial risk assessment of water quality (drinking and recreational waters) and in public health protection.

Real time or qPCR with the mutant Taq DNA polymerase of the invention may also be used to amplify taxonomic or functional markers of genes in environmentally relevant samples to help determine, e.g., the amount of microorganisms in a sample, and/or, can identify different families, genera, or species based on the marker. Real time or qPCR with the mutant Taq DNA polymerase of the invention may also be used for functional markers (protein-coding genes) to show gene expression within a community, which may reveal information about the environment.

Real time or qPCR with the mutant Taq DNA polymerase of the invention may also be used to detect agricultural pathogens, including those attacking plant propagules or seedlings. Real time or qPCR with the mutant Taq DNA polymerase of the invention may also be used in systems that allow detection and discrimination of small amounts of pathogens like the Phytophthora ramorum, an oomycete that kills Oaks and other species, even when mixed in with the DNA of the host plant.

Real time or qPCR with the mutant Taq DNA polymerase of the invention may also be used to detect GMOs given the sensitivity and dynamic range offered in detecting associated sequences, using specific primers that amplify not the transgene but the promoter, terminator or even intermediate sequences used during the process of engineering the vector. As the process of creating a transgenic plant normally leads to the insertion of more than one copy of the transgene its quantity can also be assessed with the mutant Taq DNA polymerase of the invention.

The use of qPCR with the mutant Taq DNA polymerase of the invention allows both the quantification and genotyping (characterization of the strain, carried out using melting curves) of a virus. The degree of infection, quantified with the mutant Taq DNA polymerase of the invention as the copies of the viral genome per unit of the patient's tissue, is relevant in many diagnoses.

Examples

In gene expression analysis with the Taq DNA polymerase mutants of the invention, one typically performs RNA extraction form the sample followed by reverse transcription, to generate cDNA as the target. The cDNA target can be efficiently quantified with the Taq DNA polymerase mutants of the invention, and one of the methods describe above, where a reporter signal is monitored for threshold and the C T for the sample(s) is determined.

Production of Mutants

Taq DNA polymerase mutants were generated by conventional inverse PCR mutagenesis. All mutants are sequenced verified, expressed in E. Coli, and purified. A C-terminal His tag was added to all Taq DNA polymerase mutants and the wild type for ease of purification.

Exemplary Probe qPCR

Probe qPCR was performed under the following conditions:

The target for the qPCR was the SARS-Co N gene, 2019-nCoV_N2, published by the United States Center for Disease Control for the CDC 2019-nCoV Real-Time RT-PCR Diagnostic Panel.

Forward Primer: 2019-nCoV_N2 Forward Primer: TTACAAACATTGGCCGCAAA (SEQ ID NO: 63)
Reverse Primer: 2019-nCoV_N2 Reverse Primer: GCGCGACATTCCGAAGAA (SEQ ID NO: 64)
Probe: 2019-nCoV_N2 Probe: FAM-ACA ATT TGC CCC CAG CGC TTC AG-BHQ1 (SEQ ID NO: 65)

Initial target concentration was 10 copies of synthesized Covid 19 N gene per reaction (Twist Bioscience, CA).

Each 20 µl reaction contains 4 µl of 50 ng/µl Taq DNA polymerase, 1 µl of 10 µM Forward primer, 1 µl of 10 µM reverse primer, 1 µl of 5 µM Labelling Probe, 1 µl of 10 copies/µl of Covid 19 N gene, and 2 µl of 10× reaction buffer (which makes final of composition of 20 mM Tris-HCl, 80 mM Tris-Acetate, 10 mM (NH4)2SO4, 10 mM KCl, 2 mM MgSO4, 3 mM Mg-Acetate, 0.1% Triton®-X-100, pH 8.8 @ 25° C.) with water comprising the remaining 10 µl.

The qPCR machine used was the Prime Pro 48 Real-time qPCR machine (Cole-Parmer, UK). The reaction protocol was: 95° C. 30 sec denature, followed by 40 cycles of [95° C. 4 sec annealing, 60° C. 1 sec extension]. Fluorescent signal was collected during each cycle the 60° C. extension step.

Figure 1B:
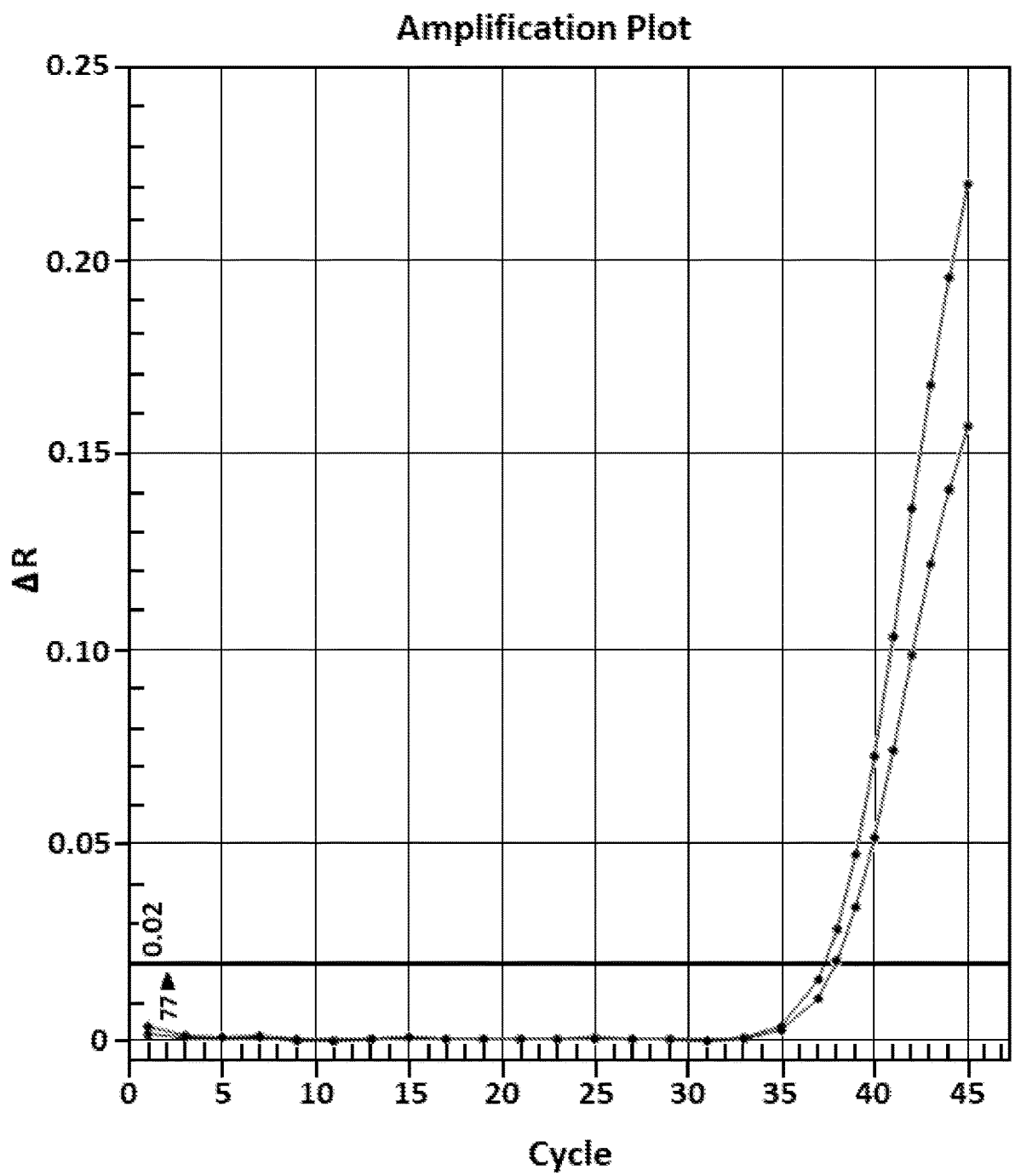
Figure 1C:
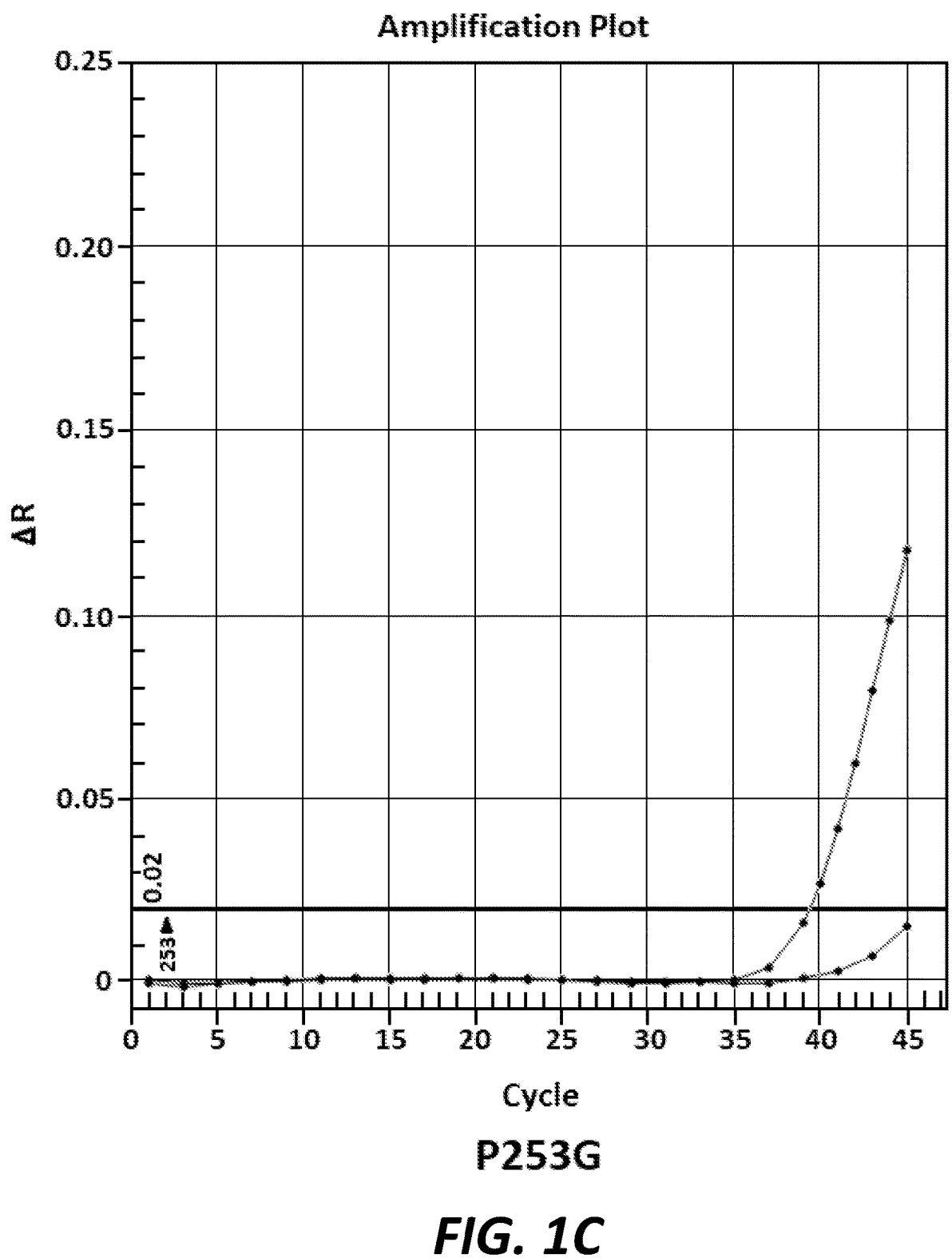
Figure 1D:
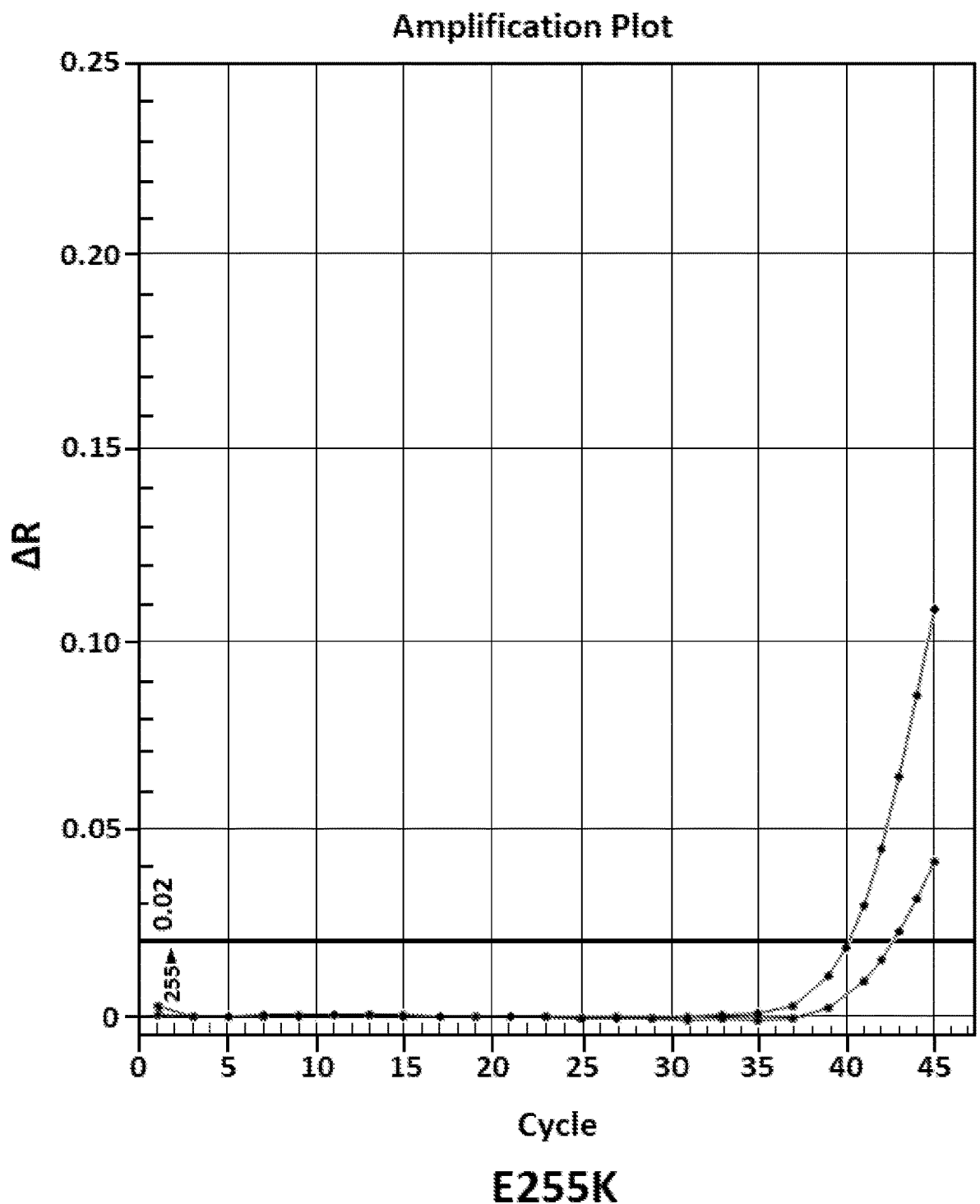
Figure 1E:
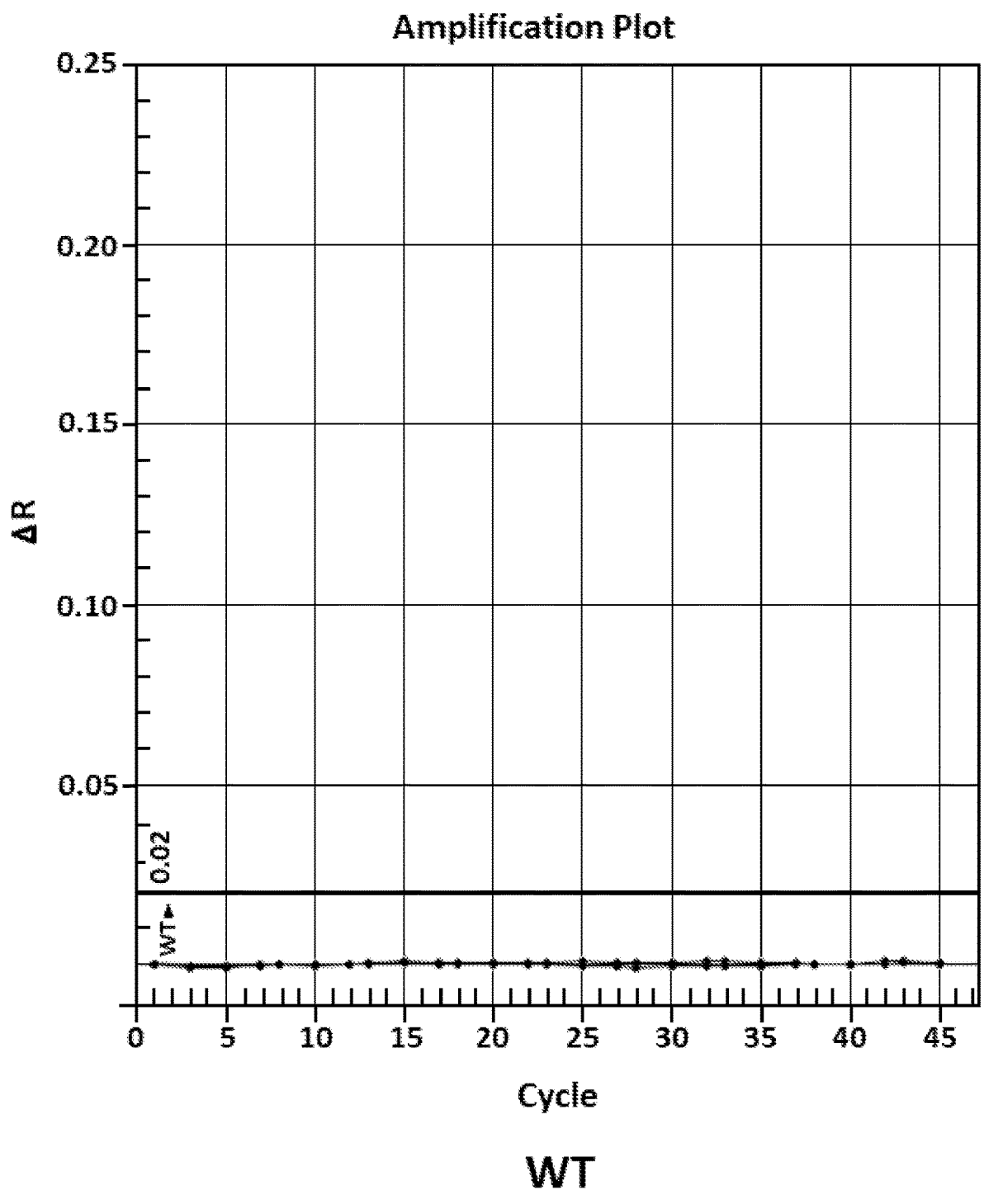
Figure 1F:
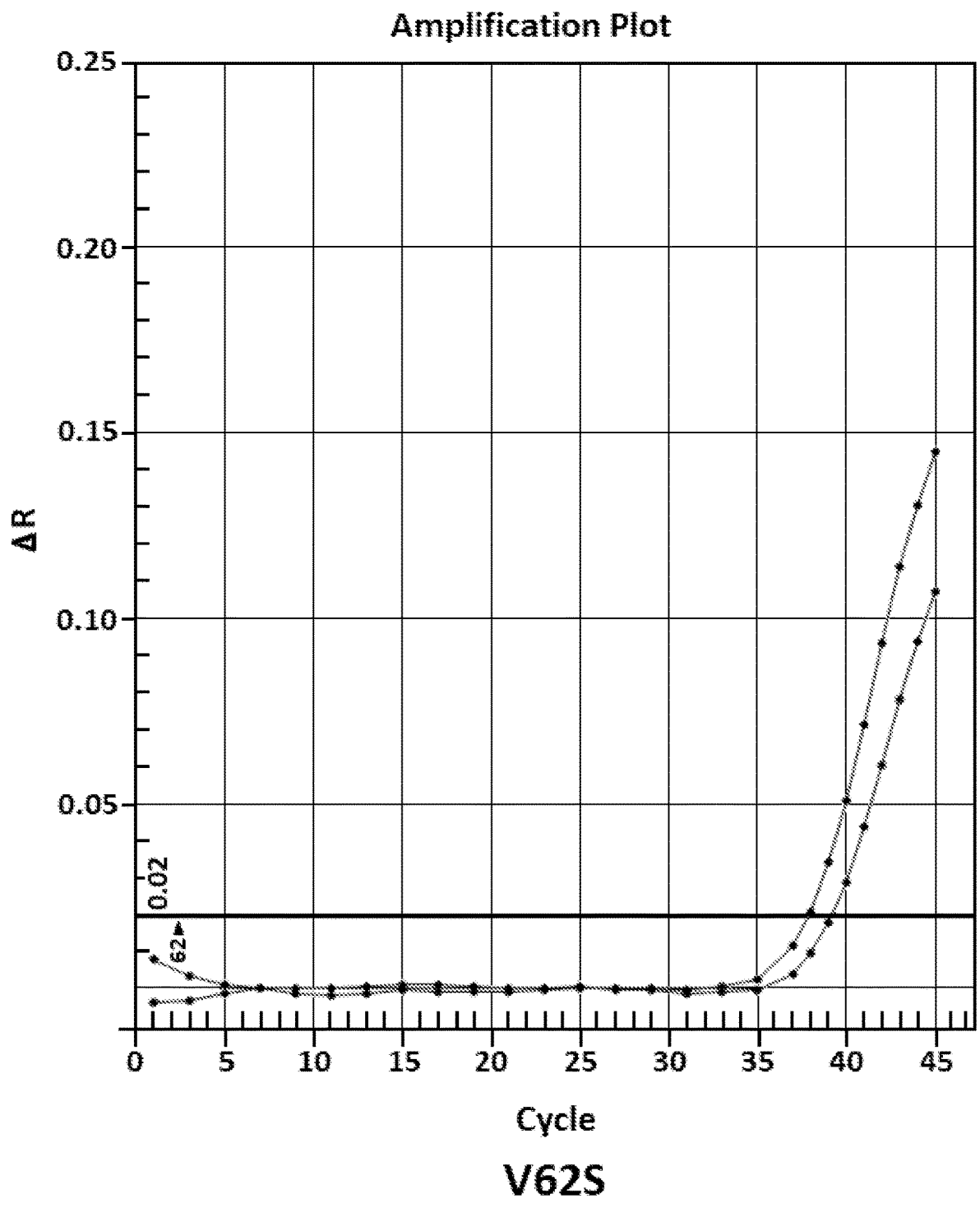
Figure 1G:
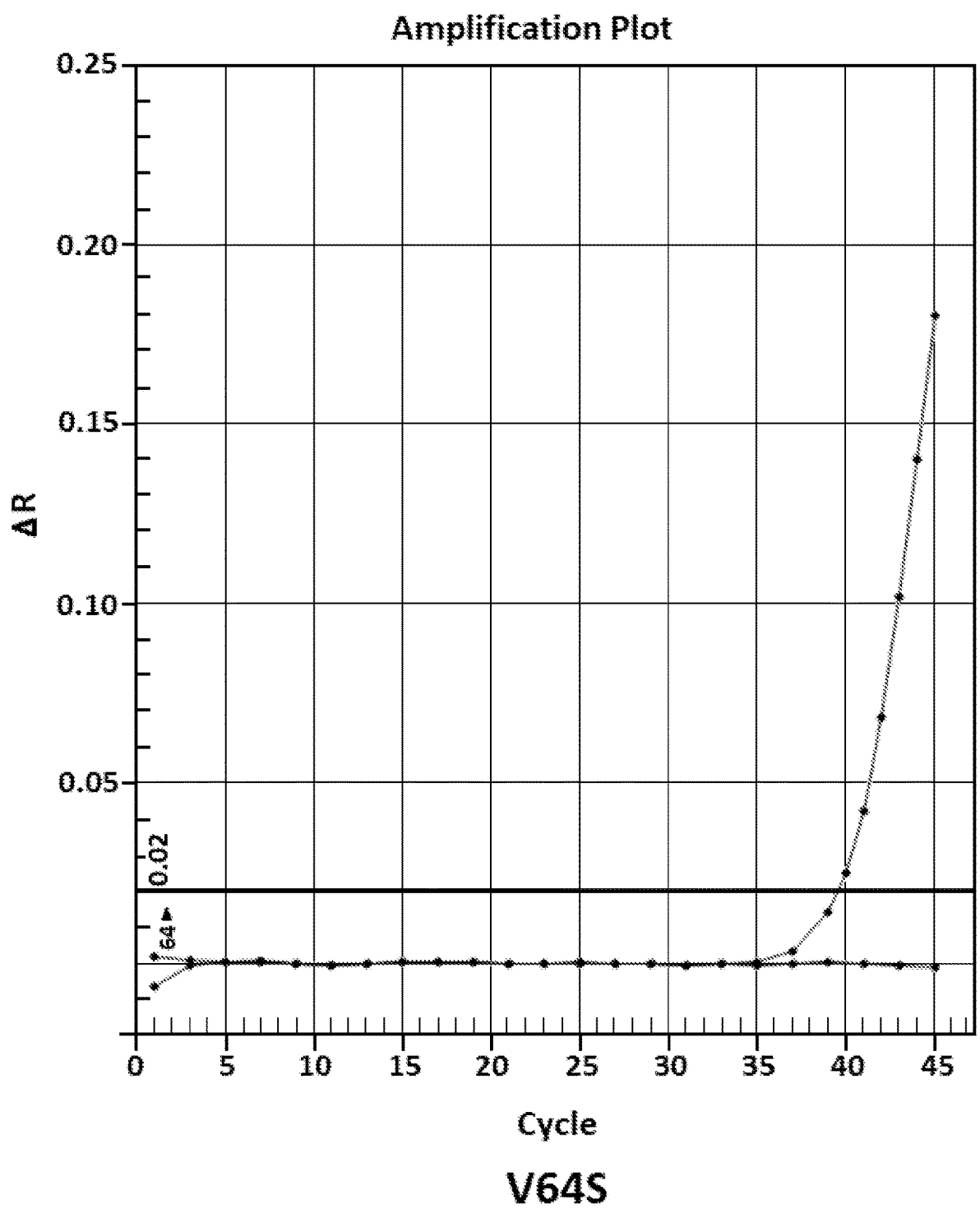
Figure 1H:
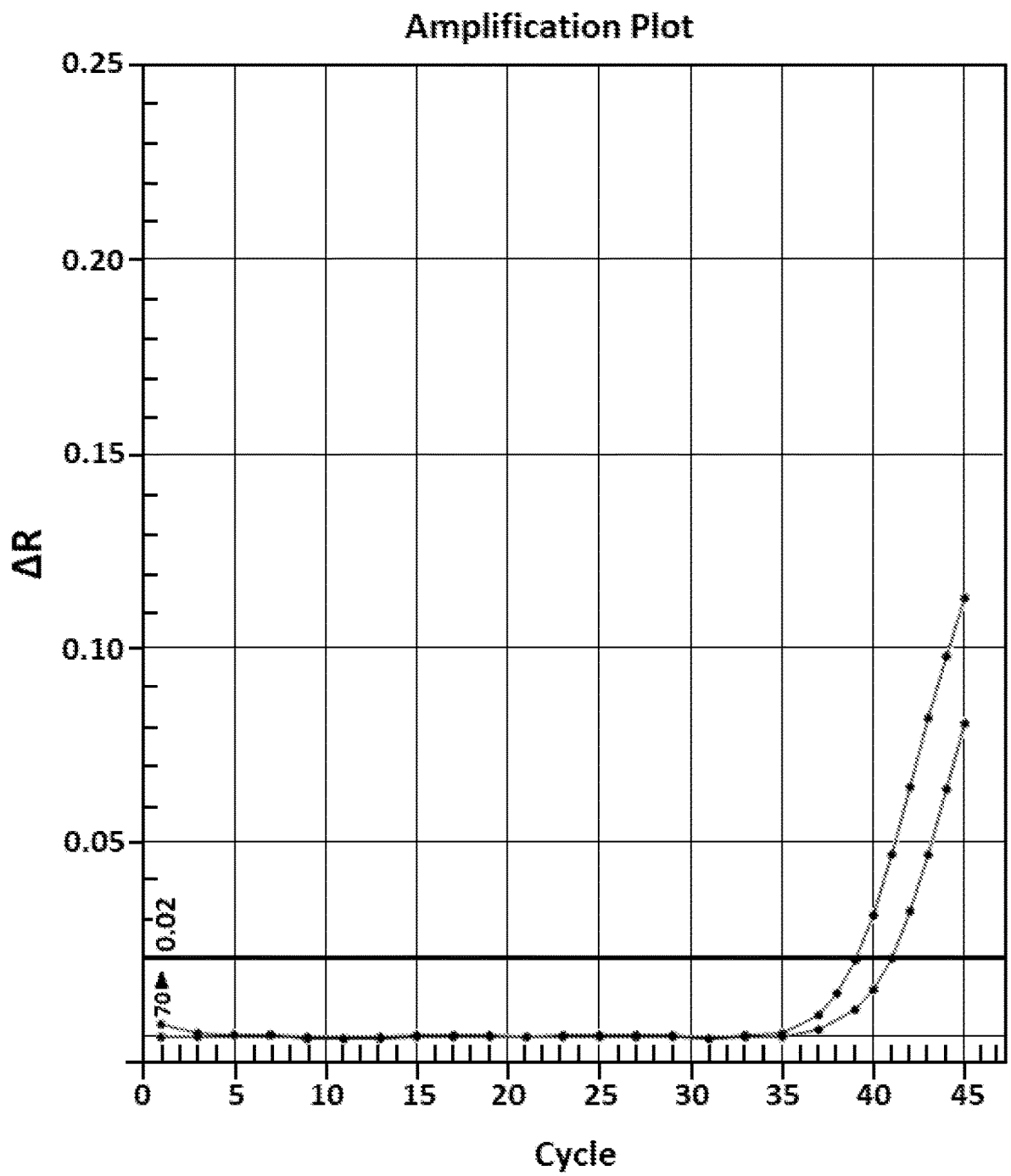
Figure 1I:
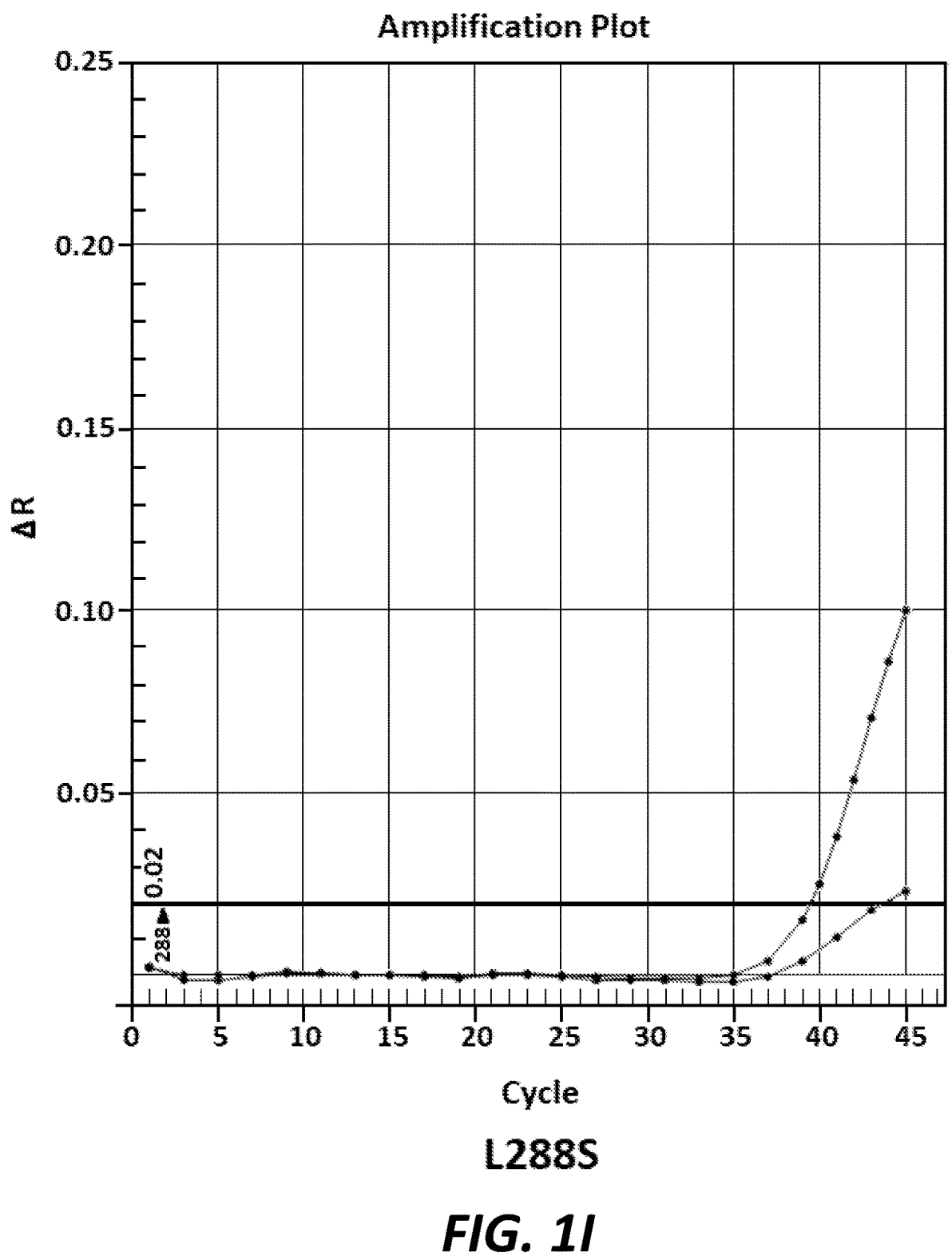
Figure 1J:
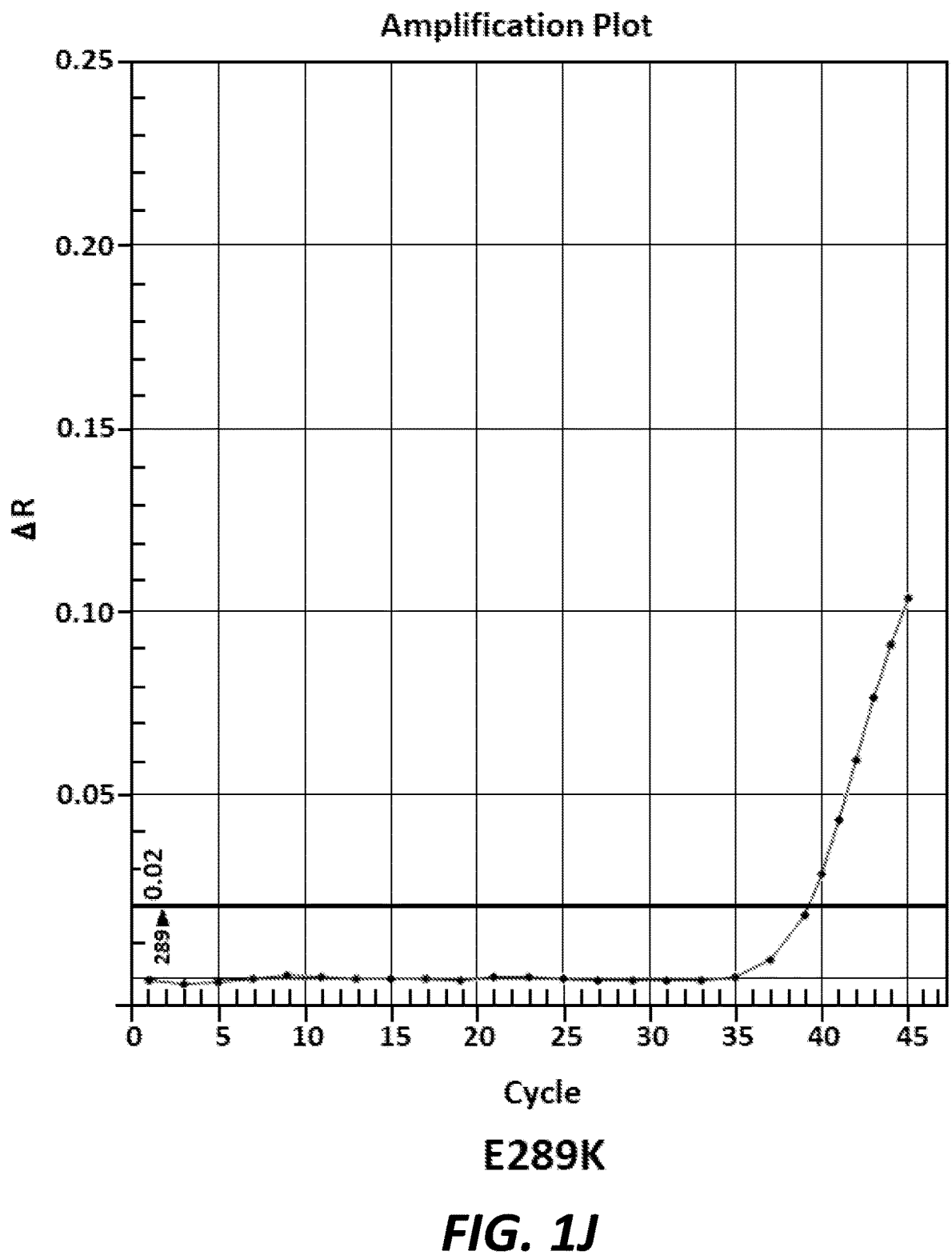
Figure 1K:
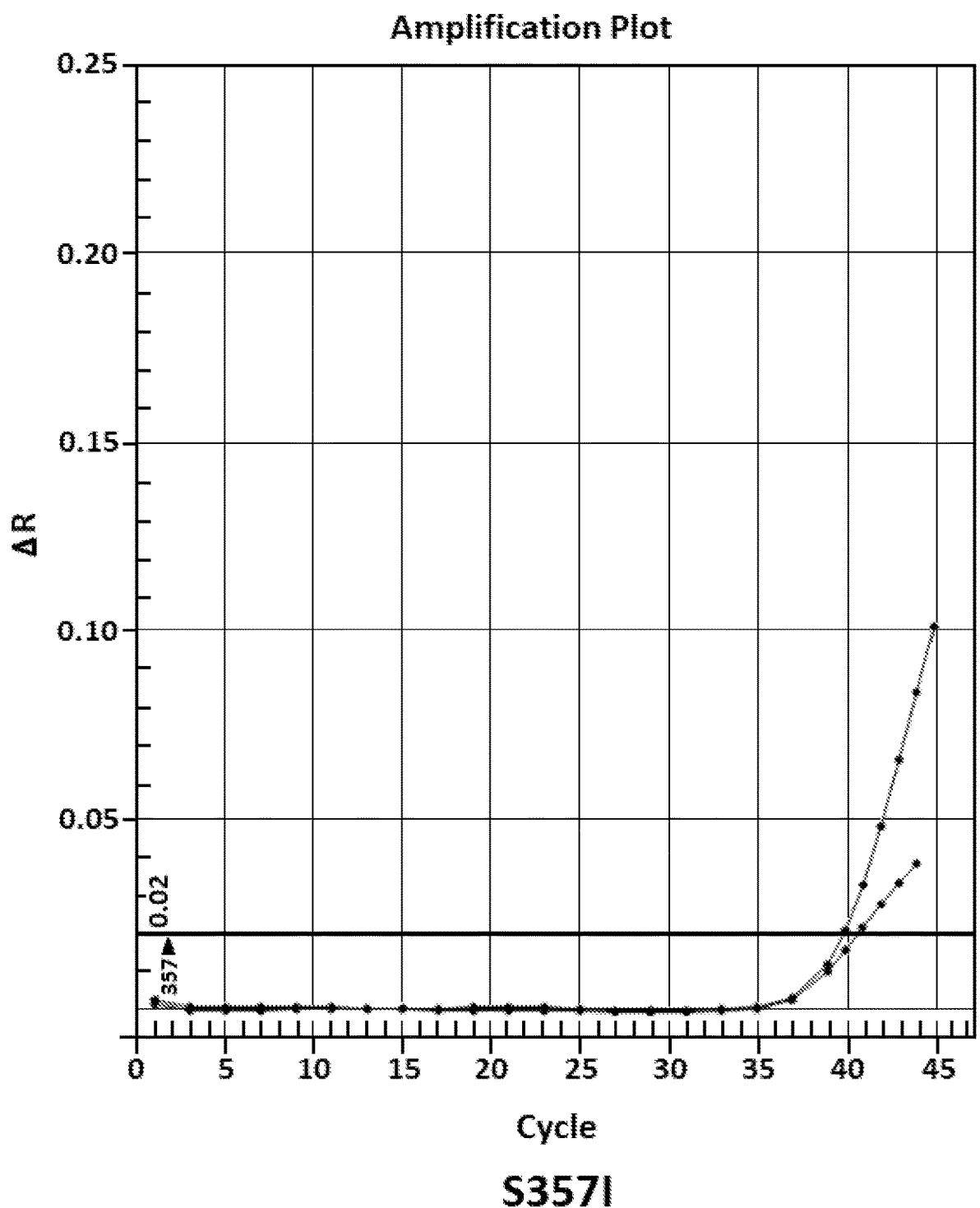
Figure 1L:
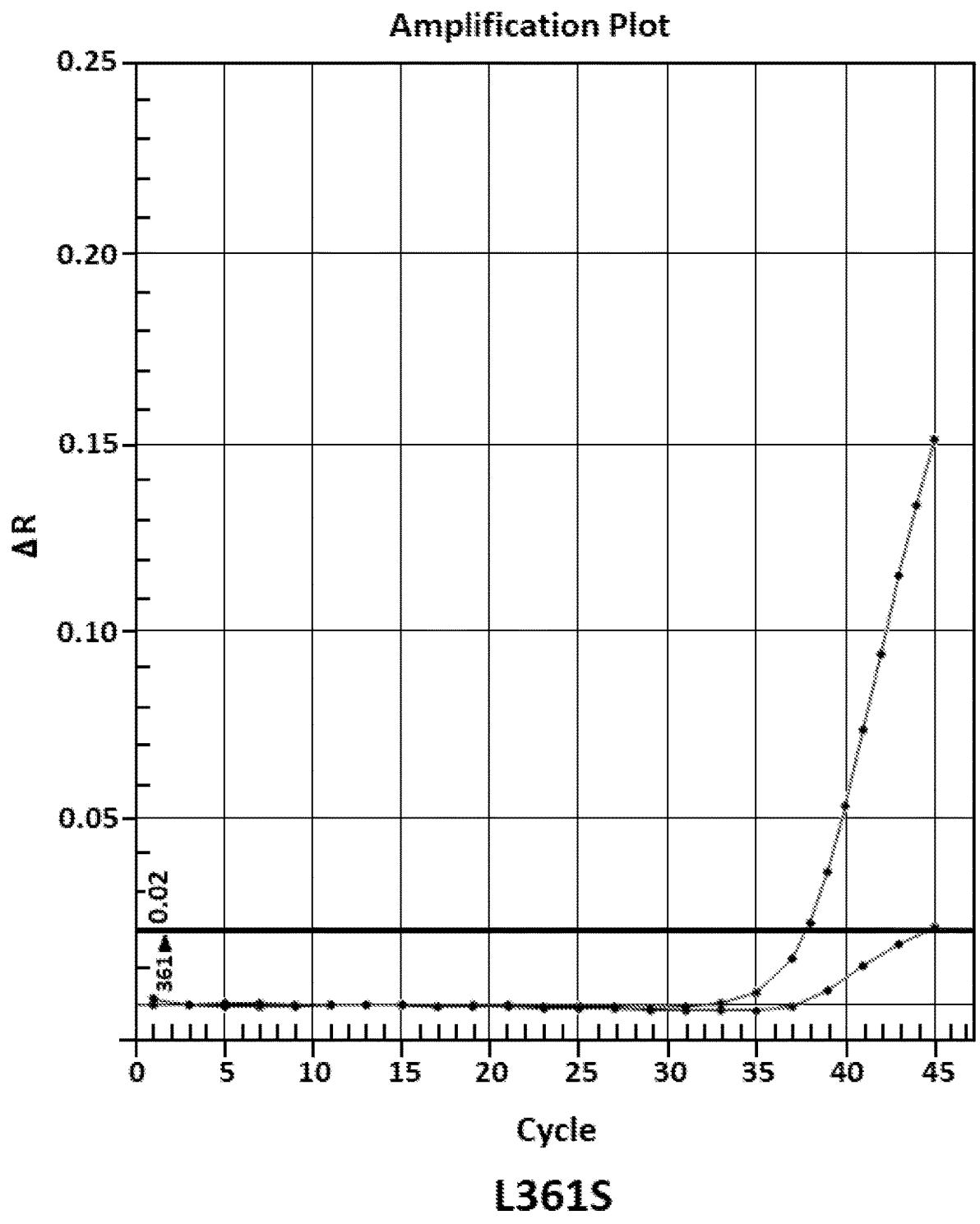
Figure 1M:
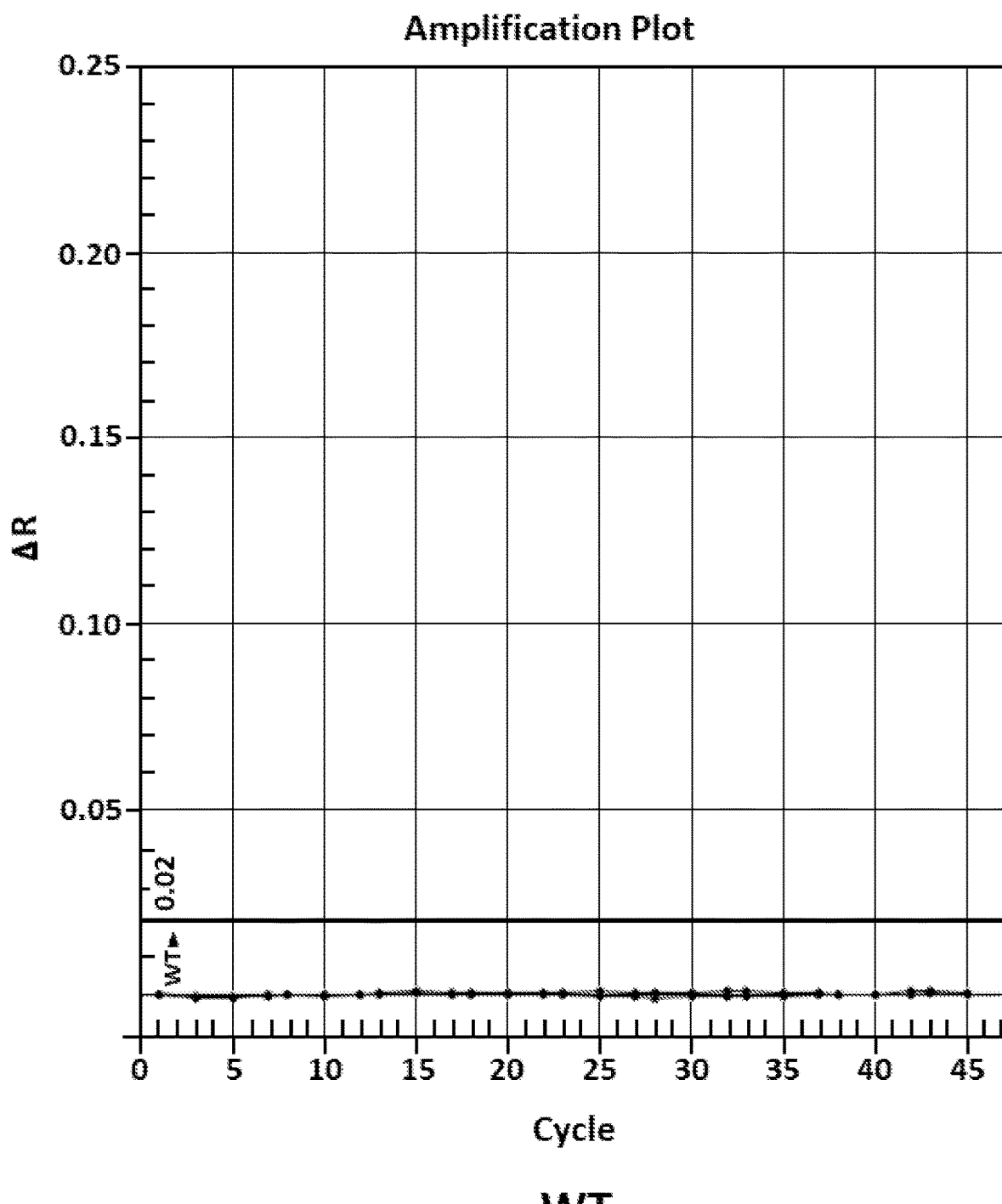
Figure 1N:
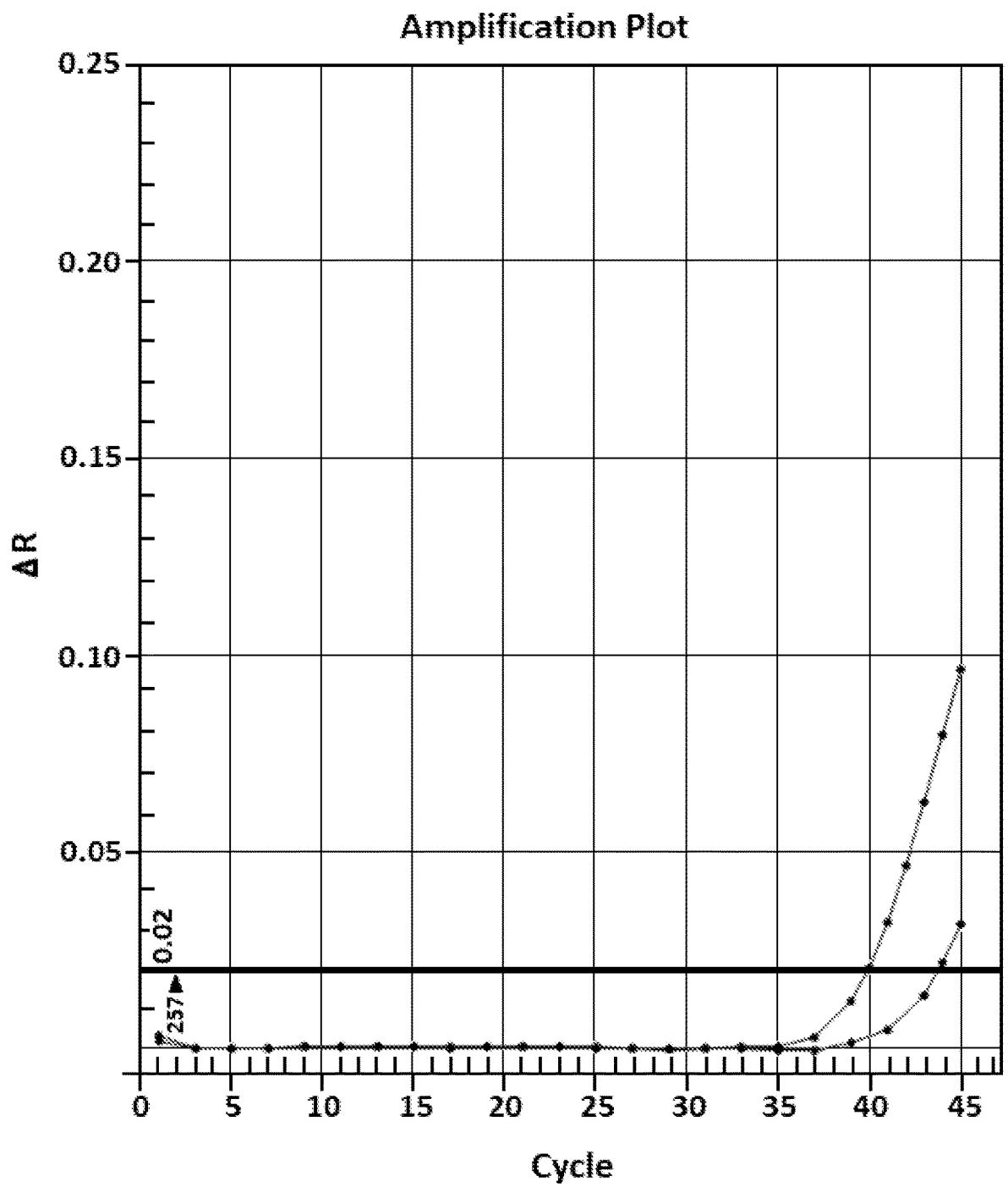
Figure 1O:
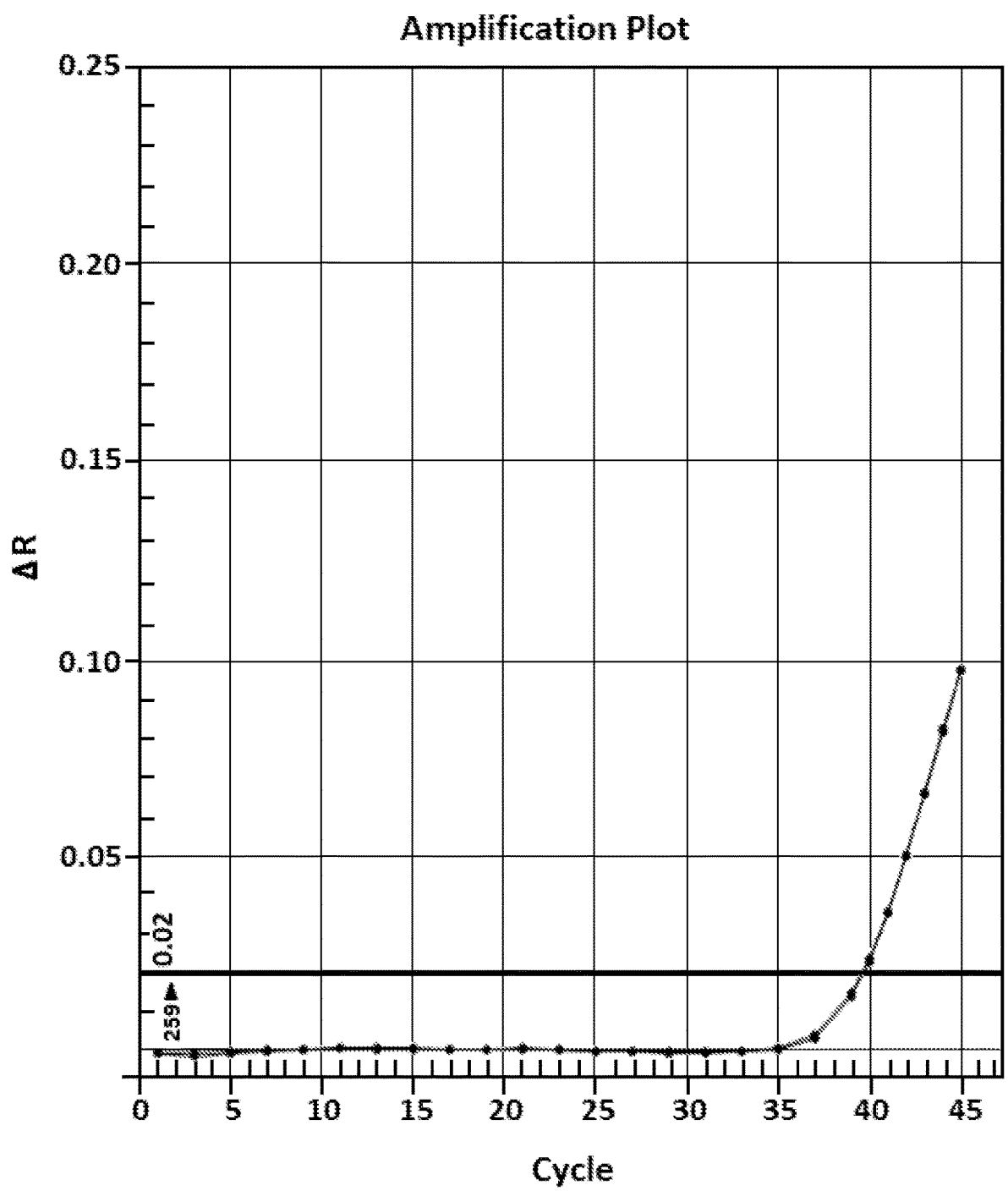
Figure 1P:
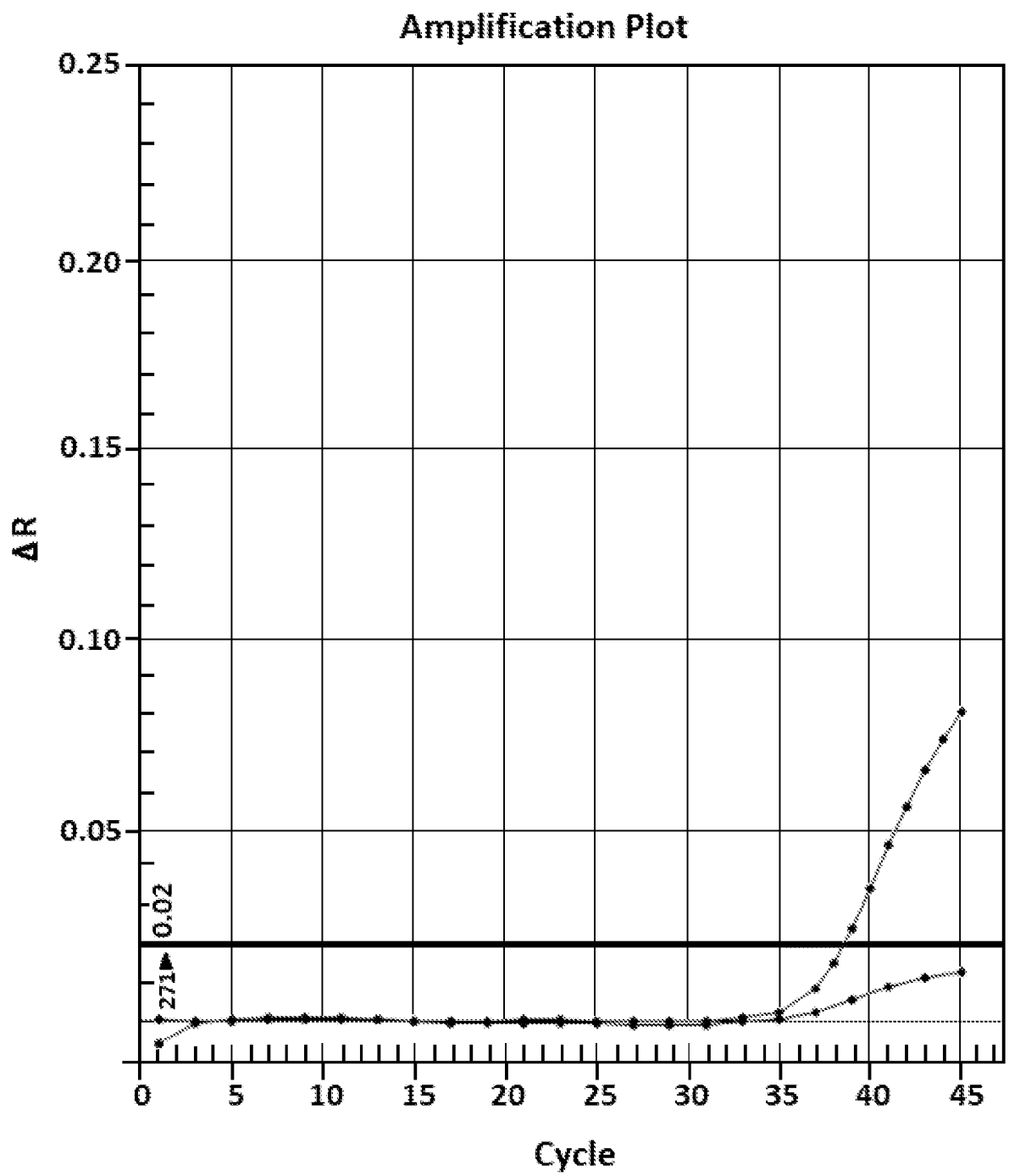
Figure 1Q:
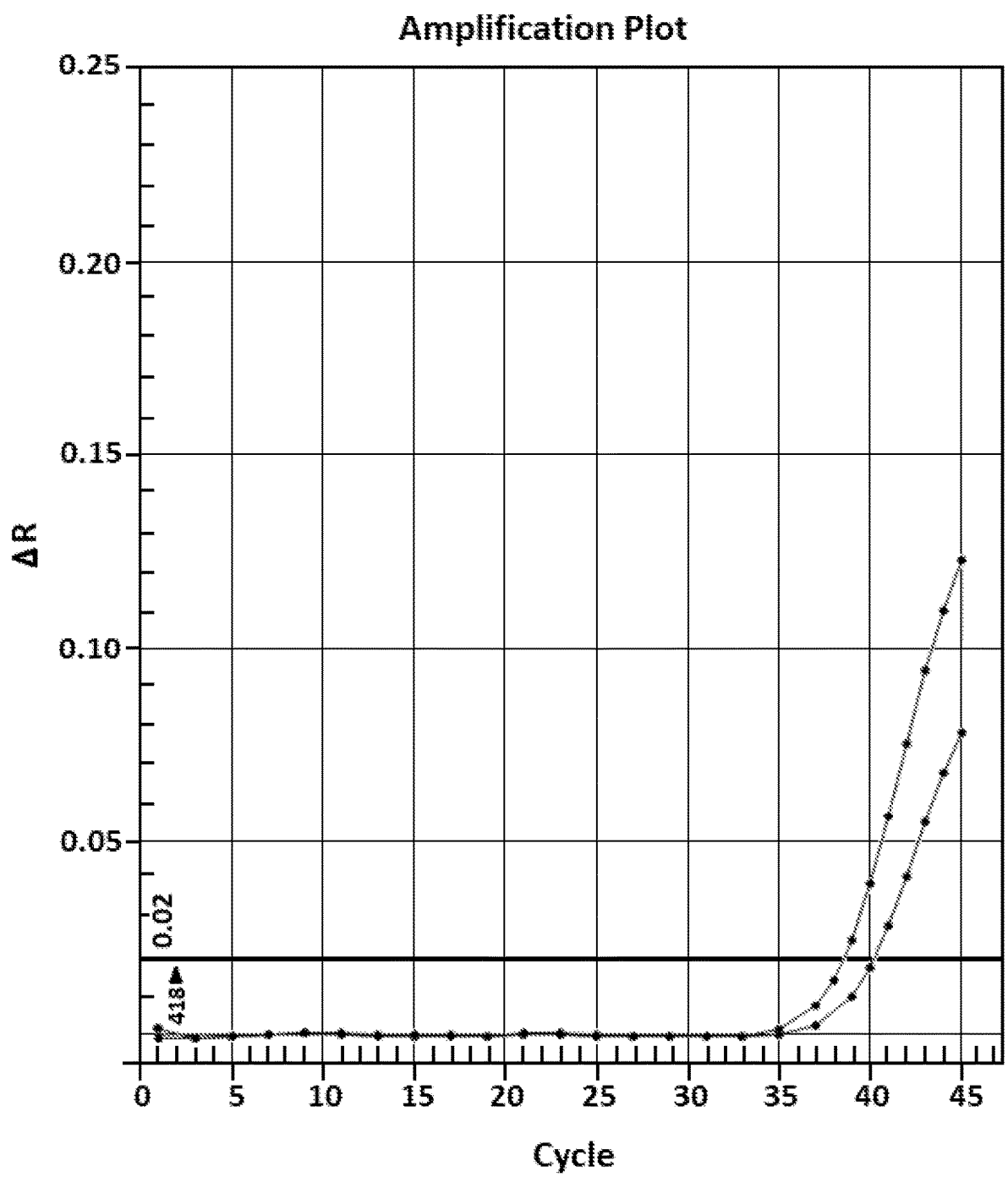
Figure 1R:
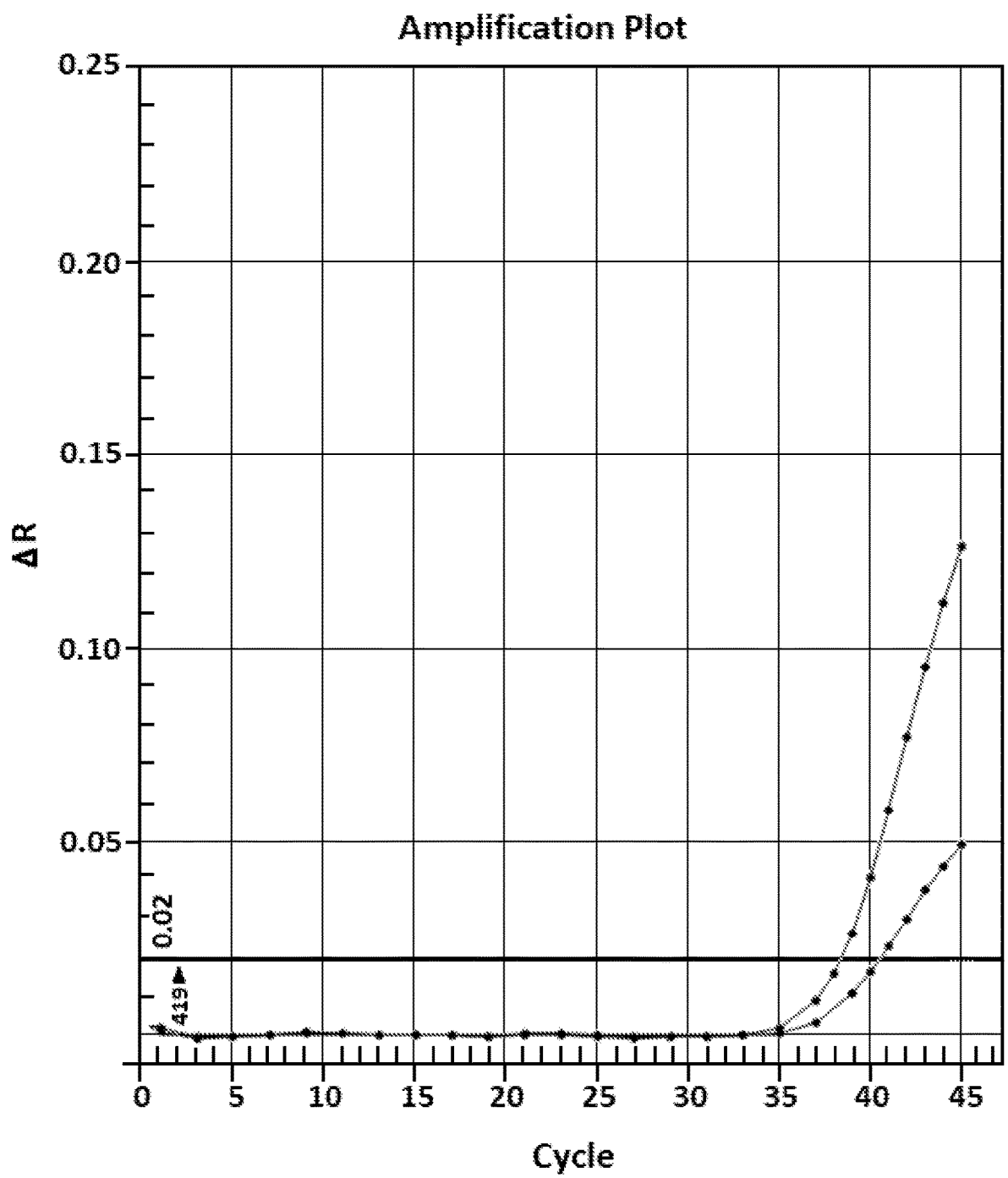
Figure 1S:
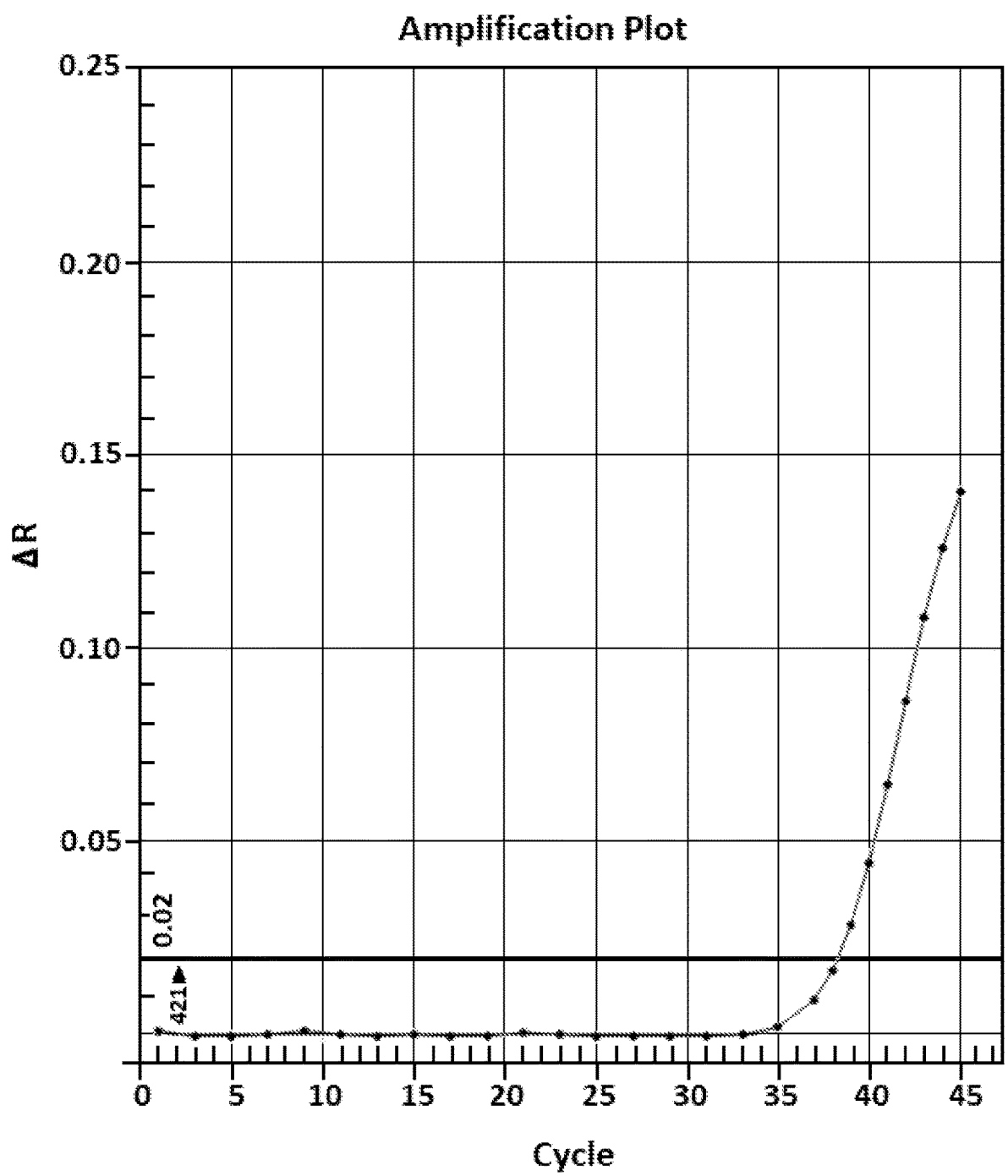
Figure 1T:
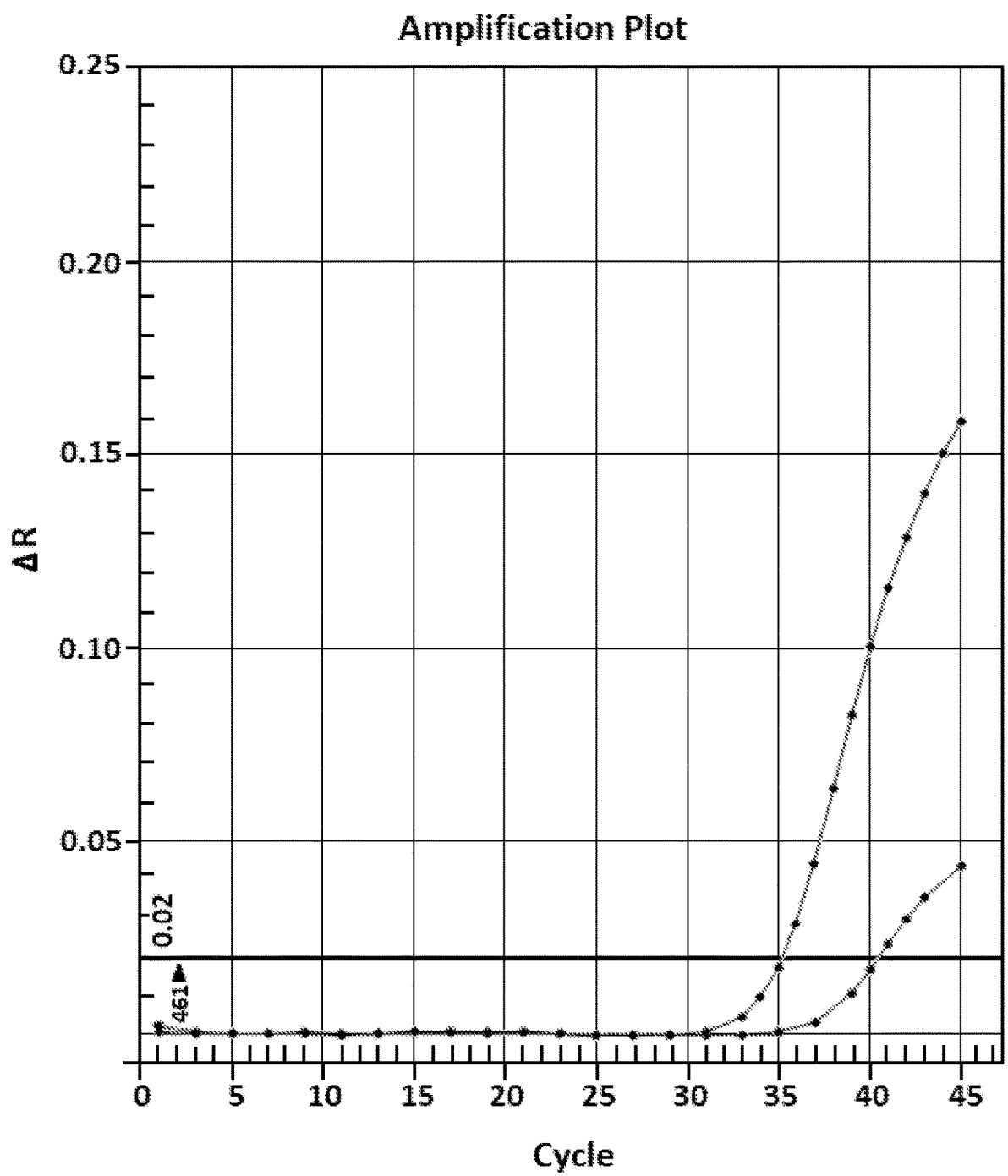
Figure 1U:
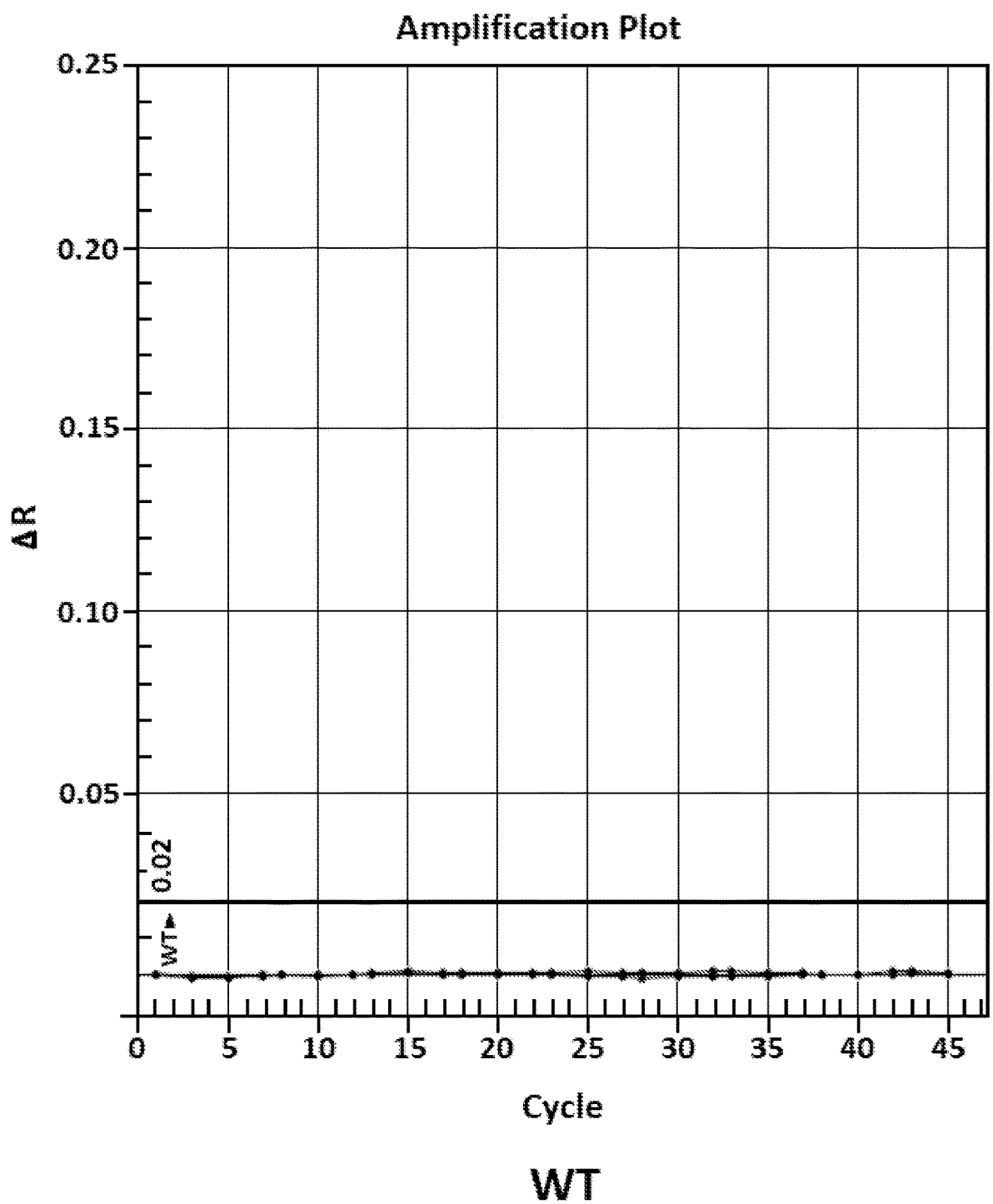
Figure 1V:
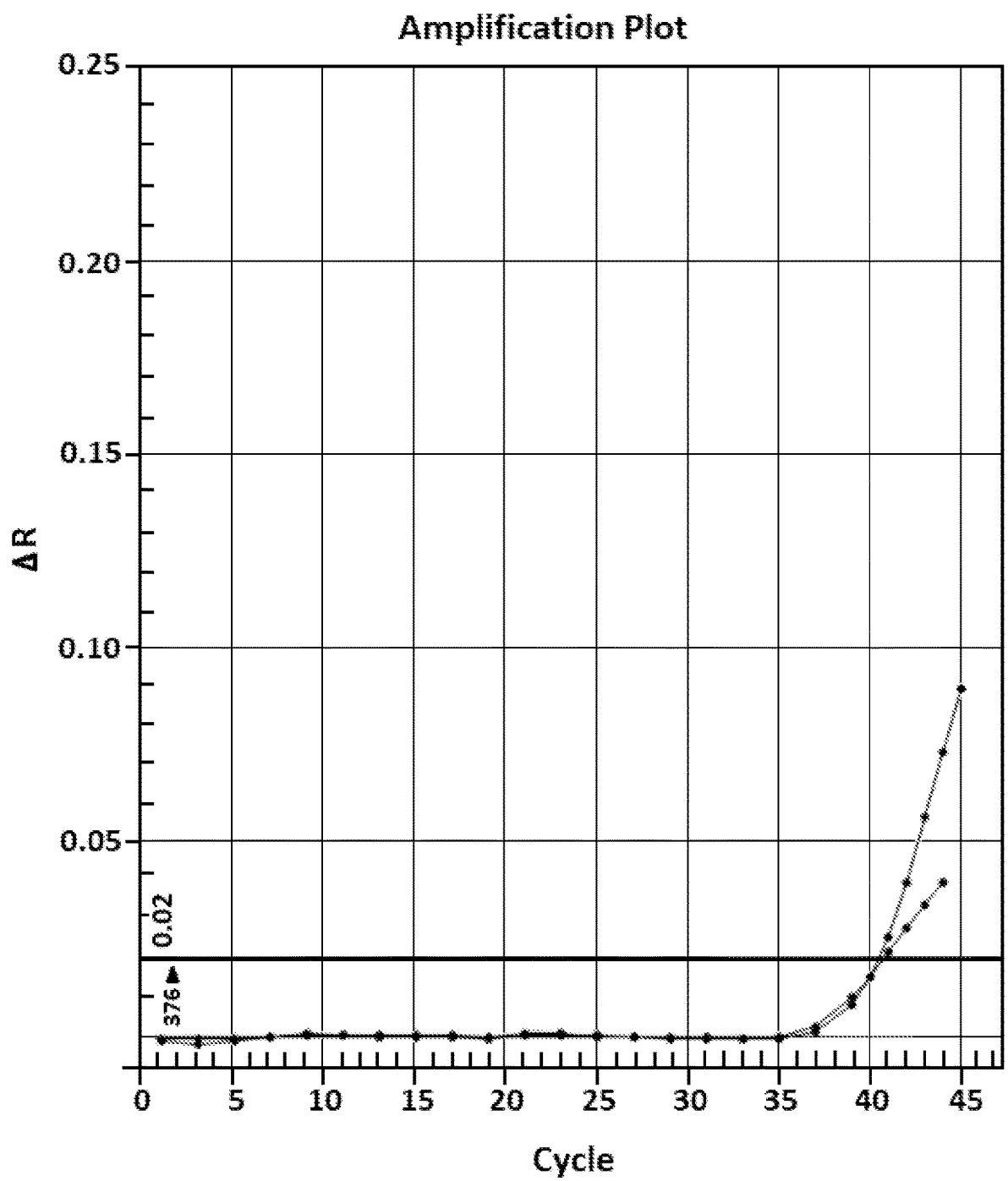
Figure 1W:
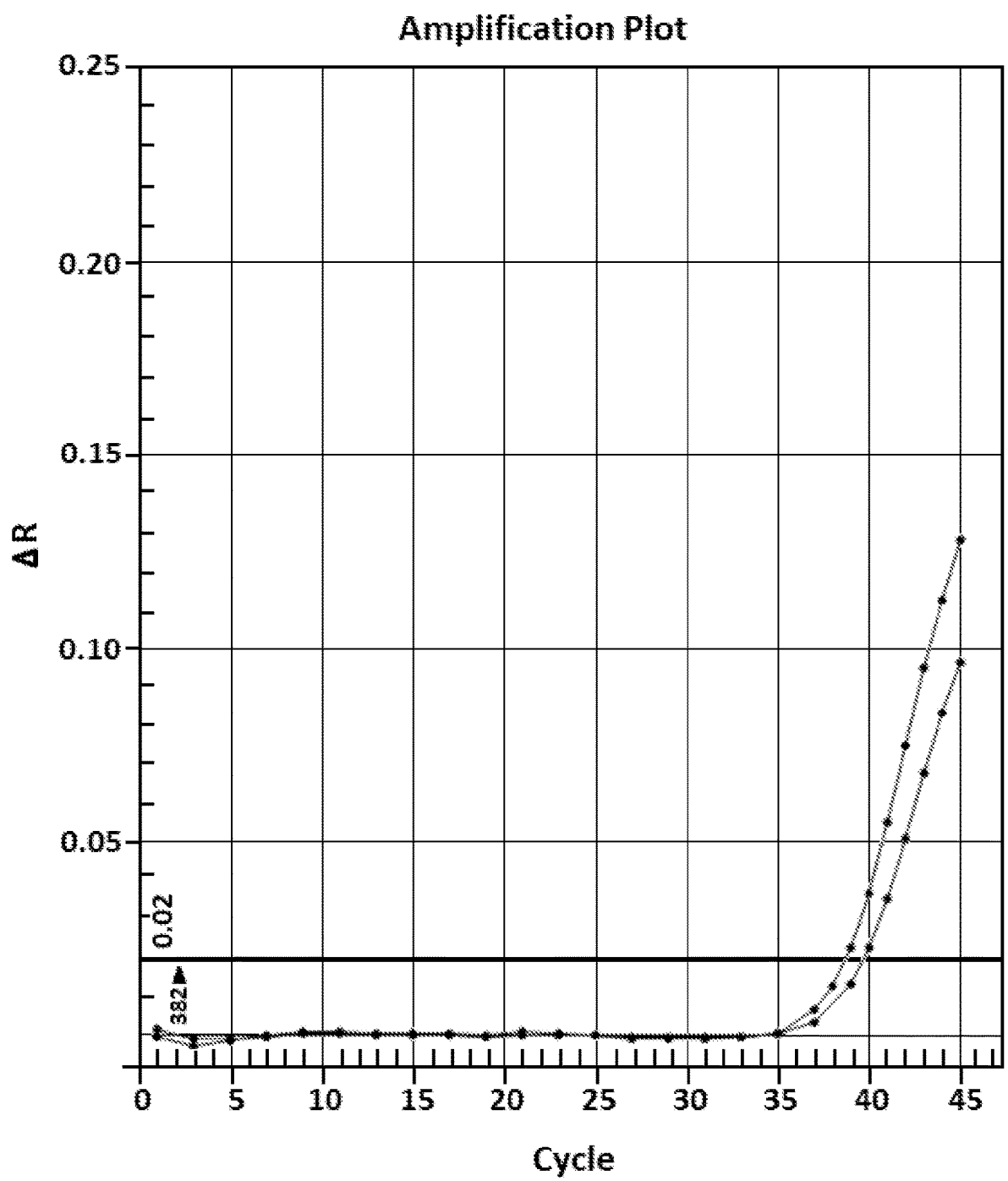
Figure 1X:
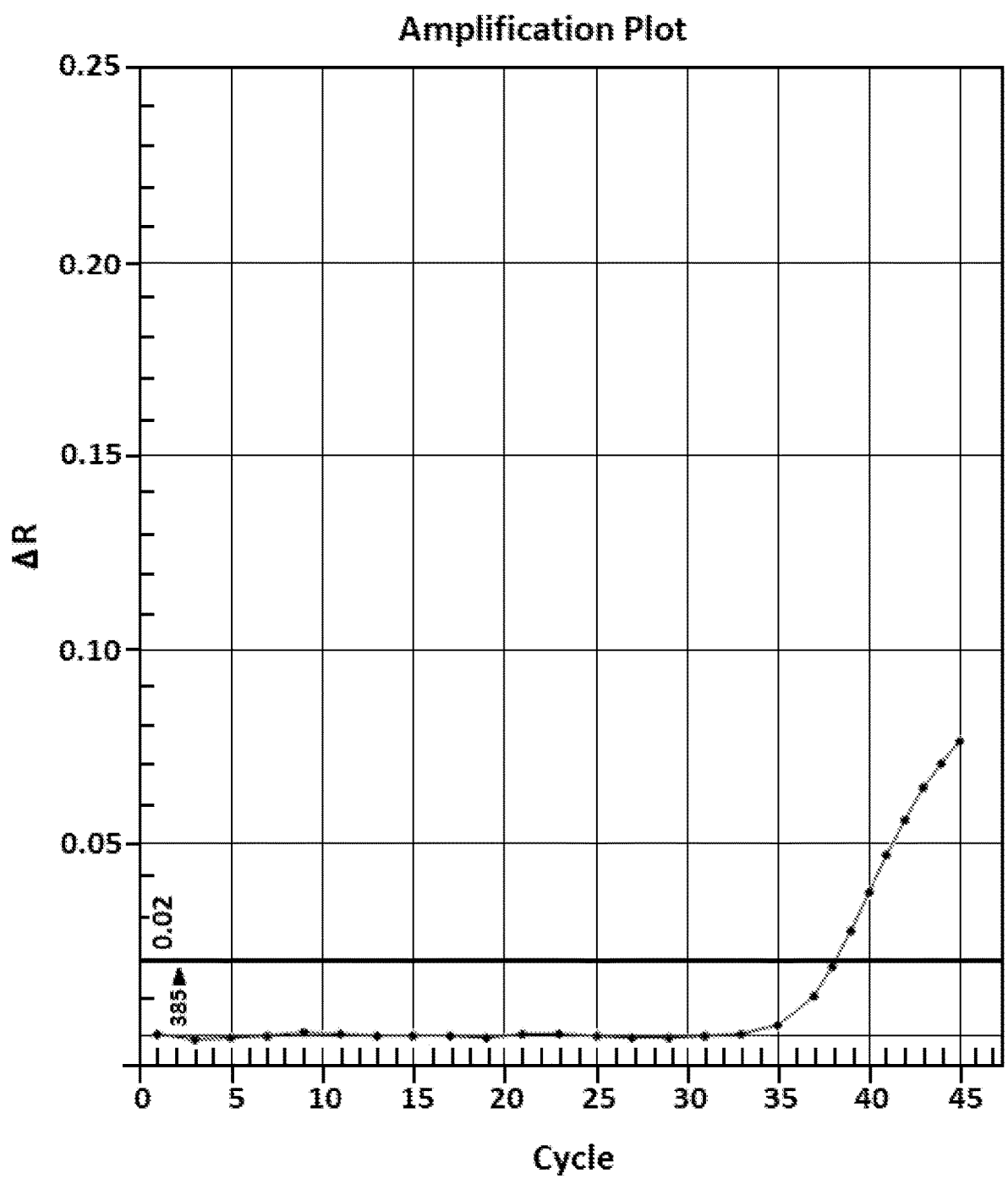
Figure 1Y:
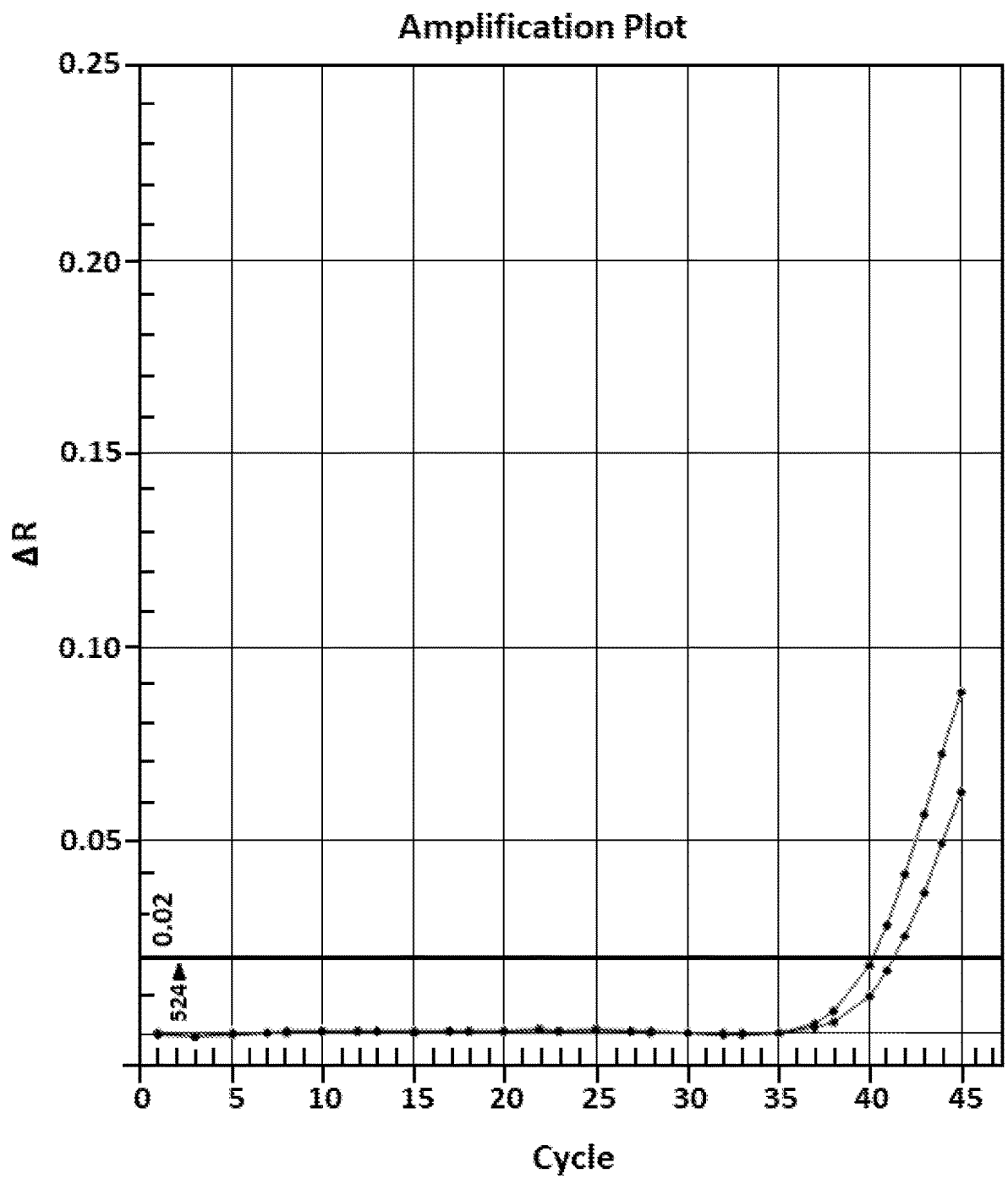
Figure 1Z:
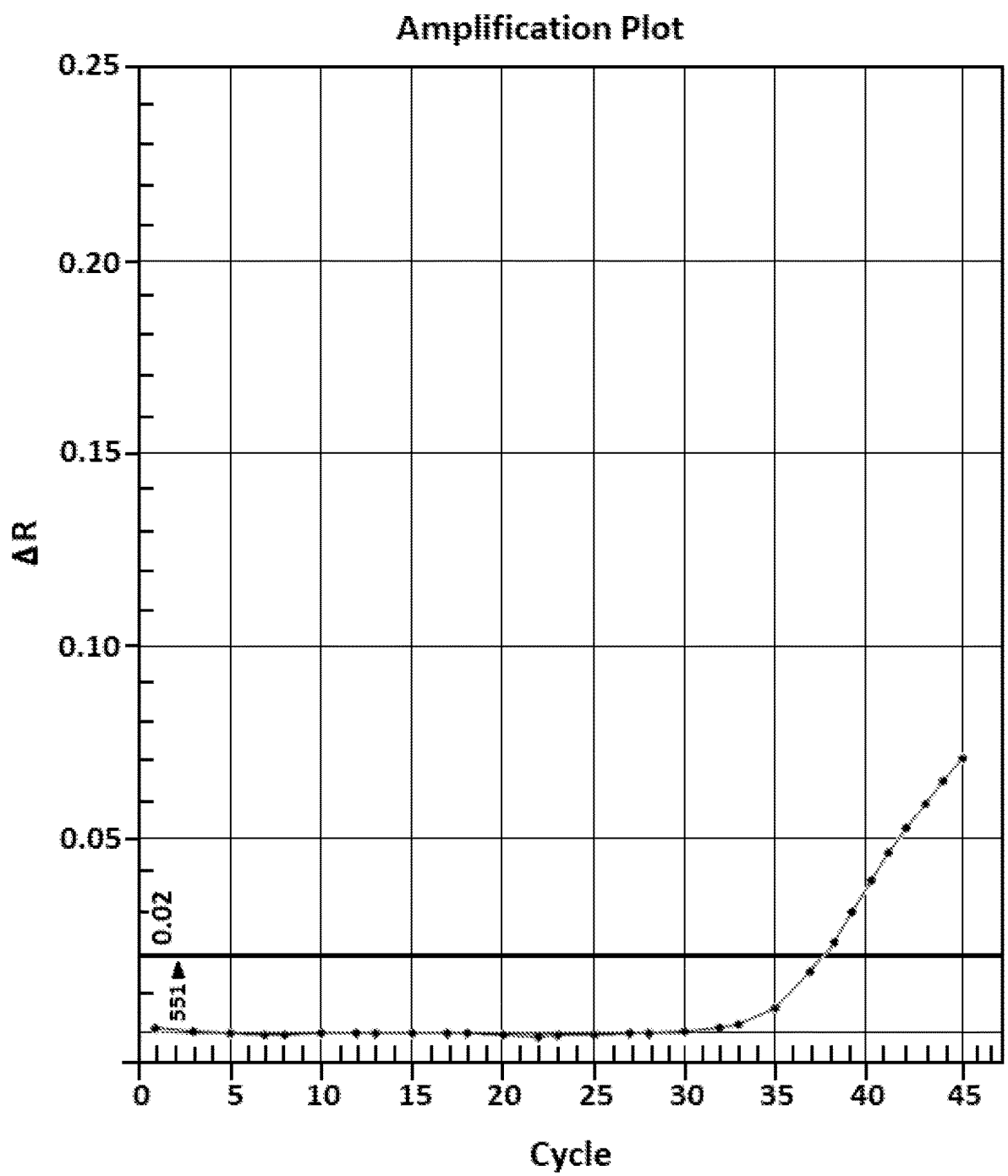
Figure 1A:
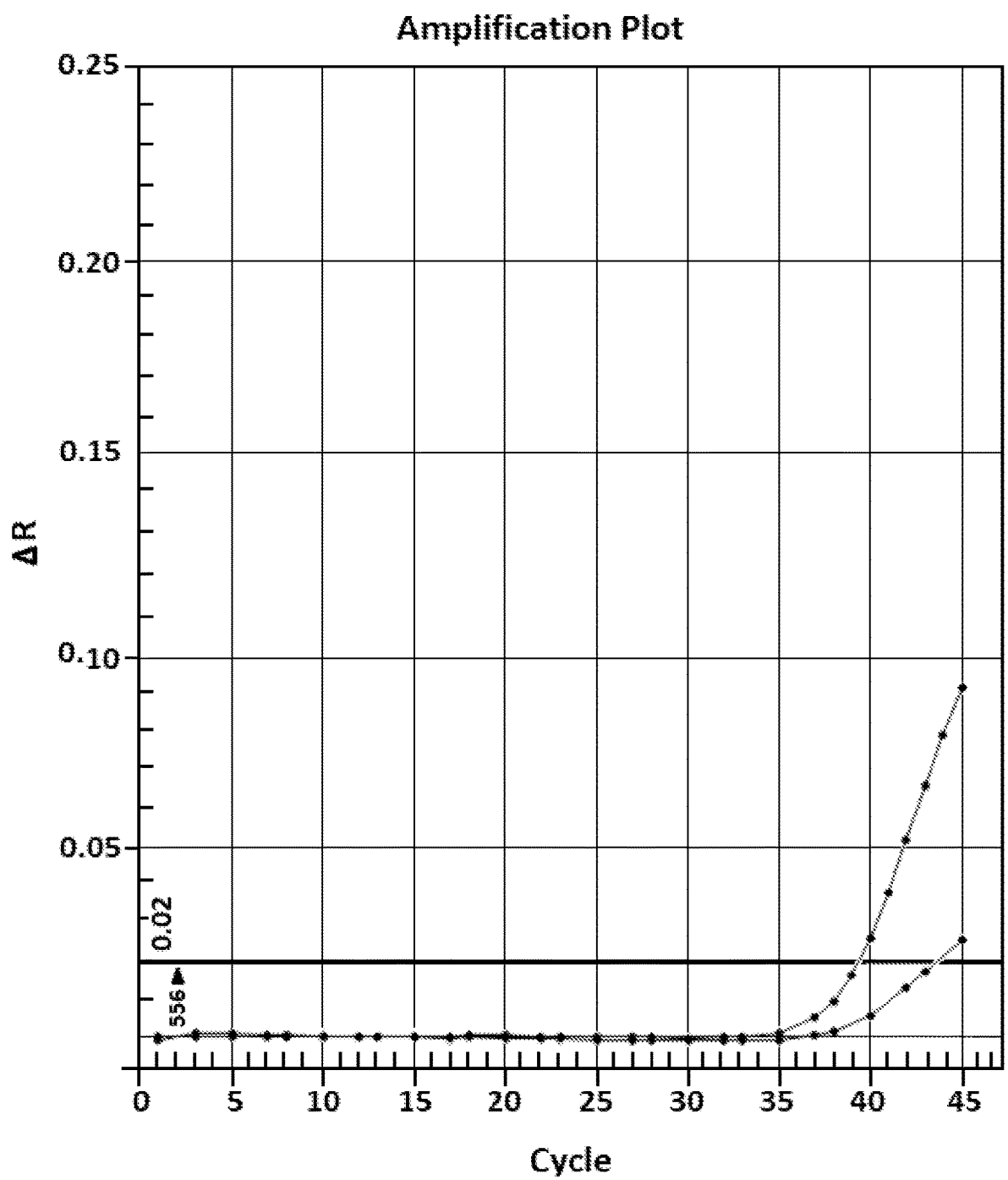
Figure 1B:
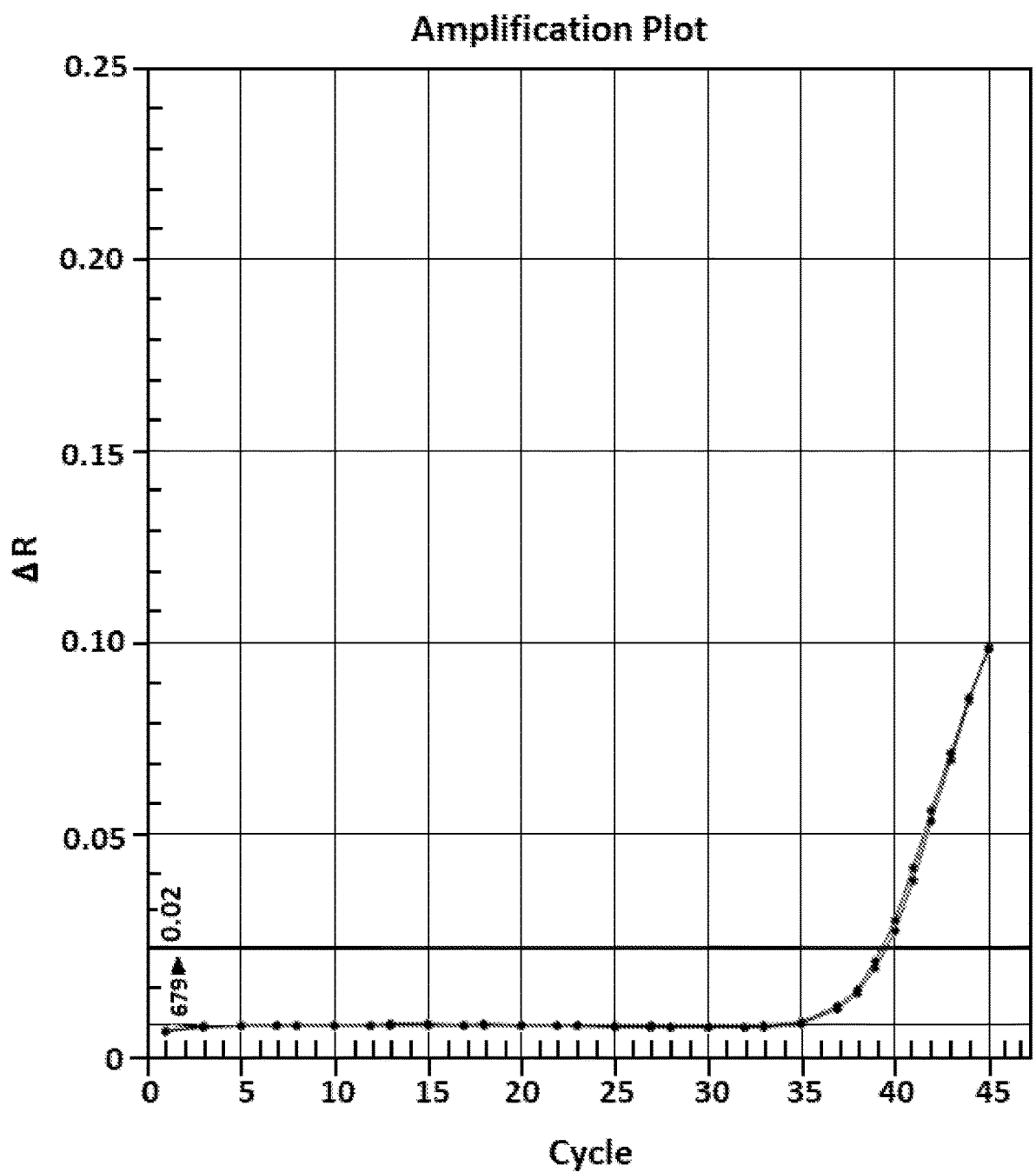
Figure 1C:
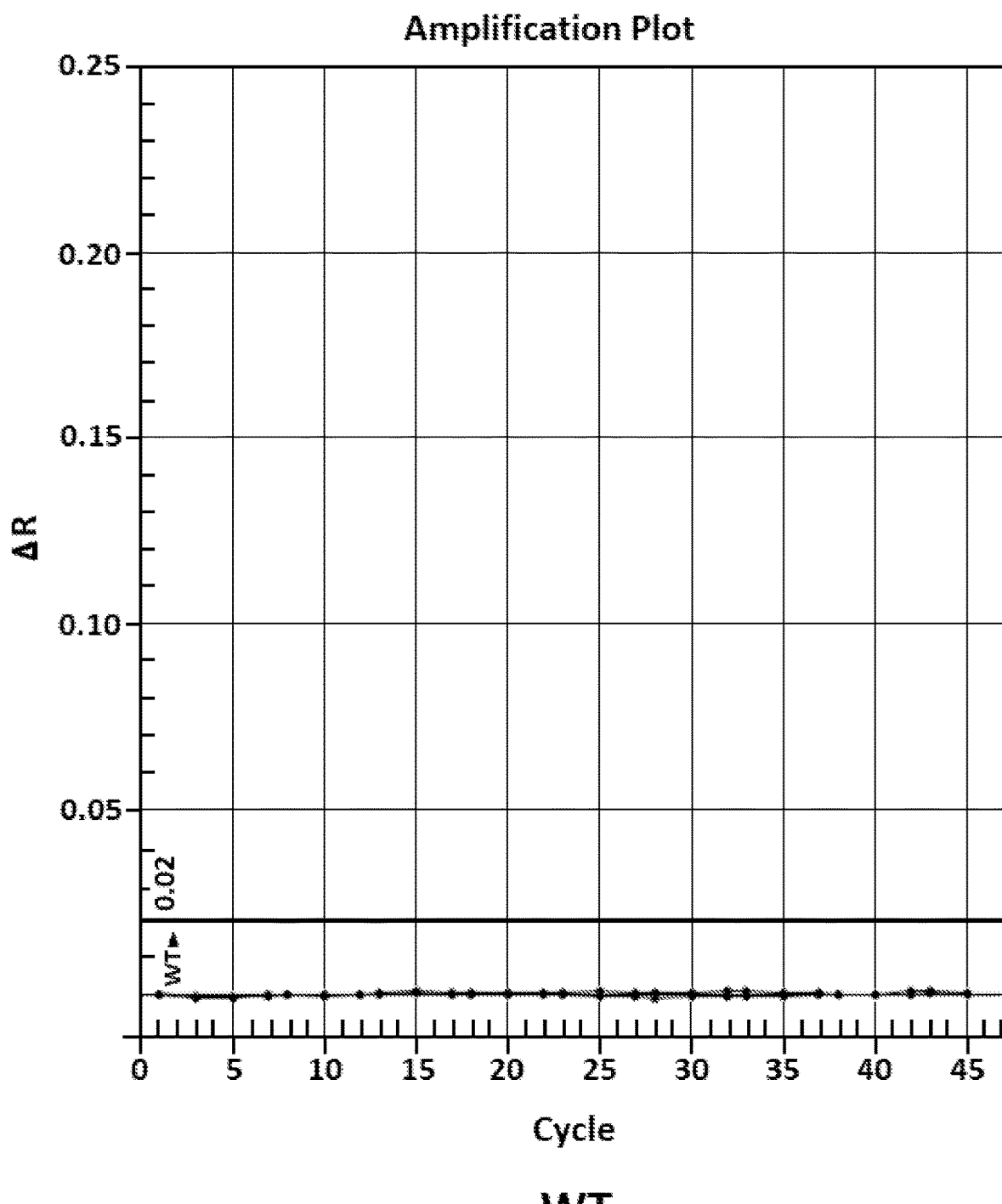
Figure 1D:
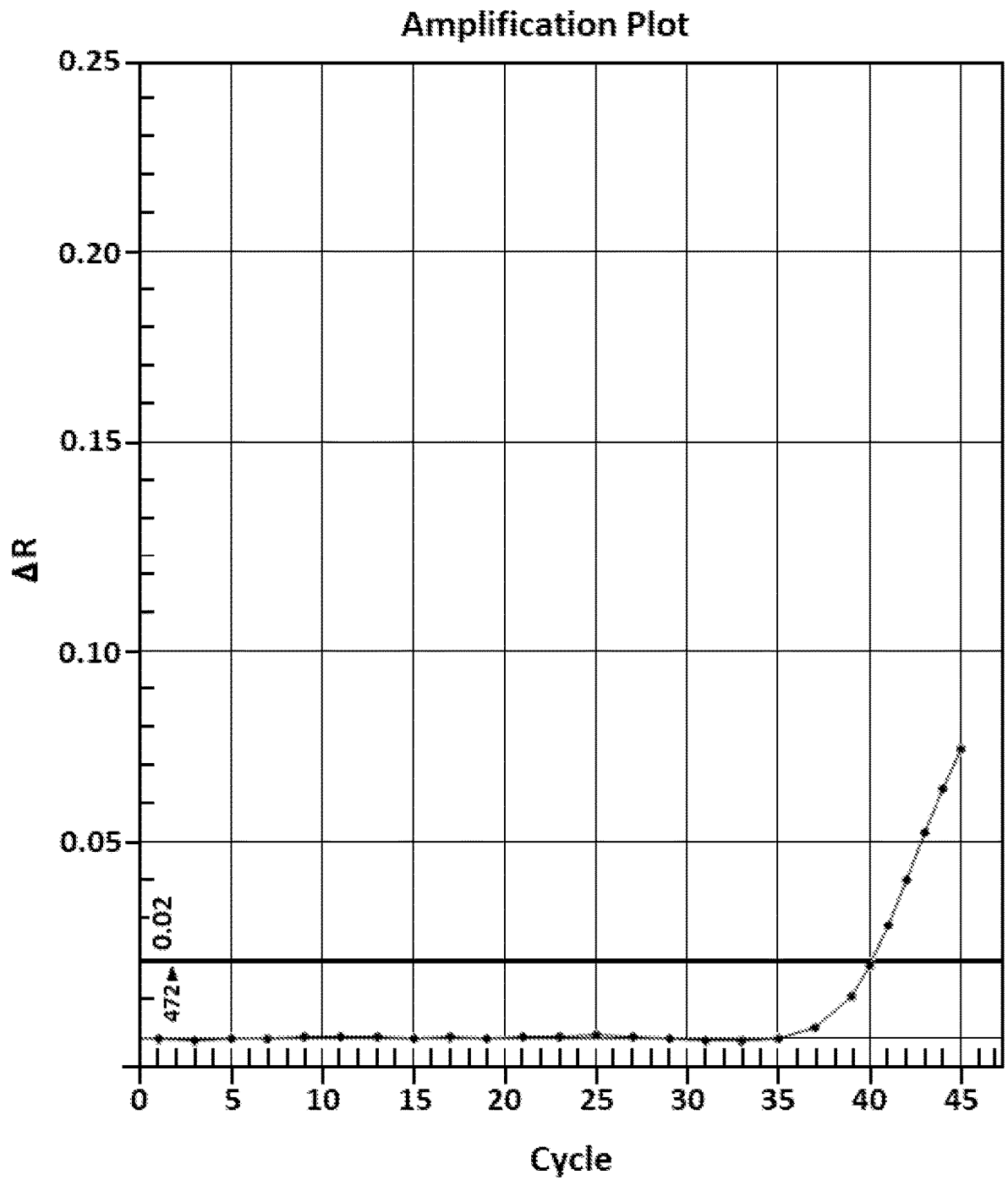
Figure 1E:
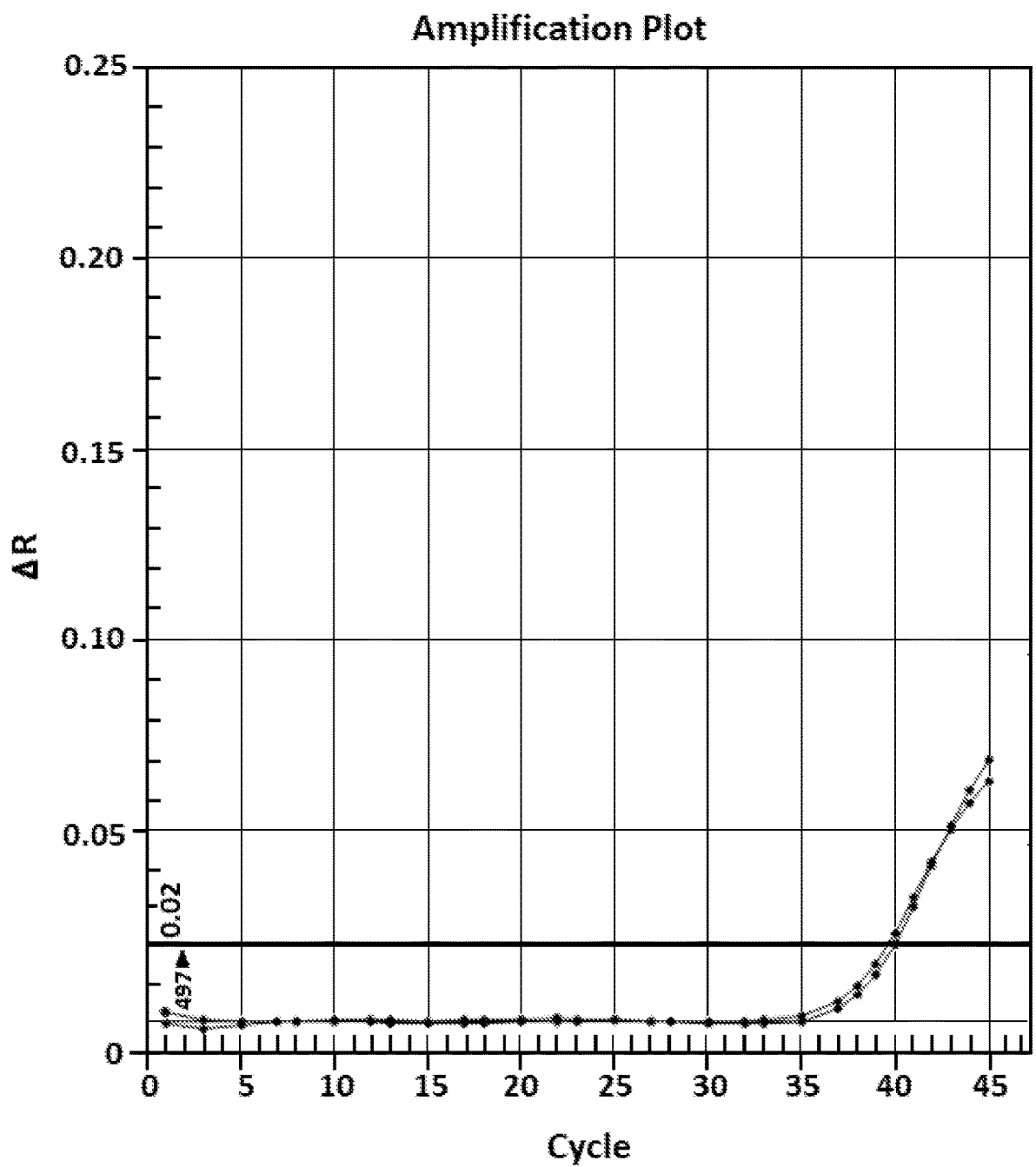
Figure 1F:
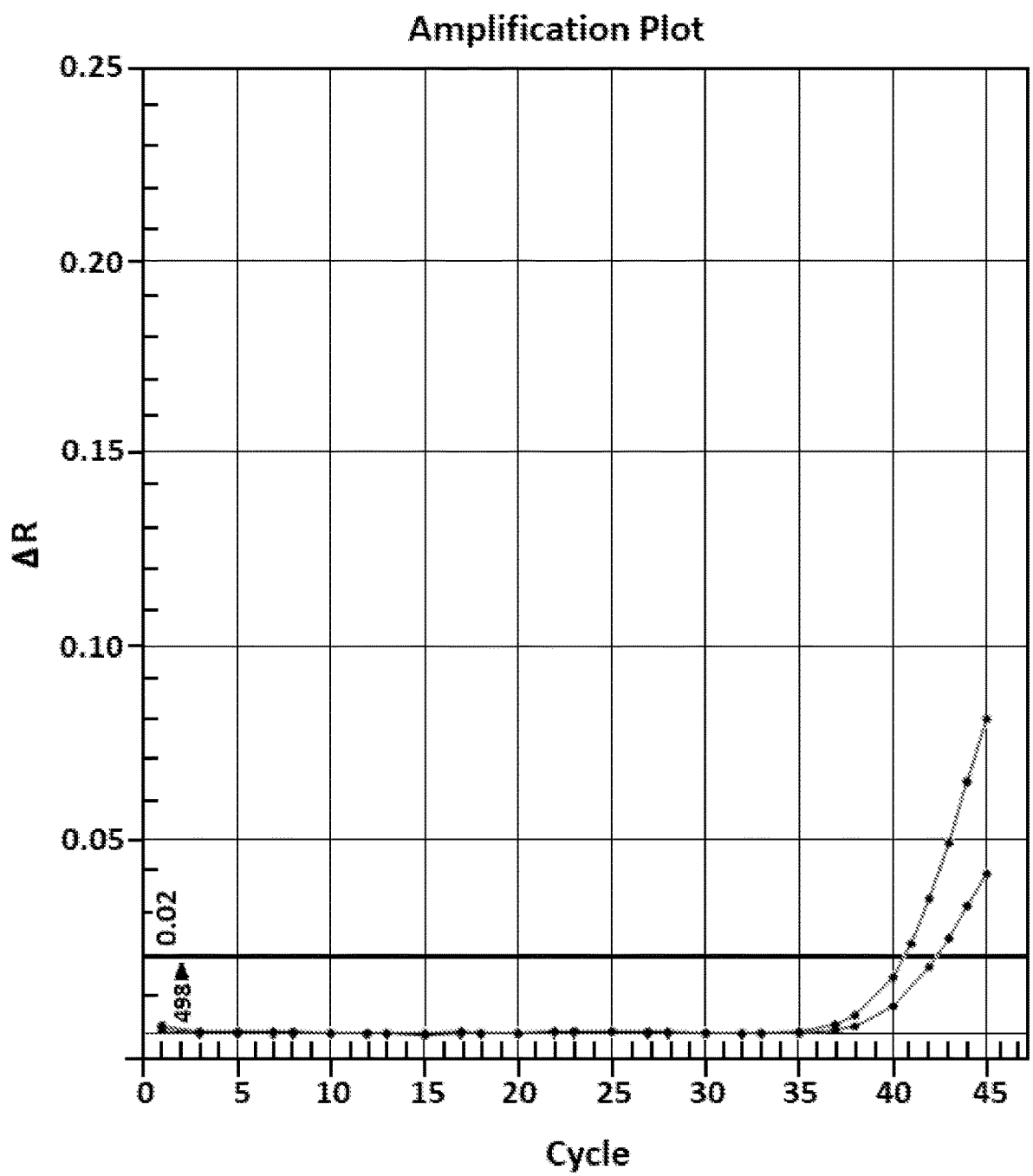
Figure 1G:
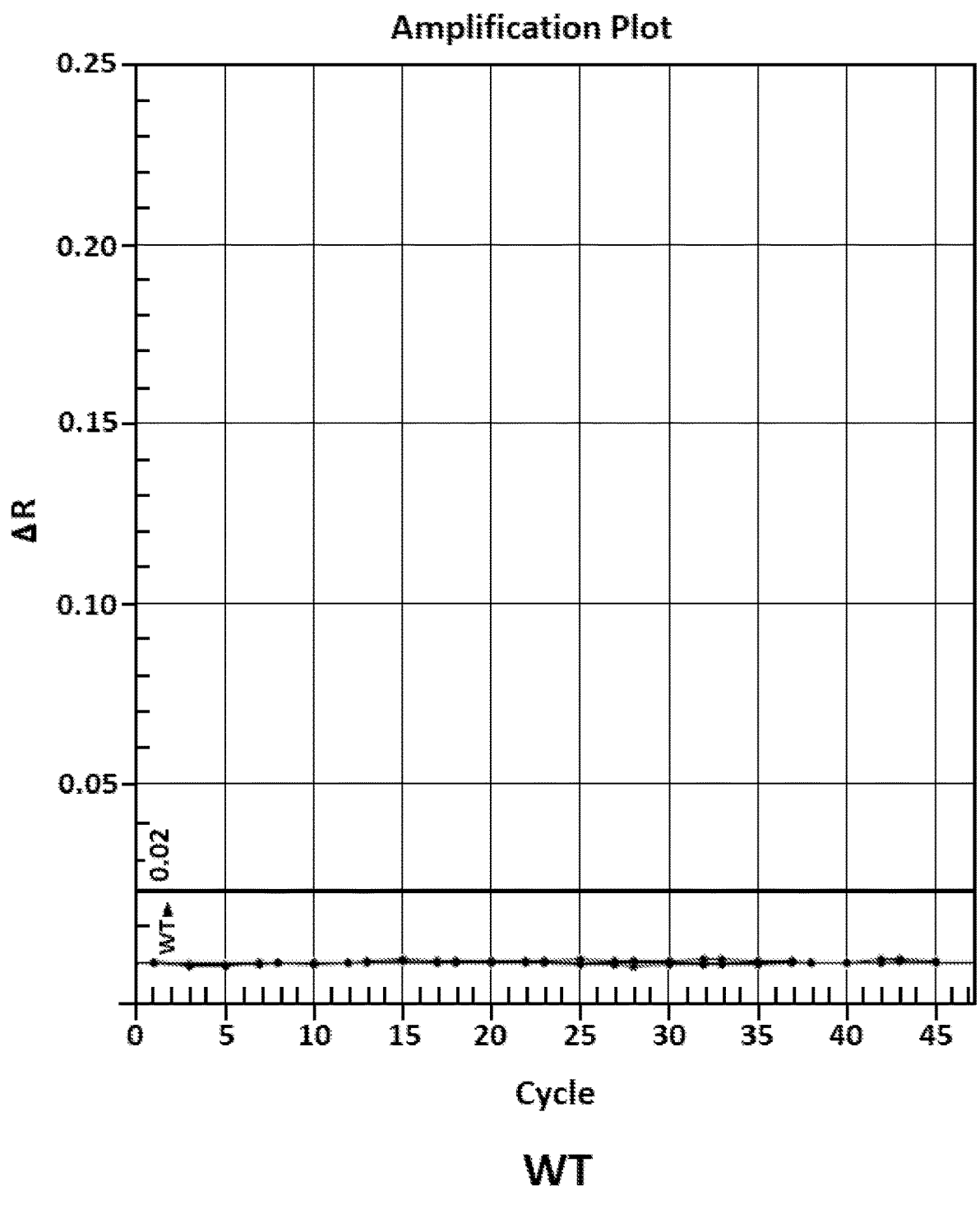
Figure 1H:
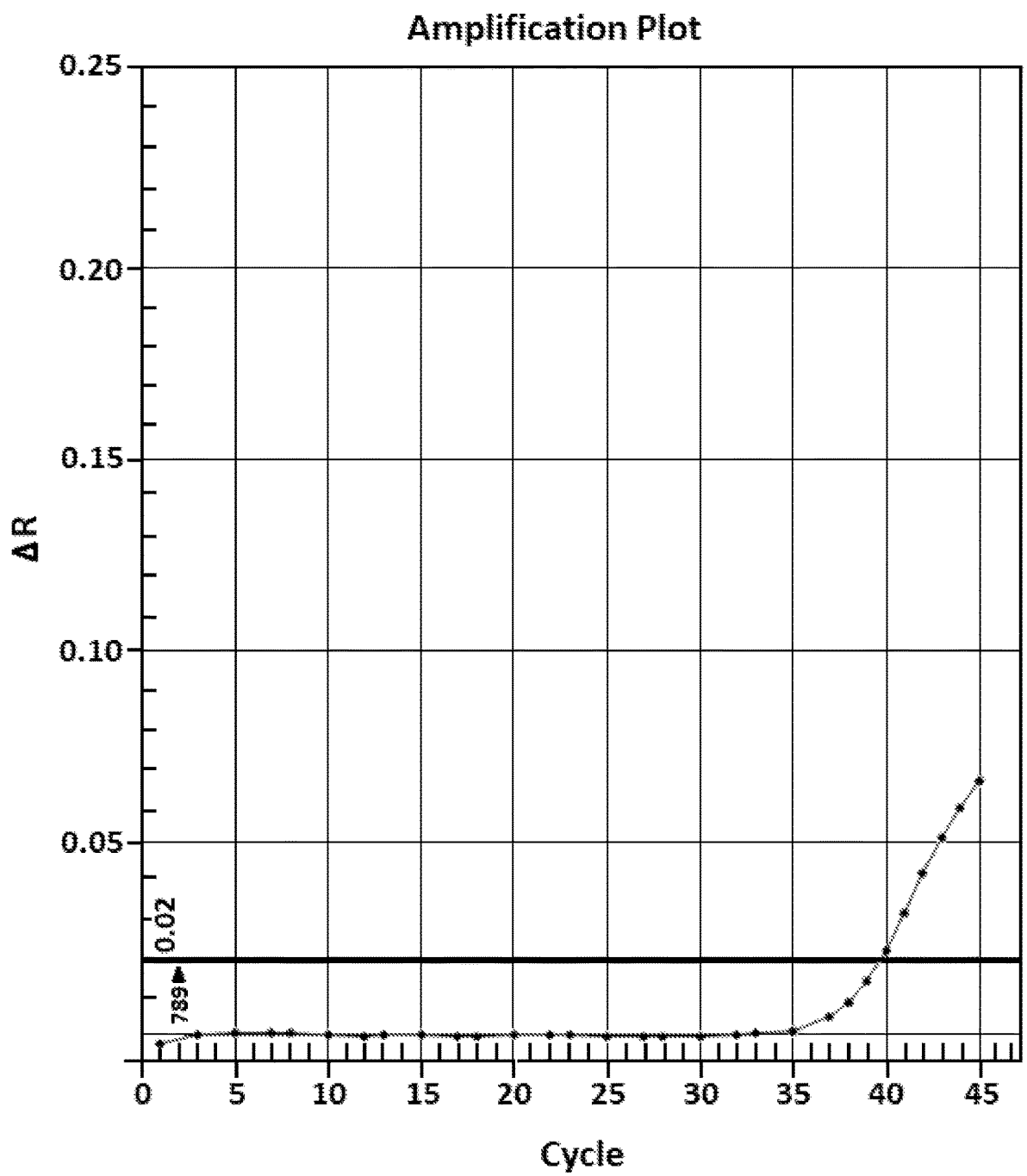
Figure 1L:
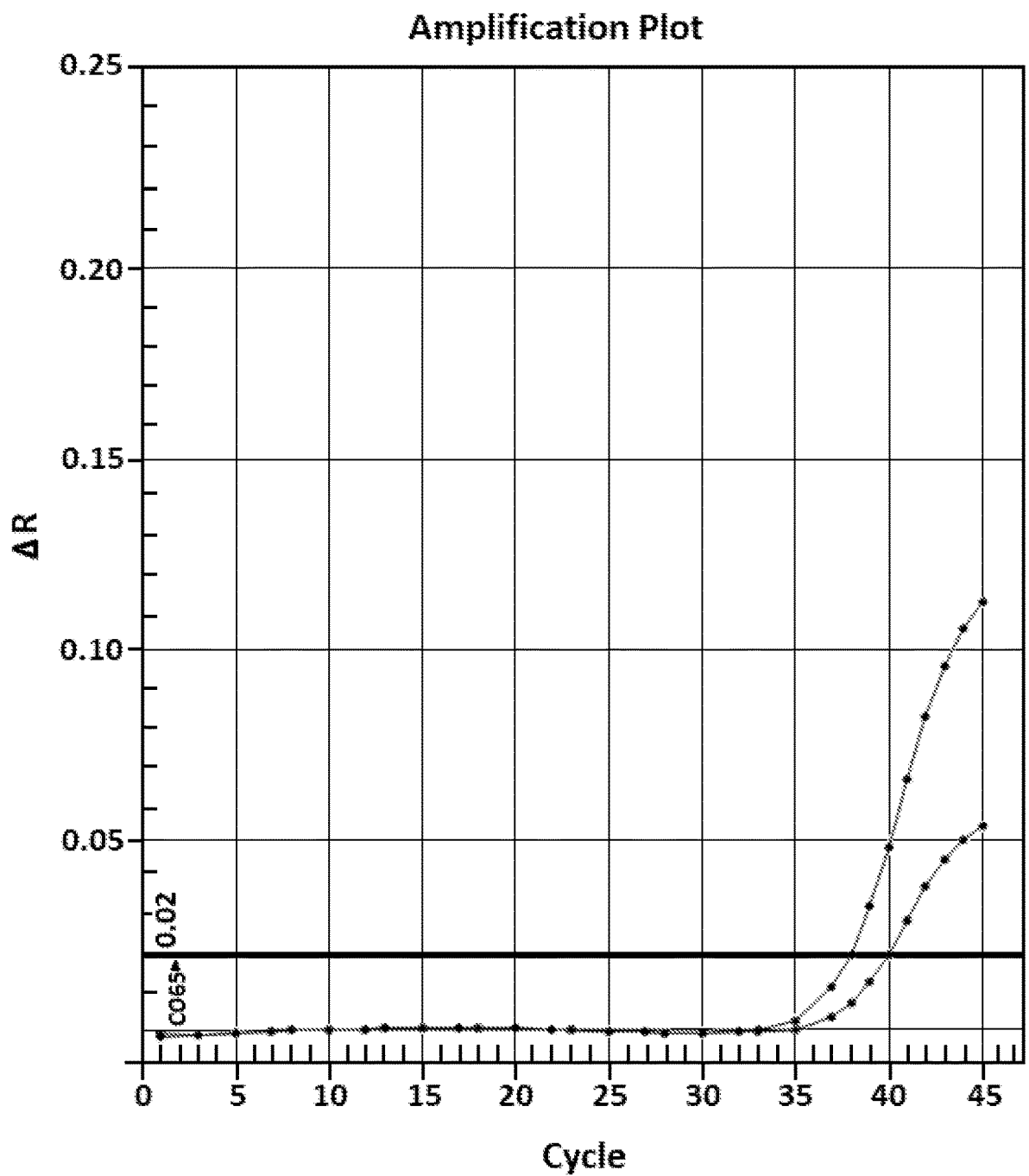

Results are shown in FIGS. 1A to 1II. The wild-type result (WT) is included with each panel, showing that it does not display significant signal. The mutants identified that generated significant signal are the following: V62S, V64S, A70F, F73A, A77F, P253G, E255K, D257R, A259F, A271F, L288S, E289K, S357I, L361S, L376S, P382G, T385I, G418P, R419D, E421K, L461S, A472F, E497K, L498S, E524K, D551R, R556D, S679I, L789S, E189K/E507K/E742K. The DNA and protein sequence of each of these mutants are in the sequence listing (see sequence listing guide above).

All patents, applications and references above are hereby incorporated by reference. The specific processes, methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A qPCR process comprising:
providing a qPCR mixture including a target nucleic acid, target nucleic acid primers, a mutant Taq DNA polymerase and an intercalating dye or a labeled target probe which fluoresces when the label is cleaved from the probe by exonuclease activity, wherein the mutant Taq DNA polymerase comprises the amino acid mutation A70F and the amino acid sequence of SEQ ID NO: 8, with the exception that the mutant Taq DNA polymerase does not include the 6-membered histidine tag at the C-terminus and the six immediately preceding Glycine and Serine amino acids included in SEQ ID NO: 8, providing a de-annealing temperature for a sufficient time to de-anneal primers from targets;

providing a number of cycles of an annealing temperature for a sufficient time to anneal primers to targets followed by an extension temperature held for about one second; and measuring a reporter signal generated to quantify the amount of target sequence present in the qPCR mixture.

2. The qPCR process of claim 1 wherein the de-annealing temperature is 95° C. for 30 seconds; the annealing temperature is 95° C. for 4 seconds and the extension temperature is 60° C.

3. The qPCR process of claim 1 wherein there are 40 cycles.

4. The qPCR process of claim 1 wherein the reporter signal is fluorescent.

5. The qPCR process of claim 1 wherein the reporter signal is from the labeled probe or the intercalating dye.

6. The qPCR process of claim 5 wherein the intercalating dye is SYBR Green or EvaGreen.

* * * * *